United States Patent
Ogez et al.

(10) Patent No.: US 11,071,782 B2
(45) Date of Patent: Jul. 27, 2021

(54) METHOD OF FILLING A CONTAINER WITH NO HEADSPACE

(71) Applicant: Coherus Biosciences, Inc., Redwood City, CA (US)

(72) Inventors: John Ogez, Longmont, CO (US); Jun Liu, Pacifica, CA (US); Wenchang Ji, Oak Park, CA (US); Patrick Daniel Begley, San Jose, CA (US); Isaias Prado, Oxnard, CA (US); Mark Manning, Johnstown, CO (US)

(73) Assignee: Coherus Biosciences, Inc., Redwood City, CA (US)

( * ) Notice: Subject to any disclaimer, the term of this patent is extended or adjusted under 35 U.S.C. 154(b) by 487 days.

(21) Appl. No.: 15/492,999

(22) Filed: Apr. 20, 2017

(65) Prior Publication Data

US 2017/0304445 A1 Oct. 26, 2017

Related U.S. Application Data

(60) Provisional application No. 62/325,387, filed on Apr. 20, 2016, provisional application No. 62/438,216, (Continued)

(51) Int. Cl.
*B65B 31/00* (2006.01)
*A61K 39/395* (2006.01)
(Continued)

(52) U.S. Cl.
CPC .......... *A61K 39/39591* (2013.01); *A61K 9/08* (2013.01); *A61K 47/183* (2013.01);
(Continued)

(58) Field of Classification Search
USPC .......................................................... 53/432
See application file for complete search history.

(56) References Cited

U.S. PATENT DOCUMENTS

| | | | |
|---|---|---|---|
| 4,597,966 | A | 7/1986 | Zolton et al. |
| 5,104,651 | A | 4/1992 | Boone et al. |
| (Continued) | | | |

FOREIGN PATENT DOCUMENTS

| | | |
|---|---|---|
| CA | 2872088 | 2/2004 |
| CN | 102049045 | 5/2011 |
| CN | 102257006 | 11/2011 |
| CN | 102988984 | 5/2015 |
| (Continued) | | |

OTHER PUBLICATIONS

Dominican Office Action in Application No. P2015-0051, dated Dec. 4, 2019, 9 pages.
(Continued)

*Primary Examiner* — Anna K Kinsaul
*Assistant Examiner* — Chinyere J Rushing-Tucker
(74) *Attorney, Agent, or Firm* — Fish & Richardson P.C.

(57) ABSTRACT

The present invention is directed to methods for filling a container wherein the filled container has no headspace. The present invention is further directed to methods for stabilizing an aqueous drug substance solution by filling a container with the aqueous drug substance solution wherein the filled container has no headspace. The present invention is further directed to methods for detecting headspace in a container.

8 Claims, 18 Drawing Sheets
(18 of 18 Drawing Sheet(s) Filed in Color)

Related U.S. Application Data filed on Dec. 22, 2016, provisional application No. 62/440,955, filed on Dec. 30, 2016, provisional application No. 62/453,370, filed on Feb. 1, 2017.

(51) Int. Cl.

| | | |
|---|---|---|
| *C07K 16/24* | (2006.01) | |
| *A61K 47/18* | (2017.01) | |
| *A61K 9/08* | (2006.01) | |
| *B65B 7/28* | (2006.01) | |
| *B65B 3/00* | (2006.01) | |
| *A61K 47/02* | (2006.01) | |
| *A61J 1/06* | (2006.01) | |
| *A61K 9/00* | (2006.01) | |

(52) U.S. Cl.
CPC ............ *B65B 3/003* (2013.01); *B65B 7/2821* (2013.01); *B65B 31/00* (2013.01); *C07K 16/241* (2013.01); *A61J 1/062* (2013.01); *A61K 9/0019* (2013.01); *A61K 47/02* (2013.01); *C07K 2317/21* (2013.01); *C07K 2317/76* (2013.01)

(56) References Cited

U.S. PATENT DOCUMENTS

| | | | |
|---|---|---|---|
| 5,716,988 A | 2/1998 | Ibrahim et al. | |
| 5,789,554 A | 8/1998 | Leung et al. | |
| 5,886,154 A | 3/1999 | Lebing et al. | |
| 5,945,098 A | 8/1999 | Samo et al. | |
| 6,090,382 A | 7/2000 | Salfed et al. | |
| 6,171,576 B1 | 1/2001 | Meltzer | |
| 6,171,586 B1 | 1/2001 | Lam et al. | |
| 6,238,664 B1 | 5/2001 | Hellerbrand et al. | |
| 6,252,055 B1 | 6/2001 | Relton | |
| 6,258,562 B1 | 7/2001 | Salfeld et al. | |
| 6,281,336 B1 | 8/2001 | Laursen et al. | |
| 6,509,015 B1 | 1/2003 | Salfeld | |
| 6,696,056 B1 | 2/2004 | Cheung et al. | |
| 7,188,644 B2 * | 3/2007 | Kelly ....................... B65B 3/04 141/2 | |
| 7,250,165 B2 | 7/2007 | Heavner et al. | |
| 7,648,702 B2 | 1/2010 | Gombotz et al. | |
| 7,879,976 B2 | 2/2011 | Friess et al. | |
| 8,216,583 B2 | 7/2012 | Krause | |
| 8,420,081 B2 | 4/2013 | Fraunhofer | |
| 8,632,778 B2 | 1/2014 | Kakuta et al. | |
| 8,664,945 B2 | 3/2014 | Laville | |
| 8,802,100 B2 | 8/2014 | Krause et al. | |
| 8,821,865 B2 | 9/2014 | Neu et al. | |
| 8,883,146 B2 | 11/2014 | Fraunhofer et al. | |
| 8,889,135 B2 | 11/2014 | Fischkoff et al. | |
| 8,916,157 B2 | 12/2014 | Krause | |
| 9,085,619 B2 | 7/2015 | Fraunhofer | |
| 9,114,166 B2 | 8/2015 | Krause | |
| 9,272,041 B2 | 3/2016 | Krause | |
| 9,340,611 B2 | 5/2016 | Manning et al. | |
| 9,340,612 B2 | 5/2016 | Manning et al. | |
| 9,346,880 B2 | 5/2016 | Manning et al. | |
| 9,382,317 B2 | 7/2016 | Manning et al. | |
| 9,682,145 B2 | 6/2017 | Manning et al. | |
| 9,707,293 B2 | 7/2017 | Manning et al. | |
| 9,724,414 B2 | 8/2017 | Manning et al. | |
| 9,724,415 B2 | 8/2017 | Manning et al. | |
| 9,731,008 B2 | 8/2017 | Manning et al. | |
| 9,731,009 B2 | 8/2017 | Manning et al. | |
| 9,737,600 B2 | 8/2017 | Manning et al. | |
| 9,738,714 B2 | 8/2017 | Krause | |
| 9,757,454 B2 | 9/2017 | Manning et al. | |
| 9,770,507 B2 | 9/2017 | Manning et al. | |
| 9,782,479 B2 | 10/2017 | Manning et al. | |
| 9,782,480 B2 | 10/2017 | Manning et al. | |
| 9,789,185 B2 | 10/2017 | Manning et al. | |
| 9,808,525 B2 | 11/2017 | Manning et al. | |
| 9,861,695 B2 | 1/2018 | Manning et al. | |
| 10,155,039 B2 | 12/2018 | Manning et al. | |
| 10,159,732 B2 | 12/2018 | Manning et al. | |
| 10,159,733 B2 | 12/2018 | Manning et al. | |
| 10,195,275 B2 | 2/2019 | Manning et al. | |
| 10,207,000 B2 | 2/2019 | Manning et al. | |
| 10,716,852 B2 | 7/2020 | Manning et al. | |
| 10,716,853 B2 | 7/2020 | Manning et al. | |
| 10,716,854 B2 | 7/2020 | Manning et al. | |
| 10,722,579 B2 | 7/2020 | Manning et al. | |
| 2002/0004478 A1 | 1/2002 | Danko et al. | |
| 2003/0138417 A1 | 7/2003 | Kaisheva et al. | |
| 2003/0180287 A1 | 9/2003 | Gombotz et al. | |
| 2003/0206898 A1 | 11/2003 | Fischkoff et al. | |
| 2004/0022792 A1 | 2/2004 | Klinke | |
| 2004/0033228 A1 | 2/2004 | Krause et al. | |
| 2004/0033535 A1 | 2/2004 | Boyle et al. | |
| 2004/0038878 A1 | 2/2004 | Tanikawa et al. | |
| 2004/0039366 A1 * | 2/2004 | MacLeod ............... A61J 1/2093 604/416 | |
| 2004/0170623 A1 | 9/2004 | Arvinte et al. | |
| 2006/0149042 A1 | 7/2006 | Konstantinov et al. | |
| 2006/0165733 A1 | 7/2006 | Betz et al. | |
| 2007/0036779 A1 | 2/2007 | Bardat et al. | |
| 2007/0169435 A1 * | 7/2007 | Kinney ................... B65B 3/003 53/432 | |
| 2007/0184050 A1 | 8/2007 | Ishikawa | |
| 2008/0124326 A1 | 5/2008 | Rehder et al. | |
| 2008/0275220 A1 * | 11/2008 | Friess ............... A61K 39/39591 530/387.3 | |
| 2008/0311078 A1 | 12/2008 | Gokametal | |
| 2009/0151807 A1 | 6/2009 | Davis et al. | |
| 2009/0291062 A1 | 11/2009 | Fraunhofer | |
| 2010/0199774 A1 | 8/2010 | Stenzel | |
| 2010/0278822 A1 | 11/2010 | Fraunhofer | |
| 2011/0060290 A1 * | 3/2011 | Bonk ..................... A61K 9/0019 604/181 | |
| 2012/0028877 A1 | 2/2012 | Gokam et al. | |
| 2013/0195888 A1 | 8/2013 | Wang et al. | |
| 2013/0216522 A1 | 8/2013 | Huille et al. | |
| 2013/0216525 A1 | 8/2013 | Chen | |
| 2013/0243764 A1 | 9/2013 | Ellis et al. | |
| 2013/0273066 A1 | 10/2013 | Gokametal | |
| 2013/0273067 A1 | 10/2013 | Gokarn et al. | |
| 2013/0312868 A1 * | 11/2013 | Ilan ....................... B01F 5/0685 141/4 | |
| 2013/0336968 A1 | 12/2013 | Danek-Bulius et al. | |
| 2014/0141007 A1 | 5/2014 | Fraunhofer et al. | |
| 2014/0141008 A1 | 5/2014 | Fraunhofer et al. | |
| 2014/0186361 A1 | 7/2014 | Manning et al. | |
| 2015/0102042 A1 | 4/2015 | Matsch | |
| 2015/0150982 A1 | 6/2015 | Michael et al. | |
| 2015/0182626 A1 | 7/2015 | Manning et al. | |
| 2015/0190513 A1 | 7/2015 | Manning et al. | |
| 2015/0191538 A1 | 7/2015 | Manning et al. | |
| 2015/0290080 A1 * | 10/2015 | Weikart ................. C23C 16/401 206/438 | |
| 2015/0344557 A1 * | 12/2015 | Malik ............... A61K 39/39591 424/142.1 | |
| 2016/0015895 A1 * | 1/2016 | Blondino ............. A61M 5/3234 604/506 | |
| 2016/0031982 A1 | 2/2016 | Manning et al. | |
| 2016/0039926 A1 | 2/2016 | Manning et al. | |
| 2016/0256545 A1 | 9/2016 | Manning et al. | |
| 2016/0256547 A1 | 9/2016 | Manning et al. | |
| 2016/0263226 A1 | 9/2016 | Manning et al. | |
| 2016/0303233 A1 | 10/2016 | Manning et al. | |
| 2016/0303234 A1 | 10/2016 | Manning et al. | |
| 2016/0303235 A1 | 10/2016 | Manning et al. | |
| 2016/0304599 A1 | 10/2016 | Manning et al. | |
| 2016/0304600 A1 | 10/2016 | Manning et al. | |
| 2016/0304601 A1 | 10/2016 | Manning et al. | |
| 2016/0319011 A1 | 11/2016 | Gokam et al. | |
| 2016/0339102 A1 | 11/2016 | Gokarn et al. | |
| 2016/0362484 A1 | 12/2016 | Gokarn et al. | |
| 2016/0362486 A1 | 12/2016 | Gokarn et al. | |
| 2017/0143828 A1 | 5/2017 | Fraunhofer et al. | |
| 2017/0312361 A1 | 11/2017 | Manning et al. | |

(56) References Cited

U.S. PATENT DOCUMENTS

| | | |
|---|---|---|
| 2018/0021433 A1 | 1/2018 | Manning et al. |
| 2018/0028653 A1 | 2/2018 | Manning et al. |
| 2018/0028654 A1 | 2/2018 | Manning et al. |
| 2018/0028655 A1 | 2/2018 | Manning et al. |
| 2018/0028656 A1 | 2/2018 | Manning et al. |
| 2018/0028657 A1 | 2/2018 | Manning et al. |
| 2018/0043018 A1 | 2/2018 | Manning et al. |
| 2018/0043019 A1 | 2/2018 | Manning et al. |
| 2018/0055929 A1 | 3/2018 | Manning et al. |
| 2018/0055930 A1 | 3/2018 | Manning et al. |
| 2018/0140701 A1 | 5/2018 | Manning et al. |
| 2018/0200202 A1* | 7/2018 | Joguparthi .............. C09J 175/16 |
| 2018/0256717 A1* | 9/2018 | Klaveness ................ A61K 9/19 |
| 2018/0311349 A1 | 11/2018 | Manning et al. |
| 2018/0311350 A1 | 11/2018 | Manning et al. |
| 2018/0311351 A1 | 11/2018 | Manning et al. |
| 2018/0311352 A1 | 11/2018 | Manning et al. |
| 2019/0060455 A1 | 2/2019 | Manning et al. |
| 2019/0070292 A1 | 3/2019 | Manning et al. |
| 2019/0070293 A1 | 3/2019 | Manning et al. |
| 2019/0070294 A1 | 3/2019 | Manning et al. |

FOREIGN PATENT DOCUMENTS

| | | |
|---|---|---|
| EP | 1324776 | 9/2009 |
| EP | 1528933 | 5/2012 |
| JP | 2001-503781 | 3/2001 |
| JP | 2010-523493 | 7/2010 |
| JP | 2011-509972 | 3/2011 |
| JP | 2011-518110 | 6/2011 |
| JP | 2015-527402 | 9/2015 |
| WO | WO 1997/029131 | 8/1997 |
| WO | WO 1997/45140 | 12/1997 |
| WO | WO 1998/004281 | 2/1998 |
| WO | WO 1998/056418 | 12/1998 |
| WO | WO 1999/037329 | 7/1999 |
| WO | WO 2000/56772 | 9/2000 |
| WO | WO 2000/67789 | 11/2000 |
| WO | WO 2002/013860 | 2/2002 |
| WO | WO 2002/100330 | 12/2002 |
| WO | WO 2006/022599 | 3/2006 |
| WO | WO 2006/138181 | 12/2006 |
| WO | WO 2007/092772 | 8/2007 |
| WO | WO 2004/091656 | 10/2008 |
| WO | WO 2009/015345 | 1/2009 |
| WO | WO 2009/073569 | 6/2009 |
| WO | WO 2009/073805 | 6/2009 |
| WO | WO 2009/084659 | 7/2009 |
| WO | WO 2010/062896 | 6/2010 |
| WO | WO 2010/066634 | 6/2010 |
| WO | WO 2010/129469 | 11/2010 |
| WO | WO 2010/141039 | 12/2010 |
| WO | WO 2011/061712 | 5/2011 |
| WO | WO 2011/080209 | 7/2011 |
| WO | WO 2011/141926 | 11/2011 |
| WO | WO 2012/037534 | 3/2012 |
| WO | WO 2012/065072 | 5/2012 |
| WO | WO 2012/143418 | 10/2012 |
| WO | WO 2012/165917 | 12/2012 |
| WO | WO 2013/006454 | 1/2013 |
| WO | WO 2013/011076 | 1/2013 |
| WO | WO 2013/063510 | 5/2013 |
| WO | WO 2013/096835 | 6/2013 |
| WO | WO 2013/164837 | 11/2013 |
| WO | WO 2014/186230 | 12/2013 |
| WO | WO 2014/039903 | 3/2014 |
| WO | WO 2014/099636 | 6/2014 |
| WO | WO 2014/130064 | 8/2014 |

OTHER PUBLICATIONS

Falconer et al., "Stabilization of a monoclonal antibody during purification and formulation by addition of basic amino acid excipients", J Chem Technol. Biotechnol. 86:942-948, 2011.

Japanese Office Action in Application No. 2018-244382, dated Jan. 14, 2020, English Translation, 5 pages.
U.S. Appl. No. 16/023,046, filed Jun. 29, 2018, Fraunhofer et al.
U.S. Appl. No. 16/023,152, filed Jun. 29, 2018, Fraunhofer et al.
U.S. Appl. No. 16/023,161, filed Jun. 29, 2018, Fraunhofer et al.
U.S. Appl. No. 16/023,205, filed Jun. 29, 2018, Fraunhofer et al.
U.S. Appl. No. 16/178,137, filed Nov. 1, 2018, Manning et al.
U.S. Appl. No. 16/178,164, filed Nov. 1, 2018, Manning et al.
U.S. Appl. No. 16/178,309, filed Nov. 1, 2018, Manning et al.
U.S. Appl. No. 16/178,319, filed Nov. 1, 2018, Manning et al.
U.S. Appl. No. 61/004,992, filed Nov. 30, 2017, Fraunhofer et al.
"Annex A Humira Story," Abbive Biotechnology Limited, submitted to European Patent Office by owner of EP1406656B on Dec. 22, 2014.
"Declaration of Brian Reisetter, RPh, MBA, Ph.D.," filed with Petition for *Inter Partes* Review of U.S. Pat. No. 9,114,166 filed May 9, 2019, 15 pages.
"Development Pharmaceutics for Biotechnological and Biological Products (Annex to Note for Guidance on Development Pharmaceutics)," by Committee for Proprietary Medicinal Products, The European Agency for the Evaluation of Medicinal Products (Oct. 21, 1999).
"Expert Opinion of Prof. Dr. G. Winter," Jan. 13, 2014, in opposition proceedings re EP1528933.
"Fraunhofer Substantive Motion 3," in *Fraunhofer v. Gokarn*, Patent Interference No. 106,057, filed on Oct. 12, 2016, 57 pages.
"Immune Globulin Intravenous (Human), 10% Caprylate/Chromatography Purified," Talecris Biotherapeutics, Inc., dated Nov. 2005, 17 pages.
"Note for Guidance on Development Pharmaceutics," by the Committee for Proprietary Medicinal Products (CPMP), The European Agency for the Evaluation of Medicinal Products (Jan. 28, 1998).
"Abbott Ramps Up Biotech Manufacturing to Meet Humira Demand," Pharmaceutical Technology, Mar. 2003, 4 pages.
"Clinical Pharmacology and Biopharmaceutics Review(s)," by Center for Drug Evaluation and Research and Center for Biologics Evaluation and Research Application No. 125057/0, in Approval Package for Humira®, 67 pages, Approved Dec. 31, 2002.
FDA Approves Amgen's Amjevita™ (Adalimumab-Atto) for Treatment of Seven Inflammatory Diseases (Sep. 23, 2019), https://www.amgen.com/media/news-releases/2016/09/fda-approves-amgens-amjevita-adalimumabatto-for-treatment-of-seven-inflammatmy-diseases/, 8 pages.
"Grounds of Appeal," Exhibit 1085 in Opposition of EP 1528933, filed Feb. 26, 2016, 27 pages.
Marketing Authorization No. EU/16/1164) European Medicines Agency, "Amgenvita" https://ec.europa.eu/health/documents/community-register/html/h1164.htm, 5 pages, 2019.
2015 Express Scripts Basic Formulary, Aug. 2014, 2 pages.
Abbott Laboratories 2003 Annual Report, 80 pages.
AbbVie Filing in Support of Opposition Against EP 1324776 B1, Filed Jun. 16, 2010.
AbbVie Filing in Support of Opposition Against EP 1324776 B1, filed Jun. 16, 2010 (Corrected), 24 pages.
Adalimumab Product Approval Information—Licensing Action, Humira, Dec. 31, 2002, 1 page.
Additional Experimental Results for EP 03 748 438 (sic 439) Abbott Biotechnology, Submitted May 15, 2009 in Prosecution of EP1528933.
Affidavit of Christopher Butler dated Feb. 21, 2017, attaching "Injection Tips," Humira.com, http://web.archive.org!web/20050317083331/http://www.humira.com/hu/hustore/cgi-bin/ProdSubEV_Cat_205043_SubCat_210170_NavRoot_205042_NavID_301 .htm (Archived Mar. 17, 2005) As Exhibit A, 2 pages.
Affidavit of Marlene S. Bobka dated Feb. 21, 2017, attaching "Clinical Pharmacology and Biopharmaceutics Review(s)," by Center for Drug Evaluation and Research and Center for Biologics Evaluation and Research, Application No. 125057/0, in Approval Package for Humira, Approved Dec. 31, 2002 as Exhibit A, 67 pages.
Affidavit of Michael Deas attaching English Translation of OCTAGAM entry (75 008) in Rote Liste 2005, Cantor Publishers 2005, as Exhibit A, and original German-language Rote Liste 2005 entry 75 008 as Exhibit B and C, 13 pages.

(56) References Cited

OTHER PUBLICATIONS

Akers et al., "Formulation Development of Protein Dosage Forms," Ch. 2 in Development and Manufacture of Protein Pharmaceuticals, Kluwer Academic/Plenum Publishers: New York, pp. 47-127, 2002.

Alon et al., "Lidocaine for the Alleviation of Pain Associated with Subcutaneous Erythropoietin Injection," Journal of the American Soc. of Nephrology, vol. 5, No. 4, pp. 1161-1162, 1994.

Ann L. Daugherty et al., "Formulation and Delivery Issues for Monoclonal Antibody Therapeutics," Adv. Drug Deliv. Rev. 58:686 (2006).

Arakawa et al., "Protection of Bovine Serum Albumin from Aggregation by Tween 80," J. Pharm. Sci. 89(5):646-651, May 2000.

Arakawa et al., "Protection of Bovine Serum Albumin from Aggregation by Tween 80," J. Phann. Sci. 89(5):646-651 (May 2000).

Atgam® Label (Nov. 2005).

Aulton, ed., "Pharmaceutics, The Science of Dosage Form Design," 2nd ed., Churchill Livingstone: New York, pp. 317-318, 544-553, 2002.

Australian Examination Report No. 1 in Australian Appln. No. 2013312300, dated Jul. 28, 2017, 4 pages.

Avastin® Label (Feb. 2004).

Bahrenburg et al., "Buffer-free therapeutic antibody preparations provided a viable alternative to conventionally buffered solutions: From protein buffer capacity prediction to bioprocess applications," Bio. J. 10:610-622, 2015.

Bam et al., "Tween Protects Recombinant Human Growth Hormone against Agitation-Induced Damage via Hydrophobic Interactions," J. Pharm. Sci., 87(12):1554-1559, Dec. 1998.

Banks et al., "Native-State Solubility and Transfer Free Energy as Predictive Tools for Selecting Excipients to Include in Protein Formulation Development Studies," J. Pharm. Sci. 101:2720-2732, 2012.

Barrera et al., "Effects of treatment with a fully human anti-tumour necrosis factor α monoclonal antibody on the local and systemic homeostasis of interleukin 1 and TNFα in patients with rheumatoid arthritis," Ann. Rheum. Dis. 60:660-669, 2001.

Barsamian et al., "Physcians' Desk Reference: ZEVALIN," Thomson PDR, 60 Edition, year 2006, 8 pages.

Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncology 14(3):737-744, 1996.

Bischoff et al., "Deamidation of Asparagine and Glutamine Residues in Proteins and Peptides: Structural Determinants and Analytical Methodology," J. of Chromatography B 662:261-278, 1994.

Branden A. Salinas et al., "Understanding and Modulating Opalescence and Viscosity in a Monoclonal Antibody Formulation," 99 J. Pharm. Sci. 82 (2010).

Brazeau et al., "Current perspectives on pain upon injection of drugs," Journal of Pharm. Sci., vol. 87, No. 6, pp. 667-677, 1998.

Breu et al., "Biotech company preparing several drugs for takeoff," Drug Topics, dated Mar. 5, 2001, 1 page.

Burton et al., "Aspects of the Molecular Structure of IgG Subclasses," Monogr. Allergy vol. 19, pp. 7-35, 1986.

Butler & Hamilton, "Quantitation of Specific Antibodies: Methods of Express, Standards, Solid-Phase Considerations, and Specific Applications," Ch. 9 in Immunochemistry of Solid-Phase Immunoassay, CRC Press (John E. Butler ed. 1991).

Campath (Alemtuzumab), Genzyme Corporation, 2006.

Canadian Office Action in Application No. 2884182, dated Oct. 18, 2019, 4 pages.

Capasso et al., "Effect of the Three-Dimensional Structure on the Deamidation Reaction of Ribonuclease A," J. Peptide Res. 54:377-382, 1999.

Capasso et al., "First Evidence of Spontaneous Deamidation of Glutamine Residue via Cyclic Imide to α- and γ-Glutamic Residue under Physiological Conditions," J. Chem. Soc. Chem. Comm., pp. 1667-1668, 1991.

Carnahan et al., "Epratuzumab, a Humanized Monoclonal Antibody Targeting CD22: Characterization of in Vitro Properties," vol. 9, pp. 3982s-3990s, Sep. 1, 2003.

Carpenter and Manning, eds., "Rational Design of Stable Protein Formulations. Theory and Practice," Pharmaceutical Biotechnology, vol. 13, Kluwer Academic/Plenum Publishers: New York, 222 pages, 2002.

Carpenter et al., "Freezing and Drying-Induced Perturbations of Protein Structure and Mechanisms of Protein Production by Stabilizing Additives," Freeze-Drying/Lyophilization of Pharmaceutical and Biological Products, 2004, pp. 167-197.

Carpenter et al., "Inhibition of Stress-induced Aggregation of Protein Therapeutics," Methods in Enzymology 309:236-255, 1999.

Carpenter et al., "Overlooking Subvisible Particles in Therapeutic Protein Products: Gaps That May Compromise Product Quality," J. Pharm. Sci. 98(4):1201-1205, Apr. 2009.

Chen et al., "Aggregation Pathway of Recombinant Human Keratinocyte Growth Factor and Its Stabilization," Pharmaceutical Research, vol. II, No. II, dated Jun. 6, 1994, 7 pages.

Chi et al., "Physical Stability of Proteins in Aqueous Solution: Mechanism and Driving Forces in Nonnative Protein Aggregation," Pharm. Research, vol. 20, No. 9, dated Sep. 2003, 12 pages.

Chinese Office Action in Application No. 201380058126.8, dated Oct. 23, 2019, 12 pages.

Chinese Office Action in Chinese Appln. No. 20130058126.8, dated Nov. 16, 2015, 14 pages (with machine translation).

Christensen, "Proteins as buffers," Annals of the New York Academy of Sciences, 133:34-40 (Apr. 1966).

Christine C. Lee et al., "Toward aggregation-resistant antibodies by design," 31 Trends in Biotech. 612 (2013).

Cleland & Langer, "Formulation and Delivery of Proteins and Peptides: Design and Development Strategies," Ch. 1 in Formulation and Delivery of Proteins and Peptides, ACS Symposium Series 567, pp. 1-19 (1994).

Cleland et al., "The Development of Stable protein Formulations: A Close Look at Protein Aggregation, Deamidation, and Oxidation," Critical Reviews in Therapeutic Drug Carrier Systems, 10(4):307-377 (1993).

CNJ-016, Vaccinia Immune Globulin Intravenous, Label Apr. 2005, 18 pages.

*Coherus Biosciences Inc.*, Petitioner v. *AbbVie Biotechnology Ltd.*, "Amgen Inc.'s Answer, Affirmative Defenses, and Counterclaims," filed in the U.S. District Court for the District of Delaware, C.A. No. 19-139-RGA, Case IPR2016-01018, U.S. Pat. No. 9,114,166, dated Aug. 18, 2019.

*Coherus Biosciences Inc.*, Petitioner v. *AbbVie Biotechnology Ltd.*, "Decision Denying Institution of *Inter Partes* Review," Case IPR2017-01009, U.S. Pat. No. 9,085,619, dated Sep. 7, 2017, 22 pages.

*Coherus Biosciences Inc.*, Petitioner v. *AbbVie Biotechnology Ltd.*, "Decision Denying Institution of *Inter Partes* Review," Case IPR2016-01018, U.S. Pat. No. 9,114,166, dated Nov. 7, 2016.

*Coherus Biosciences Inc.*, Petitioner v. *AbbVie Biotechnology Ltd.*, "Decision Denying Petitioner's Request for Rehearing in *Inter Partes* Review," Case IPR2016-01018, U.S. Pat. No. 9,114,166, dated Feb. 2, 2017.

*Coherus Biosciences Inc.*, Petitioner v. *AbbVie Biotechnology Ltd.*, "Declaration of David D. Sherry, M.D.," Case IPR2017-00827, U.S. Pat. No. 9,085,619, dated Jan. 30, 2017, 43 pages.

*Coherus Biosciences Inc.*, Petitioner v. *AbbVie Biotechnology Ltd.*, "Declaration of David D. Sherry, M.D.," Case IPR2017-01008, U.S. Pat. No. 9,085,619, dated Feb. 26, 2017, 43 pages.

*Coherus Biosciences Inc.*, Petitioner v. *AbbVie Biotechnology Ltd.*, "Declaration of David D. Sherry, M.D.," Case IPR2017-01009, U.S. Pat. No. 9,085,619, dated Feb. 26, 2017, 43 pages.

*Coherus Biosciences Inc.*, Petitioner v. *AbbVie Biotechnology Ltd.*, "Declaration of David D. Sherry M.D.," Case IPR2017-00826, U.S. Pat. No. 9,085,619, dated Jan. 30, 2017, 43 pages.

*Coherus Biosciences Inc.*, Petitioner v. *AbbVie Biotechnology Ltd.*, "Declaration of Klaus-Peter Radtke, Ph.D.," Case IPR2017-00826, U.S. Pat. No. 9,085,619, dated Jan. 30, 2017, 96 pages.

*Coherus Biosciences Inc.*, Petitioner v. *AbbVie Biotechnology Ltd.*, "Declaration of Klaus-Peter Radtke, Ph.D.," Case IPR2017-00827, U.S. Pat. No. 9,085,619, dated Jan. 30, 2017, 121 pages.

(56) References Cited

OTHER PUBLICATIONS

*Coherus Biosciences Inc.*, Petitioner v. *AbbVie Biotechnology Ltd.*, "Declaration of Klaus-Peter Radtke, Ph.D.," Case IPR2017-01008. U.S. Pat. No. 9,085,619, dated Feb. 28, 2017, 127 pages.
*Coherus Biosciences Inc.*, Petitioner v. *AbbVie Biotechnology Ltd.*, "Declaration of Klaus-Peter Radtke, Ph.D.," Case IPR2017-01009. U.S. Pat. No. 9,085,619, dated Feb. 28, 2017, 104 pages.
*Coherus Biosciences Inc.*, Petitioner v. *AbbVie Biotechnology Ltd.*, "Notice of Accepting Corrected Petition," Case IPR2016-01018, U.S. Pat. No. 9,114,166, May 16, 2016, 2 pages.
*Coherus Biosciences Inc.*, Petitioner v. *AbbVie Biotechnology Ltd.*, "Notice of Corrected Exhibit," Case IPR2016-01018, U.S. Pat. No. 9,114,166, dated May 13, 2016, 3 pages.
*Coherus Biosciences Inc.*, Petitioner v. *AbbVie Biotechnology Ltd.*, "Notice of Corrected List of Exhibits," Case IPR2016-01018, U.S. Pat. No. 9,114,166, dated May 13, 2016, 10 pages.
*Coherus Biosciences Inc.*, Petitioner v. *AbbVie Biotechnology Ltd.*, "Notice of Filing Date Accorded to Petition and Time for Filing Patent Owner Preliminary Response," Case IPR2017-00826, U.S. Pat. No. 9,085,619, dated Feb. 24, 2017, 5 pages.
*Coherus Biosciences Inc.*, Petitioner v. *AbbVie Biotechnology Ltd.*, "Notice of Filing Date Accorded to Petition and Time for Filing Patent Owner Preliminary Response," Case IPR2017-01008, U.S. Pat. No. 9,085,619, dated Mar. 24, 2017, 5 pages.
*Coherus Biosciences Inc.*, Petitioner v. *AbbVie Biotechnology Ltd.*, "Notice of Filing Date Accorded to Petition and Time for Filing Patent Owner Preliminary Response," Case IPR2017-01009, U.S. Pat. No. 9,085,619, dated Mar. 24, 2017, 5 pages.
*Coherus Biosciences Inc.*, Petitioner v. *AbbVie Biotechnology Ltd.*, "Notice of Filing Date Accorded to Petition," Case IPR2016-01018, U.S. Pat. No. 9,114,166, dated May 11, 2016, 5 pages.
*Coherus Biosciences Inc.*, Petitioner v. *AbbVie Biotechnology Ltd.*, "Notice of Refund," Case IPR2017-00826, U.S. Pat. No. 9,085,619, dated Jun. 5, 2017, 2 pages.
*Coherus Biosciences Inc.*, Petitioner v. *AbbVie Biotechnology Ltd.*, "Notice of Refund," Case IPR2017-00827, U.S. Pat. No. 9,085,619, dated Jun. 5, 2017, 2 pages.
*Coherus Biosciences Inc.*, Petitioner v. *AbbVie Biotechnology Ltd.*, "Notice of Refund," Case IPR2017-01008, U.S. Pat. No. 9,085,619, dated Dec. 1, 2017, 2 pages.
*Coherus Biosciences Inc.*, Petitioner v. *AbbVie Biotechnology Ltd.*, "Notice of Refund," Case IPR2017-01009, U.S. Pat. No. 9,085,619, dated Dec. 30, 2017, 2 pages.
*Coherus Biosciences Inc.*, Petitioner v. *AbbVie Biotechnology Ltd.*, "Order Conduct of the Proceeding," Case IPR2017-00826, U.S. Pat. No. 9,085,619, dated Apr. 7, 2017, 6 pages.
*Coherus Biosciences Inc.*, Petitioner v. *AbbVie Biotechnology Ltd.*, "Order Conduct of the Proceeding," Case IPR2017-00827, U.S. Pat. No. 9,085,619, dated Apr. 7, 2017 6 pages.
*Coherus Biosciences Inc.*, Petitioner v. *AbbVie Biotechnology Ltd.*, "Order Conduct of the Proceeding," Case IPR2017-01008, U.S. Pat. No. 9,085,619, dated Apr. 7, 2017 6 pages.
*Coherus Biosciences Inc.*, Petitioner v. *AbbVie Biotechnology Ltd.*, "Order Conduct of the Proceeding," Case IPR2017-01009, U.S. Pat. No. 9,085,619, dated Apr. 7, 2017 6 pages.
*Coherus Biosciences Inc.*, Petitioner v. *AbbVie Biotechnology Ltd.*, "Order Dismissing the Proceedings," Case IPR2017-00826, U.S. Pat. No. 9,085,619, dated Apr. 11, 2017, 4 pages.
*Coherus Biosciences Inc.*, Petitioner v. *AbbVie Biotechnology Ltd.*, "Order Dismissing the Proceedings," Case IPR2017-00827, U.S. Pat. No. 9,085,619, dated Apr. 11, 2017 4 pages.
*Coherus Biosciences Inc.*, Petitioner v. *AbbVie Biotechnology Ltd.*, "Patent Owner Preliminary Response in *Inter Partes* Review," Case IPR2016-01018, U.S. Pat. No. 9,114,166, dated Aug. 9, 2016.
*Coherus Biosciences Inc.*, Petitioner v. *AbbVie Biotechnology Ltd.*, "Patent Owner's Mandatory Notices," Case IPR2016-01018, U.S. Pat. No. 9,114,166, May 27, 2016, 5 pages.
*Coherus Biosciences Inc.*, Petitioner v. *AbbVie Biotechnology Ltd.*, "Patent Owner's Powers of Attorney," Case IPR2016-01018, U.S. Pat. No. 9,114,166, dated May 24, 2016, 2 pages.

*Coherus Biosciences Inc.*, Petitioner v. *AbbVie Biotechnology Ltd.*, "Patent Owners Mandatory Notice," Case IPR2017-00827, U.S. Pat. No. 9,085,619, dated Feb. 21, 2017 6 pages.
*Coherus Biosciences Inc.*, Petitioner v. *AbbVie Biotechnology Ltd.*, "Patent Owners Mandatory Notices," Case IPR2017-00826, U.S. Pat. No. 9,085,619, dated Feb. 21, 2017, 6 pages.
*Coherus Biosciences Inc.*, Petitioner v. *AbbVie Biotechnology Ltd.*, "Patent Owners Mandatory Notices," Case IPR2017-01008, U.S. Pat. No. 9,085,619, dated Mar. 23, 2017, 6 pages.
*Coherus Biosciences Inc.*, Petitioner v. *AbbVie Biotechnology Ltd.*, "Patent Owners Mandatory Notices," Case IPR2017-01009, U.S. Pat. No. 9,085,619, dated Mar. 23, 2017, 6 pages.
*Coherus Biosciences Inc.*, Petitioner v. *AbbVie Biotechnology Ltd.*, "Patent Owners Power of Attorney," Case IPR2017-00826, U.S. Pat. No. 9,085,619, dated Feb. 21, 2017, 2 pages.
*Coherus Biosciences Inc.*, Petitioner v. *AbbVie Biotechnology Ltd.*, "Patent Owners Power of Attorney," Case IPR2017-01008, U.S. Pat. No. 9,085,619, dated Mar. 17, 2017, 2 pages.
*Coherus Biosciences Inc.*, Petitioner v. *AbbVie Biotechnology Ltd.*, "Patent Owners Power of Attorney," Case IPR2017-01009, U.S. Pat. No. 9,085,619, dated Mar. 17, 2017, 2 pages.
*Coherus Biosciences Inc.*, Petitioner v. *AbbVie Biotechnology Ltd.*, "Patent Owners Power of Attorney," Case IPR2017-00827, U.S. Pat. No. 9,085,619, dated Feb. 21, 2017 2 pages.
*Coherus Biosciences Inc.*, Petitioner v. *AbbVie Biotechnology Ltd.*, "Patent Owners Preliminary Response," Case IPR2016-01018, U.S. Pat. No. 9,114,166, dated Aug. 9, 2016, 77 pages.
*Coherus Biosciences Inc.*, Petitioner v. *AbbVie Biotechnology Ltd.*, "Patent Owners Preliminary Response," Case IPR2017-00827, U.S. Pat. No. 9,085,619, dated Aug. 9, 2016, 77 pages.
*Coherus Biosciences Inc.*, Petitioner v. *AbbVie Biotechnology Ltd.*, "Patent Owners Preliminary Response," Case IPR2017-01008, U.S. Pat. No. 9,085,619, dated Jun. 11, 2017, 81 pages.
*Coherus Biosciences Inc.*, Petitioner v. *AbbVie Biotechnology Ltd.*, "Patent Owners Preliminary Response," Case IPR2017-01009, U.S. Pat. No. 9,085,619, dated Jun. 11, 2017, 59 pages.
*Coherus Biosciences Inc.*, Petitioner v. *AbbVie Biotechnology Ltd.*, "Patent Owners Second Updated Mandatory Notice," Case IPR2017-00827, U.S. Pat. No. 9,085,619, dated Mar. 17, 2017 5 pages.
*Coherus Biosciences Inc.*, Petitioner v. *AbbVie Biotechnology Ltd.*, "Patent Owners Second Updated Mandatory Notices," Case IPR2017-00826, U.S. Pat. No. 9,085,619, dated Mar. 17, 2017, 5 pages.
*Coherus Biosciences Inc.*, Petitioner v. *AbbVie Biotechnology Ltd.*, "Patent Owners Updated Mandatory Notice," Case IPR2017-00827, U.S. Pat. No. 9,085,619, dated Feb. 27, 2017 4 pages.
*Coherus Biosciences Inc.*, Petitioner v. *AbbVie Biotechnology Ltd.*, "Patent Owners Updated Mandatory Notices," Case IPR2017-00826, U.S. Pat. No. 9,085,619, dated Feb. 27, 2017, 4 pages.
*Coherus Biosciences Inc.*, Petitioner v. *AbbVie Biotechnology Ltd.*, "Patent Owners Updated Mandatory Notices," Case IPR2017-01008, U.S. Pat. No. 9,085,619, dated Jun. 11, 2017, 4 pages.
*Coherus Biosciences Inc.*, Petitioner v. *AbbVie Biotechnology Ltd.*, "Patent Owners Updated Mandatory Notices," Case IPR2017-01009, U.S. Pat. No. 9,085,619, dated Jun. 11, 2017, 4 pages.
*Coherus Biosciences Inc.*, Petitioner v. *AbbVie Biotechnology Ltd.*, "Patent Owners Updated Power of Attorney," Case IPR2017-01008, U.S. Pat. No. 9,085,619, dated Jun. 7, 2017, 4 pages.
*Coherus Biosciences Inc.*, Petitioner v. *AbbVie Biotechnology Ltd.*, "Patent Owners Updated Power of Attorney," Case IPR2017-01009, U.S. Pat. No. 9,085,619, dated Jun. 7, 2017, 4 pages.
*Coherus Biosciences Inc.*, Petitioner v. *AbbVie Biotechnology Ltd.*, "Petitioners Request for Refund of Post Institution Fees," Case IPR2017-00827, U.S. Pat. No. 9,085,619, dated May 25, 2017 4 pages.
*Coherus Biosciences Inc.*, Petitioner v. *AbbVie Biotechnology Ltd.*, "Petitioners Request for Refund of Post Institution Fees," Case IPR2017-01008, U.S. Pat. No. 9,085,619, dated Nov. 29, 2017, 5 pages.
*Coherus Biosciences Inc.*, Petitioner v. *AbbVie Biotechnology Ltd.*, "Petitioners Request for Refund of Post Institution Fees," Case IPR2017-01009, U.S. Pat. No. 9,085,619, dated Nov. 29, 2017, 5 pages.

(56) References Cited

OTHER PUBLICATIONS

*Coherus Biosciences Inc.*, Petitioner v. *AbbVie Biotechnology Ltd.*, "Petition for *Inter Partes* Review of U.S. Pat. No. 9,085,619 to U.S.C. §§ 311-319 and 37 C.F.R. § 42," Case IPR2017-01008, U.S. Pat. No. 9,085,619, dated Mar. 2, 2017 81 pages.
*Coherus Biosciences Inc.*, Petitioner v. *AbbVie Biotechnology Ltd.*, "Petition for *Inter Partes* Review of U.S. Pat. No. 9,085,619 to U.S.C. §§ 311-319 and 37 C.F.R. § 42," Case IPR2017-01009, U.S. Pat. No. 9,085,619, dated Mar. 2, 2017 67 pages.
*Coherus Biosciences Inc.*, Petitioner v. *AbbVie Biotechnology Ltd.*, "Petition for *Inter Partes* Review," Case IPR2016-01018, U.S. Pat. No. 9,114,166, dated May 9, 2016.
*Coherus Biosciences Inc.*, Petitioner v. *AbbVie Biotechnology Ltd.*, "Petitioner's Power of Attorney in a Post Grant Proceeding Before the Patent Trial and Appeal Board," Case IPR2016-01018, U.S. Pat. No. 9,114,166, dated May 9, 2016, 2 pages.
*Coherus Biosciences Inc.*, Petitioner v. *AbbVie Biotechnology Ltd.*, "Petitioners for *Inter Partes* Review of U.S. Pat. No. 9,085,619," Case IPR2017-00827, U.S. Pat. No. 9,085,619, dated Jan. 31, 2017, 79 pages.
*Coherus Biosciences Inc.*, Petitioner v. *AbbVie Biotechnology Ltd.*, "Petitioners for *Inter Partes* Review of U.S. Pat. No. 9,085,619," Case IPR2017-00826, U.S. Pat. No. 9,085,619, dated Jan. 31, 2017, 63 pages.
*Coherus Biosciences Inc.*, Petitioner v. *AbbVie Biotechnology Ltd.*, "Petitioners Power of Attorney Pursuant to 37 CFR 42.10(b) for Petition for *Inter Partes* Review," Case IPR2017-00826, U.S. Pat. No. 9,085,619, dated Jan. 31, 2017, 2 pages.
*Coherus Biosciences Inc.*, Petitioner v. *AbbVie Biotechnology Ltd.*, "Petitioners Power of Attorney Pursuant to 37 CFR 42.10(b) for Petition for *Inter Partes* Review," Case IPR2017-00827, U.S. Pat. No. 9,085,619, dated Jan. 31, 2017, 2 pages.
*Coherus Biosciences Inc.*, Petitioner v. *AbbVie Biotechnology Ltd.*, "Petitioners Power of Attorney Pursuant to 37 CFR 42.10(b) for Petition for *Inter Partes* Review," Case IPR2017-01008, U.S. Pat. No. 9,085,619, dated Jan. 31, 2017, 2 pages.
*Coherus Biosciences Inc.*, Petitioner v. *AbbVie Biotechnology Ltd.*, "Petitioners Power of Attorney Pursuant to 37 CFR 42.10(b) for Petition for *Inter Partes* Review," Case IPR2017-01009, U.S. Pat. No. 9,085,619, dated Jan. 31, 2017, 2 pages.
*Coherus Biosciences Inc.*, Petitioner v. *AbbVie Biotechnology Ltd.*, "Petitioners Request for Refund of Post-Institution Fees," Case IPR2016-01018, U.S. Pat. No. 9,114,166, dated Mar. 2, 2017, 3 pages.
*Coherus Biosciences Inc.*, Petitioner v. *AbbVie Biotechnology Ltd.*, "Petitioners Request for Refund of Post-Institution Fees," Case IPR2017-00826, U.S. Pat. No. 9,085,619, dated May 25, 2017, 4 pages.
*Coherus Biosciences Inc.*, Petitioner v. *AbbVie Biotechnology Ltd.*, "Petitioners Unopposed Motion to Dismiss Petitions Without Prejudice," Case IPR2017-00826, U.S. Pat. No. 9,085,619, dated Apr. 7, 2017, 4 pages.
*Coherus Biosciences Inc.*, Petitioner v. *AbbVie Biotechnology Ltd.*, "Petitioners Unopposed Motion to Dismiss Petitions Without Prejudice," Case IPR2017-00827, U.S. Pat. No. 9,085,619, dated Apr. 7, 2017, 4 pages.
*Coherus Biosciences Inc.*, Petitioner v. *AbbVie Biotechnology Ltd.*, "Petitioners Updated Mandatory Notices," Case IPR2017-00826, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices," Case IPR2017-00827, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices," Case IPR2017-01008, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices," Case IPR2017-01009, U.S. Pat. No. 9,085,619, dated Mar. 23, 2017, 4 pages.
*Coherus Biosciences Inc.*, Petitioner v. *AbbVie Biotechnology Ltd.*, "Plaintiff Coherus Biosciences, Inc.'s Answer to Defendant Amgen Inc.'s Counterclaims," in the U.S. District Court for the District of Delaware, C.A. No. 19-139-RGA, Case IPR2016-01018, U.S. Pat. No. 9,114,166, dated Jun. 24, 2019.
*Coherus Biosciences Inc.*, Petitioner v. *AbbVie Biotechnology Ltd.*, "Plaintiff Coherus Biosciences, Inc.'s First Amended Complaint," in the U.S. District Court for the District of Delaware, C.A. No. 19-139-RGA, Case IPR2016-01018, U.S. Pat. No. 9,114,166, dated Mar. 5, 2019.
*Coherus Biosciences Inc.*, Petitioner v. *AbbVie Biotechnology Ltd.*, "Plaintiff Coherus Complaint" filed in the U.S. District Court for the District of Delaware, C.A. No. 19-139-RGA, Case IPR2016-01018, U.S. Pat. No. 9,114,166, dated Jan. 24, 2019.
*Coherus Biosciences Inc.*, Petitioner v. *AbbVie Biotechnology Ltd.*, "Request for Rehearing in *Inter Partes* Review," Case IPR2016-01018, U.S. Pat. No. 9,114,166, dated Dec. 2, 2016.
*Coherus Biosciences Inc.*, Petitioner v. *AbbVie Biotechnology Ltd.*, "Decision Denying Institution of *Inter Partes* Review," Case IPR2017-01008, U.S. Pat. No. 9,085,619, dated Sep. 7, 2017, 26 pages.
*Coherus Biosciences Inc.*, Petitioner v. *AbbVie Biotechnology Ltd.*, Patent Owner, "Decision Denying Institution of *Inter Partes* Review 37 C.F.R. § 42.108," filed Sep. 7, 2017, 25 pages. [Case IPR2017-00822, U.S. Pat. No. 9,085,619].
*Coherus Biosciences Inc.*, Petitioner v. *AbbVie Biotechnology Ltd.*, Patent Owner, "Decision Denying Institution of Inter Partes Review 37 C.F.R. § 42.108," filed Sep. 7, 2017, 16 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.," dated Apr. 3, 2017, 95 pages. [Case IPR2017-00822, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.," dated Apr. 3, 2017, 99 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.," dated Jan. 30, 2016, 95 pages. [Case IPR2017-00822, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.," dated Jan. 30, 2017, 99 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Mark C. Manning, Ph.D.," dated May 6, 2016, 163 pages. [Case IPR2017-00822, U.S. Pat. No. 9,085,619].
*Coherus Biosciences Inc.*, Petitioner v. *AbbVie Biotechnology Ltd.*, Patent Owner, "Notice of Filing Date Accorded to Petition and Time for Filing Patent Owner Preliminary Response," Case IPR2017-00822, U.S. Pat. No. 9,085,619, dated Feb. 24, 2017, 5 pages.
*Coherus Biosciences Inc.*, Petitioner v. *AbbVie Biotechnology Ltd.*, Patent Owner, "Notice of Filing Date Accorded to Petition and Time for Filing Patent Owner Preliminary Response," Case IPR2017-00823, U.S. Pat. No. 9,085,619, dated Feb. 24, 2017, 5 pages.
*Coherus Biosciences Inc.*, Petitioner v. *AbbVie Biotechnology Ltd.*, Patent Owner, "Notice of Refund," Case IPR2017-00822, U.S. Pat. No. 9,085,619, dated Dec. 1, 2017, 2 pages.
*Coherus Biosciences Inc.*, Petitioner v. *AbbVie Biotechnology Ltd.*, Patent Owner, "Notice of Refund," Case IPR2017-00823, U.S. Pat. No. 9,085,619, dated Dec. 1, 2017, 2 pages.
*Coherus Biosciences Inc.*, Petitioner v. *AbbVie Biotechnology Ltd.*, Patent Owner, "Order Conduct of the Proceeding 37 C.F.R. § 42.5," filed Apr. 7, 2017, 6 pages. [Case IPR2017-00822, Case IPR2017-00823, Case IPR2017-00826, Case IPR2017-00827, Case IPR2017-01008, Case IPR2017-01009 U.S. Pat. No. 9,085,619].
*Coherus Biosciences Inc.*, Petitioner v. *AbbVie Biotechnology Ltd.*, Patent Owner, "Patent Owner's Preliminary Response," filed Jun. 11, 2017, 58 pages. [Case IPR2017-00822, U.S. Pat. No. 9,085,619].
*Coherus Biosciences Inc.*, Petitioner v. *AbbVie Biotechnology Ltd.*, Patent Owner, "Patent Owner's Preliminary Response," Case IPR2016-01018, U.S. Pat. No. 9,114,166, dated Aug. 9, 2016, 77 pages.

(56) References Cited

OTHER PUBLICATIONS

*Coherus Biosciences Inc.*, Petitioner v. *AbbVie Biotechnology Ltd.*, Patent Owner, "Patent Owner's Mandatory Notices," Case IPR2017-00822, U.S. Pat. No. 9,085,619, dated Feb. 21, 2017, 6 pages.

*Coherus Biosciences Inc.*, Petitioner v. *AbbVie Biotechnology Ltd.*, Patent Owner, "Patent Owner's Mandatory Notices," Case IPR2017-00823, U.S. Pat. No. 9,085,619, dated Feb. 21, 2017, 6 pages.

*Coherus Biosciences Inc.*, Petitioner v. *AbbVie Biotechnology Ltd.*, Patent Owner, "Patent Owner's Power of Attorney," Case IPR2017-00822, U.S. Pat. No. 9,085,619, dated Feb. 21, 2017, 2 pages.

*Coherus Biosciences Inc.*, Petitioner v. *AbbVie Biotechnology Ltd.*, Patent Owner, "Patent Owner's Power of Attorney," Case IPR2017-00823, U.S. Pat. No. 9,085,619, dated Feb. 21, 2017, 2 pages.

*Coherus Biosciences Inc.*, Petitioner v. *AbbVie Biotechnology Ltd.*, Patent Owner, "Patent Owner's Preliminary Response," filed Jun. 11, 2017, 48 pages. [Case IPR2017-00823,U.S. Pat. No. 9,085,619].

*Coherus Biosciences Inc.*, Petitioner v. *AbbVie Biotechnology Ltd.*, Patent Owner, "Patent Owner's Second Updated Mandatory Notices," Case IPR2017-00823, U.S. Pat. No. 9,085,619, dated Mar. 17, 2017, 5 pages.

*Coherus Biosciences Inc.*, Petitioner v. *AbbVie Biotechnology Ltd.*, Patent Owner, "Patent Owner's Updated Mandatory Notices," Case IPR2017-00822, U.S. Pat. No. 9,085,619, dated Mar. 23, 2017, 4 pages.

*Coherus Biosciences Inc.*, Petitioner v. *AbbVie Biotechnology Ltd.*, Patent Owner, "Patent Owner's Updated Mandatory Notices," Case IPR2017-00823, U.S. Pat. No. 9,085,619, dated Feb. 27, 2017, 4 pages.

*Coherus Biosciences Inc.*, Petitioner v. *AbbVie Biotechnology Ltd.*, Patent Owner, "Petition for *Inter Partes* Review of U.S. Pat. No. 9,085,619 Pursuant to 35 U.S.C. §§ 311-319 and 37 C.F.R. § 42," Jan. 31, 2017, 57 pages. [Case IPR2017-00822, U.S. Pat. No. 9,085,619].

*Coherus Biosciences Inc.*, Petitioner v. *AbbVie Biotechnology Ltd.*, Patent Owner, "Petition for *Inter Partes* Review of U.S. Pat. No. 9,085,619 Pursuant to 35 U.S.C. §§ 311-319 and 37 C.F.R. § 42," Jan. 31, 2017, 64 pages. [Case IPR2017-00823, U.S. Pat. No. 9,085,619].

*Coherus Biosciences Inc.*, Petitioner v. *AbbVie Biotechnology Ltd.*, Patent Owner, "Petitioner's Power of Attorney Pursuant to CFR 42.10(b) for Petition for *Inter Partes* Review," Case IPR2017-00822, U.S. Pat. No. 9,085,619, dated Jan. 31, 2017, 2 Pages.

*Coherus Biosciences Inc.*, Petitioner v. *AbbVie Biotechnology Ltd.*, Patent Owner, "Petitioner's Power of Attorney Pursuant to CFR 42.10(b) for Petition for *Inter Partes* Review," Case IPR2017-00823, U.S. Pat. No. 9,085,619, dated Jan. 31, 2017, 2 Pages.

*Coherus Biosciences Inc.*, Petitioner v. *AbbVie Biotechnology Ltd.*, Patent Owner, "Petitioner's Request for Refund of Post-Institution Fee No. 2," Case IPR2017-00822, U.S. Pat. No. 9,085,619, dated Nov. 29, 2017, 5 pages.

*Coherus Biosciences Inc.*, Petitioner v. *AbbVie Biotechnology Ltd.*, Patent Owner, "Petitioner's Request for Refund of Post-Institution Fee," Case IPR2017-00822, U.S. Pat. No. 9,085,619, dated Nov. 29, 2017, 5 pages.

*Coherus Biosciences Inc.*, Petitioner v. *AbbVie Biotechnology Ltd.*, Patent Owner, "Petitioner's Request for Refund of Post-Institution Fee," Case IPR2017-00823, U.S. Pat. No. 9,085,619, dated Nov. 29, 2017, 5 pages.

*Coherus Biosciences Inc.*, Petitioner v. *AbbVie Biotechnology Ltd.*, Patent Owner, "Petitioner's Updated Mandatory Notices," Case IPR2017-00823, U.S. Pat. No. 9,085,619, dated Mar. 23, 2017, 4 pages.

*Coherus Biosciences Inc.*, Petitioner v. *AbbVie Biotechnology Ltd.*, Patent Owner, "Replacement Petition for *Inter Partes* Review of U.S. Pat. No. 9,085,619 Pursuant to 35 U.S.C. §§ 311-319 and 37 C.F.R. § 42," filed Apr. 10, 2017, 58 pages. [Case IPR2017-00822, U.S. Pat. No. 9,085,619].

*Coherus Biosciences Inc.*, Petitioner v. *AbbVie Biotechnology Ltd.*, Patent Owner, "Replacement Petition for *Inter Partes* Review of U.S. Pat. No. 9,085,619 Pursuant to 35 U.S.C. §§ 311-319 and 37 C.F.R. § 42," Apr. 10, 2017, 65 pages. [Case IPR2017-00823, U.S. Pat. No. 9,085,619].

*Coherus Biosciences Inc.*, Petitioner v. *AbbVie Biotechnology Ltd.*, Patent Owner, "Declaration of Mark C. Manning, Ph.D.," Exhibit 1002 filed with Petition for *Inter Partes* Review of U.S. Pat. No. 9,114,166, filed May 6, 2016, 163 pages.

*Coherus Biosciences Inc.*, Petitioner v. *AbbVie Biotechnology Ltd.*, Patent Owner. "Patent Owner's Second Updated Mandatory Notices," Case IPR2017-00822, U.S. Pat. No. 9,085,619, dated Mar. 17, 2017, 5 pages.

*Coherus Biosciences Inc.*, Petitioner v. *AbbVie Biotechnology Ltd.*, Patent Owner. "Patent Owner's Updated Mandatory Notices," Case IPR2017-00822, U.S. Pat. No. 9,085,619, dated Feb. 27, 2017, 4 pages.

*Coherus Biosciences Inc.*, Petitioner v. *AbbVie Biotechnology Ltd.*, Patent Owner. "Patent Owner's Updated Mandatory Notices," Case IPR2017-00822, U.S. Pat. No. 9,085,619, dated Jun. 11, 2017, 4 pages.

*Coherus Biosciences Inc.*, Petitioner v. *AbbVie Biotechnology Ltd.*, Patent Owner. "Patent Owner's Updated Power of Attorney," Case IPR2017-00822, U.S. Pat. No. 9,085,619, dated Jun. 7, 2017, 4 pages.

Coherus Biosciences, Inc., "Third Amended and Restated Investor Rights Agreement," May 9, 2014, 68 pages.

Communication from Elkington and Fife LLP regarding European Patent Application No. 12481765.6, 2015, 3 pages.

CVS/Caremark™ Performance Drug List, Oct. 2015, 10 pages.

D82 from Opposition of EP 1528933, Filed by AbbVie on Feb. 26, 2016 (CAS Registry for Adalimumab), 6 pages.

Daughertry and Mrsny, "Formulation and Delivery Issues for Monoclonal Antibody Therapeutics," Advanced Drug Delivery Reviews 58:686-706, 2006.

Dean, "Lange's Handbook of Chemistry," McGraw-Hill, p. 8.49, 8.65 (9th ed. 1999).

Decision in Opposition Proceedings Revoking EP 1528933 B1, Sep. 9, 2015.

Dobrow, "DTC Report—DTC Gets Smart," Medical Marketing & Media, URL <http://www.mmm-online.com/dtc-report-dtc-gets-smart/printarticle/339357/>, retrieved on Apr. 1, 2014, 5 pages.

Dobrow, "MM&M 2014 Large Pharma Marketing Team of the Year: HUMIRA," Medical Marketing & Media, URL < http://www.mmm-online.com/mmm-2014-large-pharma-marketing-team-of-the-year-humira.htm>, retrieved on Jan. 1, 2014, 2 pages.

Douglas D. Banks et al., "Native-State Solubility and Transfer Free Energy as Predictive Tools for Selecting Excipients to Include in Protein Formulation Development Studies," 101 J. Pharm. Sci. 2720 (2012).

DrugBank: Adalimumab. www.drugbank.ca/drugs/DB00051, Last Visited May 5, 2016, 15 pages.

Edward C. Keystone et al., "Golimumab, a Human Antibody to Tumor Necrosis Factor-α Given by Monthly Subcutaneous Injections, in Active Rheumatoid Arthritis Despite Methotrexate: The Go-Forward Study," 68 Ann. Rheum. Dis. 789 (2009).

Emily Ha, et al., "Peroxide Formation inPolysorbate 80 and Protein Stability," 91 J. Pharm. Sci. 2252 (2002).

Employee Profiles, Legacy BioDesign LLC Webpage, 2 pages, 2019.

Enbrel (etanercept), FDA Arthritis Advisory Committee, Aug. 17, 2001, Immunex Corporation and Wyeth-Ayerst Laboratories, 55 pages.

Enbrel® Label (Nov. 1998).

Enbrel® Label (Sep. 2002).

Enbrel® Summary Basis of Approval (1998).

Esbenshade et al., "Pharmacological and behavioral properties of A-349821, a selective and potent human histamine H3 receptor antagonist," Biochemical Pharmacology 68(5):933-945, 2004.

Eurasian Office Action in Eurasion Appln. No. 201590518, dated Mar. 10, 2016, 5 pages.

European Search Report (extended) in European Appln. No. 13835291, dated Mar. 15, 2016, 6 pages.

(56) References Cited

OTHER PUBLICATIONS

Eva Y. Chi et al., "Physical Stability of Proteins in Aqueous Solution: Mechanism and Driving Forces in Nonnative Protein Aggregation," 20 Pharm. Res. 1325 (2003).
Ewert et al., "Biophysical Properties of Human Antibody Variable Domains," J. Mo. Biol. 325:521-553, 2003.
Exhibit D filed with Coherus Complaint filed in the U.S. District Court for the District of Delaware, C.A. No. 19-139 (RGA) dated Jan. 24, 2019, 13 pages.
Exhibit D filed with Plaintiff Coherus Biosciences, Inc.'s First Amended Complaint in the U.S. District Court for the District of Delaware, C.A. No. 19-139 (RGA) dated Mar. 5, 2019, 78 pages.
Exhibit E filed with Coherus Complaint filed in the U.S. District Court for the District of Delaware, C.A. No. 19-139 (RGA) dated Jan. 24, 2019, 121 pages.
Exhibit E filed with Plaintiff Coherus Biosciences, Inc.'s First Amended Complaint in the U.S. District Court for the District of Delaware, C.A. No. 19-139 (RGA) dated Mar. 5, 2019, 13 pages.
Exhibit F filed with Plaintiff Coherus Biosciences, Inc.'s First Amended Complaint in the U.S. District Court for the District of Delaware, C.A. No. 19-139 (RGA) dated Mar. 5, 2019, 121 pages.
Exhibit G filed with Plaintiff Coherus Biosciences, Inc.'s First Amended Complaint in the U.S. District Court for the District of Delaware, C.A. No. 19-139 (RGA) dated Mar. 5, 2019, 112 pages.
Fayos et al., "On the Origin of the Thermostabilization of Proteins Induced by Sodium Phosphate," JACS Communications dated Mar. 3, 2005, 2 pages.
FDA, "What are 'Biologics'? Questions and Answers," (Feb. 6, 2018, https://www.fda.gov/about-fda/center-biologics-evaluation-and-research-cber/what-are-biologics-questions-and-answers, 1 page.
fda.gov [online], "Privigen®, Immune Globulin Intravenous (Human), 10% Liquid Initial," U.S. Approval: 2007, Retrieved from: https://www.fda.gov/files/vaccines%2C%20blood%20%26%20biologics/published/Package-Insert---Privigen.pdf, 7 pages.
Filing in Support of Opposition Against EP 1324776 B1, Filed Jun. 16, 2010.
Flebogamma® Label (Jan. 2004).
Fransson & Espander-Jansson, "Local Tolerance of Subcutaneous Injections," J. Pharm. Pharmacol. 48:1012-1015 (1996).
Frenken et al., "Identification of the Component Part in an Epoetin Alfa Preparation that Causes Pain after Subcutaneous Injection," American J. of Kidney Diseases 22(4):553-556 (1993).
Frokjaer et al., eds., "Pharmaceutical Formulation Development of Peptides and Proteins," Taylor & Francis: London, 2000.
Gamimune® Label (Oct. 2005).
Gammagard Liquid Label (Apr. 2005).
Gamunex® Label (Nov. 2005).
Gatlin et al., "Formulation and Administration Techniques to Minimize Injection Pain and Tissue Damage Associated with Parenteral Products," Injectable Drug Development: Techniques to Reduce Pain and Irritation, pp. 401-425, 1999.
Gebhart, "Biotech company preparing several drugs for takeoff," Drug Topics, vol. 145, No. 5, p. 50, 2001.
Gelfand, "Differences between IGIV products: Impact on clinical outcome," International Immunopharmacology 6:592-599, 2006.
Gennaro, ed., "Remington: The Science and Practice of Pharmacy," 20th ed., Solutes, pp. 785-786, 2000.
Gilbert and Cothran, "SC versus IV delivery: Reducing costs while increasing patient satisfaction," Hemotology & Oncology News & Issues, Dec. 2005, pp. 25-29.
Gloff et al., "Pharmacokinetics & Protein Therapeutics," Advanced Drug Delivery Reviews, 4 (1990) pp. 359-386.
Gokarn et al., "Excipients for Protein Drugs," Ch. 17 in Excipient Development for Pharmaceutical, Biotechnology, and Drug Delivery Systems (Ashok Katdare & Mahe sh V. Chaubal eds., 2006).
Gokarn et al., "Self-buffering antibody formulations," J. of Pharm. Sci., vol. 97, No. 8, pp. 3051-3066, 2008.
Golimumab/Simponi® label (Revised Dec. 2011).
Goolcharran et al., "The Effects of a Histidine Residue on the C-Terminal Side of an Asparaginyl Residue on the Rate of Deamidation Using Model Pentapeptides," J. of Pharmaceutical Sciences, vol. 89, Issue 6, pp. 818-825, 2000.
Gottlieb et al., "Efficacy and Safety of Anti-TNF-Agents in Psoriasis," Anti-TNF-Therapies in the Treatment of Dermatologic Diseases, Skin & Allergy News, 11 pages, 2005.
Granolleras et al., "Experience of pain after subcutaneous administration of different preparations of recombinant human erythropoietin: a randomized, double-blind crossover study," vol. 36, No. 6, pp. 294-298, 1991.
Guidance for Industry, "Clinical Development Programs for Drugs, Devices and Biological Products for the Treatment of Rheumatoid Arthritis" (1999).
Gura, "The Art of Entrepreneurship," Science Translational Medicine, vol. 346 Issue 6213, p. 1146, Nov. 27, 2014.
Ha et al., "Peroxide Formation in Polysorbate 80 and Protein Stability," J. Pharm. Sci. 91:2252-2264, 2002.
Hanauer, Gastroenterology, vol. 130, p. 323-333 (Feb. 2006).
Handbook of Pharmaceutical Excipients, Pharmaceutical Press (Raymond C. Rowe, Paul J. Sheskey, & Sian C. Owen eds., 5th ed. 2006).
Hanna, K., "Tolerability of a New Intravenous Immunoglobulin Preparation (IGIV) in Pediatric and Adult Patients," Presented at the 60th Anniversary Meeting of the American Academy of Allergy, Asthma & Immunology, Mar. 10, 2003, J. Allergy Clinical Immunology, vol. 111, No. 2, Part 2, a631, 2 pages.
Harris et al., "Commerical Manufacturing Scale Formulation and Analytical Characterization of Therapeutic Recombinant Antibodies," Drug Development Research, 61:137-154, 2004.
Hawe et al., "Taylor Dispersion Analysis Compared to Dynamic Light Scattering for the Size Analysis of Therapeutic Peptides and Proteins and Their Aggregates," Pharm. Res. 28:2302-2310, May 2011.
Helms et al., "Destabilizing loop swaps in the CDRs of an immunoglobulin VL domain," Protein Science, dated Aug. 3, 1995, 9 pages.
Hendrickson, "Birth of a Blockbuster: Abbott Mounts Humira's Marketing Campaign," Boston Business Journal Article (Oct. 20, 2003), Last Accessed Mar. 25, 2016.
HepaGam B™, Summar Basis for Approval, Jan. 2006, 12 pages.
Humira, product information sheet, p. 1-16, 2002, Abbott Lab.
Humira.com [online], "Injection Assistance," Humira®, Mar. 2005, [retrieved on Jan. 12, 2017], Retrieved from the Internet URL: http://web.archive.org/web/20050317083331/http://www.humira.com/hu/hustore/cgibin/ProdSubEV_Cat_205043_SubCat_210170_NavRoot_205042_NavID_301.htm, 2 pages.
Humira® Label (Feb. 2007).
Humira® Label (Feb. 2008).
Humira® Label (Jan. 2003).
Humira® Label (Jan. 2008).
Humira® Label (Nov. 2006).
Humira® Label (Oct. 2005).
Humira® Label (Sep. 2007).
Humira® Label, Nov. 2015.
Humira® Label (Oct. 2016).
HumiraTM (adalimumab) pamphlet, Dec. 20, 2002.
Humphreys, Top 200 Medicines—Special Report, pharmalive.com, URL <http://www.pharmalive.com/special-report-top-200-medicines/> 5 pages, 2015.
Indian Office Action in Application No. 806/KOLNP/2015, dated Nov. 15, 2019, 6 pages.
Infliximab/Remicade® label (Nov. 1999).
International Preliminary Report on Patentability in International Appln. No. PCT/US2013/58618, dated Mar. 10, 2015, 10 pages.
International Search Report in International Appln. No. PCT/US2013/58618, dated Apr. 28, 2014, 4 pages.
Israel Office Action in Israeli Appln. No. 2336545, dated Jan. 21, 2018, 5 pages (w/ English Translation).
Japanese Office Action in Japanese Appln. No. 2015-531261, dated Apr. 25, 2018, 6 pages (with machine translation).
Japanese Office Action in Japanese Appln. No. 2015-531261, dated Jun. 21, 2017, 15 pages (with machine translation).
Jefferis et al., "Recognition Sites on Human IgG for Fcy Receptors: The Role of Glycosylation," Immunology Letters 44:111-117 (1995).

(56) References Cited

OTHER PUBLICATIONS

Jenny M. Phillips, "Manufacture and Quality Control of CAMPATH-1 Antibodies for Clinical Trials," 3 Cytotherapy 233 (2001).

John F. Carpenter, et al., Chapter 7: Freezing- and Drying-Induced Perturbations of Protein Structure and Mechanisms of Protein Protection by Stabilizing Additives, in Freeze-Drying/L Yophiliza Tion of Pharmaceutical and Biological Products 167 (2d ed. 2004).

John F. Carpenter, et al., "Inhibition of Stress-Induced Aggregation of Protein Therapeutics," 309 Methods in Enzymology 236 (1999).

John F. Carpenter et al., "Rational Design of Stable Lyophilized Protein Formulations: Some Practical Advice," Pharm. Res. 14(8):969 (1997).

Jones, "Analysis of polypeptides and proteins," Adv. Drug Delivery Rev. 10:29-90, 1993.

Jorgensen et al., "Pain Assessment of Subcutaneous Injections," Ann. Pharma., 30(7/8), 729-732, 1996.

Jose Baselga et al., "Phase II Study of Weekly Intravenous Recombinant Humanized Anti-p185HER2 Monoclonal Antibody in Patients with HER2/neu-overexpressing Metastatic Breast Cancer," 14 J. Clin. Oncol. 738 (1996).

Joseph M. Perchiacca et al., "Engineering Aggregation-Resistant Antibodies," 3 Annu. Rev. Chem. Biomol. Eng. 263 (2012).

Kamerzell et al., "Increasing IgG Concentration Modulates the Conformational Heterogeneity and Bonding Network that Influence Solution Properties," J. Phys. Chem. B, 113, dated Mar. 6, 2009, 10 pages.

Karow et al., "Buffer capacity of biologics—from buffer salts to buffering by antibodies," Biotechnol. Prog., vol. 29, No. 2, pp. 480-492, 2013.

Katdare et al., "Excipient Development for Pharmaceutical, Biotechnology, and Drug Delivery Systems," Taylor & Francis Group, LLC, year 2006, 43 pages.

Kavanaugh et al., "Treatment with Adalimumab (D2E7) does not Affect Normal Immune Responsiveness," Arthritis & Rheumatism, September 46(9):S132, 2002.

Kaymakcalan et al., "Development of a Fully Human Anti-TNF Monoclonal Antibody," J. Interferon & Cytokine Research, Abstract 6.16, 18(5):A-125, May 1998.

Kempeni, "Preliminary results of early clinical trials with the fully human anti-TNFα monoclonal antibody D2E7," Ann Rheum Dis, 58:(Suppl I), I70-I72, 1999.

Keystone et al., "Adalmumab (D2E7), A Fully Human Anti-TNF-α Monoclonal Antibody, Inhibits the Progression of Structural Joint Damage in Patients with Active RA Despite Doncomitant Methotrexate Therapy," Arthritis & Rheumatism 46(9):S205, Sep. 2002.

Keystone et al., "Golimumab, a human antibody to tumour necrosis factor α given by monthly subcutaneous injections, in active rheumatoid arthritis despite methotrexate therapy: the Go-Forward Study," Ann. Rheum. Dis. 68:789-796, 2009.

Keystone et al., "The Fully Human Anti-TNF Monoclonal Antibody, Adalimumab (D2E7), Dose Ranging Study: The 24-Week Clinical Results in Patients with Active RA on Methotrexate Therapy (The Armada Trial)," Ann. Eur. Congr. Rheumatol., Abstract OP0086, Jun. 13-16, 2001.

King, "The Best Selling Drugs of All Time, Humira Joins the Elite," Forbes, Jan. 28, 2013, 4 pages.

Krishnamurthy et al., "The Stability Factor: Importance in Formulation Development," Curr. Pharm. Biotech 3:361-371, 2002.

Krishnan et al., "Development of Formulations for Therapeutic Monoclonal Antibodies and FC Fusion Proteins," Formulation and Process Development Strategies for Manufacturing Biopharmaceuticals, 2010, pp. 383-427.

Larry R. Helms, et al., "Destabilizing Loop Swaps in the CDRs of an Immunoglobulin VL Domain," 4 Protein Sci. 2073 (1995).

Laursen et al., "Pain Perception after Subcutaneous Injections of Media Containing Different Buffers," Basic & Clinical Pharmacology & Toxicology 98:218-221 (2006).

Lene Jorgensen et al., "Recent Trends in Stabilising Peptides and Proteins in Pharmaceutical Formulation—Considerations in the Choice of Excipients," 6 Expert Opin. Drug Deliv. 1219 (2009).

Levine et al., "The Use of Surface Tension Measurements in the Design of Antibody-Based Product Formulations," J. Parenteral Sci. & Tech. 45(3):160-165, May/Jun. 1991.

Liu et al., "Reversible Self-Association Increases the Vicosity of a Concentrated Monoclonal Antibody in Aqueous Solution," published online in Wiley InterScience, dated Feb. 2005, 13 pages.

Lorenz, "Technology evaluation: Adalimumab, Abbott Laboratories," Current Opinion in Molecular Therapeutics 4(2):185-190, 2002.

Maggio, "Use of excipients to control aggregation in peptide and protein formulations," J. Excipients and Food Chem. 1(2):40-49, Aug. 2010.

Manning et al., "Stability of Protein Pharmaceuticals," Pharm. Res. 6(11):903-918, 1989.

Marco van de Weert & Theodore W. Randolph, Chapter 6: Physical Instability of Peptides and Proteins, in Pharmaceutical Formulation Development of Peptides and Proteins 107 (2012).

Masako Ohnishi & Hiromichi Sagitani, "The Effect of Nonionic Surfactant Structure on Hemolysis," 70 J. Am. Oil Chemists' Soc'y 679 (1993).

Matteson et al., "Treatment of active refractory rheumatoid arthritis with humanized monoclonal antibody CAMPATH-1H administered by daily subcutaneous injection," Arthritis & Rheumatism, 38(9):1187-1193, 1995.

McCue et al., "Three Generations of Immunoglobulin G Preparations for Clinical Use," Reviews of Infectious Diseases, vol. 8, Sup. 4, pp. s374-s381, 1986.

McDonnell, "Production of Antibodies in Hybridoma and Non-hybridoma Cell Lines," Ch. 3 in Animal Cell Culture, Cell Engineering 9, pp. 65-88, (ed. M. Al-Rubeai, 2015).

Meadows and Hollowell, "'Off-label' drug use: an FDA regulatory term, not a negative implication of its medical use," Int. J. Impotence Research 20:135-144, 2008.

Mezzasalma et al., "Enhancing Recombinant Protein Quality and Yield by Protein Stability Profiling," Journal of Biomolecular Screening 12(3); year 2007, 11 pages.

Michael J. Treuheit et al., "Inverse Relationship of Protein Concentration and Aggregation," 19 Pharm. Res. 511 (2002).

Nabuchi et al., "The Stability and Degradation Pathway of Recombinant Human Parathyroid Hormone: Deamidation of Asparaginyl Residue and Peptide Bond Cleavage at Aspartyl and Asparaginyl Residues," Pharmaceutical Research, vol. 14 Issue 12, pp. 1685-1690, 1997.

Nail et al., "Development and Manufacture of Protein Pharmaceuticals," Kluwer Academic I Plenum Publishers, year 2002, 82 pages.

Napke et al., "Excipients and additives: hidden hazards in drug products and in product substitution," Can. Med. Assoc. J., vol. 131, pp. 1449-1452, 1984.

Nash et al., "Randomized Crossover Comparison of Injection Site Pain with 40 mg/0.4 or 0.8mL Formulations of Adalimumab in Patients with Rheumatoid Arthritis," Rheu. Ther. 3:257-270, 2016.

Nema et al., "Excipients and Their Use in Injectable Products," FDA J. Pharm. Sci. & Tech, 51(4), pp. 166-171, Jul./Aug. 1997.

Nozaki & Tanford, "Examination of Titration Behavior," Methods Enzymol. 11:715-734 (1967).

Octagam® Label (Mar. 2007).

Octagam® Label (Mar. 2004).

Olthuis et al., "Characterization of Proteins by Means of their Buffer Capacity, Measured With and ISFET-Based Coulometric Sensor-Actuator System," Biosensors & Bioelectronics, Year 1994, 9 pages.

Olthuis et al., "Characterization of Proteins by Means of their Buffer Capacity, Measured with an ISFET-based Coulometric Sensor-Actuator System," Biosensors & Bioelectronics, 9:743-751 (1994).

Paborji et al., "Chemical and Physical Stability of Chimeric L6, a Mouse-Human Monoclonal Antibody," Pharmaceutical Research, vol. 11, Issue 5, pp. 764-771 (1994).

Parslow, "Immunoglobulins & Immunoglobulin Genes," Ch. 7 in Medical Immunology, Appleton & Lange (Daniel P. Stites, Abba I. Terr, & Tristram G. Parslow eds., 9th ed. 1997).

Patel et al., "Chemical Pathways of Peptide Degradation. II. Kinetics of Deamidation of an Asparaginyl Residue in a Model Hexapeptide," Pharmaceutical Research, vol. 7, Issue 7, pp. 703-711, 1990.

(56) References Cited

OTHER PUBLICATIONS

Patent Term Extension Application Salfeld '382 Patent filed with Petition for *Inter Partes* Review of U.S. Pat. No. 9,114,166, filed May 9, 2019, 2 pages.
Perkins et al., "Determination of the Origin of Charge Heterogeneity in a Murine Monoclonal Antibody," Pharmaceutical Research, vol. 17, Issue 9, pp. 1110-1117, 2000.
Phillips et al., "Manufacture and quality control of CAMPATH-1 antibodies for clinical trials," Cytotherapy 3(3):233-242, 2001.
Physicians' Desk Reference entry for Gamimune N, 5%, pp. 925-928, 56th edition, 2002, 6 pages.
Physicians' Desk Reference entry for Gamunex, pp. 872-876, 59th edition, 2005.
Physicians' Desk Reference, 56th ed., pp. 558-559, 914-931, 805-807, 2026-2028, 2295-2297, 2524-2525, 33 pages, 2002.
Physicians' Desk Reference, 58th edition, pp. 470-474, Humira Label 2003, 2004.
Physicians' Desk Reference, 56th ed., 2002, pp. 1178-1182.
Physicians' Desk Reference, 56th ed., 2002, pp. 1414-1417.
Physicians' Desk Reference, 56th ed., 2002, pp. 1428-1430, 1750-1752.
Physicians' Desk Reference, 56th ed., 2002, pp. 1958-1962.
Physicians' Desk Reference, 56th ed., 2002, pp. 2028-2029.
Physicians' Desk Reference, 56th ed., 2002, pp. 2297-2299.
Physicians' Desk Reference, 56th ed., 2002, pp. 2399-2401.
Physicians' Desk Reference, 56th ed., 2002, pp. 2498-2502.
Physicians' Desk Reference, 56th ed., 2002, pp. 3046-3047.
Physicians' Desk Reference, 56th ed., 2002, pp. 992-995.
Physicians' Desk Reference, 56th ed., pp. 582-592, 988-991, 1434-1437, 1752-1760, 1772-1774, 1930-1934, 2502-2507, 3140-3142, (2002).
Physicians' Desk Reference, 56th ed., pp. 914-915, 917-919, 925-931, 992-995, 1178-1182, 1414-1417, 1428-1430, 1752-1755, 1958-1962, 2028-2029, 2295-2297, 2498-2052, 3046-3047 (2002).
Physicians' Desk Reference, 56th ed., pp. 925-928, 2002.
Physicians' Desk Reference, 56th ed., Suppl. A, pp. A4-A9, (2002).
Physicians' Desk Reference, 57th ed., Suppl. A, pp. A64-A67, A84-A88, (2003).
Preliminary Ruling in Opposition Proceedings Revoking EP 1528933 B1, Oct. 22, 2014.
Press Release, "Amgen and Immunomedics Announce Emphasis on Development of AMG 412 (Epratuzumab) as Combination Therapy While Closing Single Agent Trial," PRNewswire—FirstCall, Jan. 2003, 2 pages.
Privigen® Label (Jul. 2007).
Privigen® Label, Oct. 2016, 7 pages.
Prosecution History of U.S. Appl. No. 15/799,851 Reply to Final Office Action, filed Sep. 18, 2018, 102 pages.
Prosecution History of U.S. Appl. No. 15/799,851, Notice of Allowance, dated Oct. 18, 2018, 7 pages.
U.S. Appl. No. 60/690,582, filed Jun. 14, 2005.
Q1 2016 Coherus Biosciences Earnings Call, May 9, 2016, 13 pages.
Raibekas et al., "Anion Binding and Controlled Aggregation of Human Interleukin-1 Receptor Antagonist," Biochemistry, 44, dated May 15, 2005, 9 pages.
Rau et al. in Annals of Rheumatic Diseases, XIV European League Against Rheumatism Congress, 1999, Abstract 907, "Effective Combination of the Fully Human Anti-TNF Antibody D2E7 and Methotrexate in Active Rheumatoid Arthritis," p. 217.
Rau et al., "Long-Term Efficacy and Tolerability of Multiple I.V. Doses of the Fully Human Anti-TNF-Antibody D2E7 in Patients with Rheumatoid Arthritis," Arthritis Rheum. 41(9):S55, Sep. 1998.
Remicade® Label (Aug. 1998).
Remicade® Summary Basis of Approval (1999).
Richard Gonzalez, PowerPoint by AbbVie CEO, "AbbVie Long-Term Strategy," Oct. 30, 2015, 33 pages.

Ritzel et al., "Pharmacokinetic, insulinotropic, and glucagonostatic properties of GLP-1 [7-36 amide] after subcutaneous injection in healthy volunteers. Dose-response relationships," Diabetologia 38:720-725, 1995.
Robert G. Hamilton, The Human IGG Subclasses (2001).
Robert Ritzel et al., "Pharmacokinetic, Insulinotropic, and Glucagonostatic Properties of GLP-1 [7-36 amide] after Subcutaneous Injection in Healthy Volunteers. Dose-response-relationships," 38 Diabetologia 720 (1995).
Rouet et al., "Stability engineering of the human antibody repertoire," FEBS Letters 588, dated Nov. 28, 2013, 9 pages.
Ruiz et al., "Aggregation of Recombinant Human Interferon Alpha 2b in Solution: Technical Note," AAPS PharmSciTech; 7(4) Article 99, dated Dec. 22, 2006, 5 pages.
Sampathkumar Krishnan, et al., "Chapter 16: Development of Formulations for Therapeutic Monoclonal Antibodies and Fc Fusion Proteins," in Formulation and Process Development Strategies for Manufacturing Biopharmaceuticals 383 (2010).
Santora et al, "Characterization of Recombinant human Monoclonal Tissue Necrosis Factor-a Antibody Using Cation-Exchange HPLC and Capillary Isoelectric Focusing," Anal. Biochem. 275, pp. 98-108, 1999.
Schattenkirchner et al., "Efficacy and Tolerability of Weekly Subcutaneous Injections of the Fully Human Anti-TNF Antibody D2E7 in Patients with Rheumatoid Arthritis—Results of a Phase I Study," Arthritis Rheum., 41(9):S57, Sep. 1998.
Schein, "Solubility as a Function of Protein Structure and Solvent Components," BioTechnology 8:308-317, Apr. 1990.
Schwartz, "Diafiltration for Desalting or Buffer Exchange," BioPress, 6 pages, 2003.
Schwartzman et al., "Does route of administration affect the outcome of TNF antagonist therapy?," Arthritis Research and Therapy 6(Suppl. 2):S19-S23, 2004.
Scotchler et al., "Deamidation of Glutaminyl Residues: Dependence on pH, Temperature, and Ionic Strength," Analytical Biochemistry 59:319-322, 1974.
Seeking Alpha, "Coherus Biosciences: The Biosimilar Market is Enormous and This Company is Well Positioned," Dec. 29, 2014, 7 pages.
Serebrov M., "Wait Continues as New Market Teeters on Bring of Explosion," BioWorld: Thomson Reuters, dated May 3, 2016, 21 pages.
Shire, S. J., "Monoclonal Antibodies," Woodhead Publishing Series in Biomedicine: No. 77, year 2015, 219 pages.
Singh and Singh, "Effect of Polyols on the Conformational Stability and Biological Activity of a Model Protein Lysozyme," AAPS PharmSciTech, Article 42, Jul. 2003, 4(3): 9 pages.
Sorbera et al., "Adalimumab," Drugs Fut. 26(7):639-646, 2001.
Stefan Ewert, et al., "Biophysical Properties of Human Antibody Variable Domains," 325 J. Mol. Biol. 531 (2003).
Stites et al., "Immunoglobulins & Immunoglobulin Genes," Medical Immunology: 9th Edition, year 1997, 22 pages.
Stoner et al., "Protein-Solute Interactions Affect the Outcome of Ultrafiltration/Diafiltration Operations," J. Phann. Sci. 93:2332-2342 (2004).
Supplemental Amendment and Response, filed Feb. 13, 2012 in U.S. Prosecution History of U.S. Appl. No. 10/525,292 (U.S. Pat. No. 8,216,583), 13 pages.
Synagis® Label (Jul. 2004).
Taiwanese Office Action in Taiwanese Appln. No. 102132360, dated Oct. 25, 2017, 8 pages (with English translation).
Theodore W. Randolph & John F. Carpenter, Engineering Challenges of Protein Formulations, 53 Am. Inst. Chem. Eng. J. 1902 (2007).
Tim J. Kamerzell et al., "Increasing IgG Concentration Modulates the Conformational Heterogeneity and Bonding Network that Influence Solution Properties," 113 J. Phys. Chem. B 6109 (2009).
Timmerman, "Abbot's Humira the 3rd-in-Class Drug that toppled Lipitor as No. 1," Xconomy, Apr. 16, 2012, 6 pages.
Tindall et al., "Mobile Phase Buffers, Part II," LC, GC Europe, 2-4, 2003.
Treuheit et al., "Inverse Relationship of Protein Concentration and Aggregation," Pharm. Res. 19(4):511-516, 2002.

(56) References Cited

OTHER PUBLICATIONS

Tsourounis, "Biologic therapies for the treatment of chronic plaque psoriasis," Formulary 40:184-199, 2005.
Tysabri® Label (Nov. 2004).
U.S. Prosecution History of U.S. Appl. No. 12/325,049, (U.S. Pat. No. 8,420,081), 2482 pages, filed Nov. 28, 2008.
U.S. Prosecution History of U.S. Appl. No. 13/774,735 (U.S. Pat. No. 8,883,146), 1215 pages, filed Feb. 22, 2013.
U.S. Prosecution History of U.S. Appl. No. 14/506,576 (U.S. Pat. No. 9,085,619), 489 pages, filed Oct. 3, 2014.
U.S. Prosecution History of U.S. Appl. No. 14/558,182 (U.S. Pat. No. 9,114,166), filed Dec. 2, 2014, 721 pages.
U.S. Prosecution History of U.S. Appl. No. 61/004,992, 237 pages, filed Nov. 30, 2007.
U.S. Prosecution History of U.S. Appl. No. 10/222,140, 109 pages, filed Aug. 19, 2002.
U.S. Prosecution History of U.S. Appl. No. 13/654,795, 6 pages, filed 2015.
U.S. Prosecution History of U.S. Appl. No. 13/654,950 (U.S. Pat. No. 9,302,002), 7 pages, filed 2014.
U.S. Prosecution History of U.S. Appl. No. 14/020,733, 10 pages, filed 2015.
U.S. Prosecution History of U.S. Appl. No. 14/643,844 (U.S. Pat. No. 9,340,611), 7 pages, filed 2015.
United Healthcare 2015 Four-Tier Prescription Drug List, Jul. 2015, 35 pages.
United States Pharmacopeia and National Formulary (USP 24-NF 19). vol. 2. Rockville, MD: United States Pharmacopeia Convention; 1999: 1971-1977, 2011-2021, 2404-2406.
USPTO Certified Copy of Priority Document PCT/US2006/022599 for U.S. Appl. No. 60/690,582, filed Jun. 14, 2005, 18 pages.
Van de Putte et al., "A Single Dose Placebo Controlled Phase I Study of the Fully Human Anti-TNF Antibody D2E7 in Patients with Rheumatoid Arthritis," Arthritis Rheum. 41(9):S57, Sep. 1998.
Van de Putte et al., "Efficacy of the Fully Human Anti-TNF Antibody D2E7 in Rheumatoid Arthritis," Arthritis Rheum. 42(9):S400, Sep. 1999.
Van de Putte et al., "Six Month Efficacy of the Fully Human Anti-TNF Antibody D2E7 in Rheumatoid Arthritis," Annals of the Rheumatic Diseases 59:(Suppl I), Op.056, 2000.
Van Gestel et al., "Development and Validation of the European League Against Rheumatism Response Criteria for Rheumatoid Arthritis," Arthritis & Rheumatism, vol. 39, No. 1, Jan. 1996, pp. 34-40.
Van Slyke, "On the Measurement of Buffer Values and on the Relationship of Buffer Value to the Dissociation Constant of the Buffer and the Concentration and Reaction of the Buffer Solution," J. Biol. Chem. 52:525-570 (1922).
Vectibix® Label (Sep. 2006).
Veys et al., "Pain at the injection site of subcutaneously administered erythropoietin: phosphate-buffered epoetin alpha compared to cirate-buffered epoetin alpha and epoetin beta," Clin. Nep. vol. 49, No. 1, pp. 41-44, 1998.
Vincent Lee, "Peptide and Protein Drug Delivery," pp. 247-301, Marcel Dekker, New York, N.Y., 1991.
Vivaglobin® Label (Jan. 2006).
Wang et al. "Antibody structure, instability, and formulation," Minirevew, accepted Jun. 4, 2006.
Wang, "Instability, stabilization, and formulation of liquid protein pharmaceuticals," Int. J. Pharm. 185:129-188, 1999.
Warne, "Development of high concentration protein biopharmaceuticals: The use of platform approaches in formulation development," European J. Pharmaceutics and Biopharmaceutics 78(2):208-212, Mar. 2011.
Weaver, "Abbott Drug Unit Embarks on New Life Without Parent," The Wall Street Journal, Jan. 2, 2013.
Wright et al., "Nonenzymatic Deamidation of Asparaginyl and Glutaminyl Residues in Protein," Critical Reviews in Biochemistry and Molecular Biology, 26:1, pp. 1-52, 1991.
Yim, "Summary Review for Regulatory Action," Division of Pulmonaiy, Allergy, and Rheumatology Products (DPARP), of Humira, 2015, 13 pages.
Zhang et al., "Comparative Study on Kinetics of Nonenzymatic Deamidation of Soy Protein and Egg White Lysozyme," J. Agric. Food Chem. 41:2286-2290, 1993.
Zymewire Blog, Coherus Biosciences' Outsourcing Strategy, Sep. 28, 2014, 3 pages.
International Search Report and Written Opinion for corresponding PCT Application No. PCT/US2017/028663 dated Sep. 5, 2017.
Bender et al., Alternative buffers for pharmaceutical anti-TNF alpha monoclonal antibody formulations [Elektronische Ressource], PAPDEOTTOO, Feb. 6, 2013 (Feb. 6, 2013), Opp, XP009188701, 10 Pages.

* cited by examiner

METHOD OF FILLING A CONTAINER WITH NO HEADSPACE

CROSS REFERENCE TO RELATED APPLICATIONS

This application claims priority to U.S. Provisional Application No. 62/453,370, filed on Feb. 1, 2017, U.S. Provisional Application No. 62/440,955, filed on Dec. 30, 2016, U.S. Provisional Application No. 62/438,216, filed on Dec. 22, 2016, and U.S. Provisional Application No. 62/325,387, filed on Apr. 20, 2016. The entire contents of the foregoing are incorporated herein by reference.

TECHNICAL FIELD

The present invention relates to aqueous pharmaceutical compositions in containers with zero headspace suitable for long-term storage, methods of manufacturing the compositions in a container with zero headspace, and machines for manufacturing compositions in a container with zero headspace.

BACKGROUND OF THE INVENTION

Aqueous drug products, including the therapeutic drug substance in the drug product, are subjected to mechanical and chemical stresses when they are manufactured, packaged, transported, stored, and handled prior to administration to a patient. These stresses are detrimental to all drug substances including biologic drug substances (e.g. protein drugs) and non-biologic drug substances (e.g. small molecule drugs). Drug substance are known to degrade or fragment when subjected to mechanical stresses such as physical impact and shear stress. Drug substance, and inactive components of drug products, can also be degraded by unwanted chemical modification such as oxidation. Additionally, proteins are known to aggregate when subject to such stresses. This is a problem because aggregated and degraded drugs have a reduced therapeutic benefit to patients and in some cases may be immunogenic.

The presence of headspace in a container holding a drug product exacerbates the mechanical stress placed upon the drug product. Specifically, the presence of headspace leads to greater shearing stress of the drug product as the liquid is allowed to flow and impact the walls of the container. This greater shearing stress leads to greater aggregation and degradation.

Further, the presence of a headspace in containers creates a gas-solution interface. This headspace is commonly filled with atmospheric air, which contains reactive gases, including molecular oxygen. The interaction that takes place at the gas-solution interface between a drug substance and reactive gases, such as molecular oxygen and other constituents of atmospheric air, can also lead to degradation of the drug substance such as oxidation.

To overcome the problems caused by mechanical stress and the gas-solution interface drug manufacturers include stabilizers and non-ionic surfactants in their drug products. These surfactants create a barrier at the gas-solution interface that prevents the drug substance from adsorbing to the gas-solution interface and interacting with the headspace thus reducing degradation. Further, surfactants are also used to prevent aggregation of drug product under shear stress. However, drug product manufacturers commonly aim to reduce the levels of surfactants included in their drug products due to both monetary and regulatory considerations. First, surfactants are relatively expensive excipients and extensive formulation development activities are required to optimize type and level of surfactant for any particular drug product. Second, surfactants are highly regulated by the U.S. Food and Drug Administration and other world health authorities because of their possible and known negative effects on humans when internalized. Third, many commonly used surfactants contain process related impurities. They are susceptible to oxidation and hydrolytic reaction, and the impurities and degradation of surfactant can impact on product quality.

Hoffman-La Roche Inc. was issued U.S. Pat. No. 7,879,976 ("the '976 patent") directed to reducing the amount of headspace in a container when filling the container with an aqueous protein solution. However, the '976 patent fails to disclose a method by which the headspace in the container is 0% of the container volume and the aqueous protein formulation is less than 100% of the container volume. Instead, the methods of the '976 patent were only able to reduce headspace to about 3% of the total volume of the container when the aqueous protein solution was less than 100% of the total volume. There remains the need to fill a container (e.g. a syringe) to less than 100% of the total volume of the container and eliminate the headspace. The inability to eliminate the headspace in the container without filling the container to 100% with aqueous protein solution is problematic when filling syringes. Syringes must contain space for a stopper to be inserted into the syringe so that stopper seals the syringe for long term storage and a can serve as plunger during administration of the drug product. Due to the need for this additional space, syringes cannot be filled to 100% capacity with the drug product.

Further, there are two syringe stoppering processes, namely mechanical and vacuum stoppering. Reducing the headspace by the mechanical stoppering process is limited by the drug product rising along the stopper wall once the stopper is in contact with the solution. This capillary effect leads to inaccurate drug product volume in the syringe and the liquid between stopper ribs leads to further defects. For the vacuum stoppering process, reducing the headspace is impacted by the limit of vacuum level that can be achieved by current commercial filling systems and also the loss of solution under deep vacuum conditions.

Thus, there is a need in the art for methods of reducing or eliminating the headspace in containers for pharmaceutical use such as pre-filled syringes and cartridges. These methods enable the manufacture of drug products in containers without a headspace. The result is a stable drug product wherein the use of surfactants and other stabilizing excipients is reduced or eliminated.

SUMMARY OF THE INVENTION

In one embodiment, the invention provides a method for preparing a container with zero headspace comprising an aqueous drug substance solution, the method comprising:
a) providing a container with an open end;
b) providing an aqueous drug substance solution;
c) filling the container via the open end with the aqueous drug substance solution;
d) purging the container with at least one soluble gas;
e) inserting a stopper into the open end of the container creating a headspace of soluble gas; and
f) storing the container,
wherein the stopper can move within the container while maintaining an airtight seal; and the storage step results in the container having no visibly detectable headspace.

In one embodiment, prior to the purging step, the container with the aqueous drug substance solution is subjected to a pressure vacuum.

In one embodiment, the vacuum results in a pressure from about 22 mbar to about 100 mbar.

The soluble gas may be, or may include, carbon dioxide.

In one embodiment, prior to stoppering, the container with the aqueous drug substance solution is subjected to a pressure vacuum.

The stopper may optionally be inserted by vacuum stoppering.

In one embodiment, the soluble gas headspace has a pressure lower than atmospheric pressure.

In one embodiment, the container is stored for at least 4 hours.

In one embodiment, the storing step is conducted at a temperature below the temperature at which the stoppering step occurred.

In one embodiment, the storage step results in the container having zero headspace.

In one embodiment, the method for preparing a container with zero headspace comprising an aqueous drug substance solution comprises the following steps:
a) providing a container with an open end;
b) providing an aqueous drug substance solution;
c) filling the container via the open end with the aqueous drug substance solution;
d) degassing the container and aqueous drug substance solution via a pressure vacuum;
e) purging the container with at least one soluble gas;
f) optionally repeating the degassing and purging steps;
g) degassing via a pressure vacuum and while under vacuum, inserting a stopper into the open end of the container creating a headspace of soluble gas; and
h) storing the container.

In any of the embodiments of the invention, the container may be a syringe or a cartridge. The syringe may comprise a closed end closed with a needle.

In any of the embodiments of the invention, the aqueous drug substance solution may comprise a biologic or non-biologic drug substance. The non-biologic molecule solution may be a pharmaceutical composition comprising a small molecule. The biologic drug substance may be a protein. The biologic drug substance may also be an antibody. The antibody may be adalimumab.

In any of the embodiments of the invention, the pharmaceutical composition may be free or substantially free of surfactant, polyol, sugar, buffer, salt, stabilizer, or combinations thereof.

In any of the embodiments of the invention, the pharmaceutical composition may be free or substantially free of surfactant, polyol, sugar, and buffer.

In any of the embodiments of the invention, the pharmaceutical composition may be free or substantially free of surfactant, polyol, sugar, and salt.

In any of the embodiments of the invention, the aqueous drug substance solution may comprise an amino acid. The amino acid may be selected from alanine, lysine, threonine, valine, leucine, isoleucine, histidine, glycine, methionine, serine, proline, and arginine and combinations thereof. In particular, in some embodiment, the amino acid may comprise arginine. In other embodiments, the amino acid may comprise arginine and glycine. In other embodiment, the amino acid may comprise serine, lysine, and valine. In other embodiments, the amino acid may comprise threonine, valine, and leucine. In other embodiments, the amino acid may comprise lysine, methionine, and proline. In other embodiments, the amino acid may comprise serine, lysine, and leucine. In other embodiments, the amino acid may comprise threonine, leucine, and methionine.

In any of the embodiments of the invention, the aqueous drug substance solution may comprise a salt. The salt may comprise a sodium cation or calcium cation. The salt may comprise NaCl, $Na_2SO_4$ or $CaCl_2$.

In any of the embodiments of the invention, the aqueous drug substance solution comprises an amino acid and a salt. The invention is intended to cover all possible permutations of combinations of amino acids and salts. Some non-exclusive examples of possible combinations include: 1) arginine, glycine and a calcium cation, preferably $CaCl_2$; and 2) arginine, glycine, threonine, and a calcium cation, preferably $CaCl_2$.

In any of the embodiments of the invention, the aqueous drug substance solution may be stable for at least one week at 40° C. or two weeks at 25° C.

In any of the embodiments of the invention, the aqueous drug substance solution may be stable (i) for at least three months; (ii) for at least six months; or (iii) for at least one year.

In any of the embodiments of the invention, the aqueous drug substance solution may have stability comparable to, or better than, the same aqueous drug substance solution in a container with a headspace.

In one embodiment of the invention, the aqueous drug substance solution is free or substantially free of surfactant; and has stability comparable to, or better than, an aqueous solution of the same drug substance that contains surfactant in a container with a headspace.

In one embodiment of the invention, the aqueous drug substance solution is free or substantially free of polyol; and has stability comparable to, or better than, an aqueous solution of the same drug substance that contains polyol in a container with a headspace.

In one embodiment of the invention, the aqueous drug substance solution is free or substantially free of sugar; and has stability comparable to, or better than, an aqueous solution of the same drug substance that contains sugar in a container with a headspace.

In one embodiment of the invention, the aqueous drug substance solution is free or substantially free of buffer; and has stability comparable to, or better than, an aqueous solution of the same drug substance that contains buffer in a container with a headspace.

In one embodiment of the invention, the aqueous drug substance solution is free or substantially free of surfactant, polyol, sugar, buffer or combinations thereof; and has stability comparable to, or better than, an aqueous solution of the same drug substance that contains surfactant, polyol, sugar, buffer or combinations thereof in a container with a headspace.

In one embodiment, the invention provides a container closed with a stopper comprising a stable aqueous drug substance solution within the container and no visibly detectable headspace, wherein the volume of the aqueous drug substance solution is less than 100% of the container volume. The container may be prepared by any of the methods described above. The container may have zero headspace.

In one embodiment, the aqueous drug substance solution has fewer subvisible particles than the same aqueous drug substance solution in a container with a headspace.

In one embodiment, the aqueous drug substance solution is free or substantially free of surfactant; and has fewer subvisible particles than an aqueous solution of the same drug substance that contains surfactant in a container with a headspace.

In one embodiment, the aqueous drug substance solution is free or substantially free of polyol; and has fewer subvisible particles than an aqueous solution of the same drug substance that contains polyol in a container with a headspace.

In one embodiment, the aqueous drug substance solution is free or substantially free of sugar; and has fewer subvisible particles than an aqueous solution of the same drug substance that contains sugar in a container with a headspace.

In one embodiment, the aqueous drug substance solution is free or substantially free of buffer; and has fewer subvisible particles than an aqueous solution of the same drug substance that contains buffer in a container with a headspace.

In one embodiment, the aqueous drug substance solution is free or substantially free of surfactant, polyol, sugar, buffer or combinations thereof; and has fewer subvisible particles than an aqueous solution of the same drug substance that contains surfactant, polyol, sugar, buffer or combinations thereof in a container with a headspace.

In one embodiment, the aqueous drug substance solution is isotonic.

In another embodiment, the invention provides a machine for performing any of the provided methods of preparing a container with zero headspace, wherein the machine comprises
  a) means for filling a container with an aqueous drug substance solution;
  b) means for purging the container with a soluble gas; and
  c) means for inserting a stopper into the open end of the container.

In one embodiment, the purging, stoppering and, optionally, filling of the container occurs within a sealed chamber.

In one embodiment, the machine is programmed to perform at least one step of any of the provided methods of preparing a container with zero headspace.

In one embodiment, the invention provides a machine for performing any of the provided methods of preparing a container with zero headspace, wherein the machine comprises
  a) means for filling a container with an aqueous drug substance solution;
  b) means for applying a vacuum to the container and aqueous drug substance solution;
  c) means for purging the container with a soluble gas; and
  d) means for inserting a stopper into the open end of the container.

In one embodiment, the degassing, purging, stoppering and, optionally, filling of the container occurs within a sealed chamber.

In one embodiment, the machine is programmed to perform at least one step of any of the provided methods of preparing a container with zero headspace.

In one embodiment, the invention provides a stable pharmaceutical composition comprising:
  a) adalimumab,
  b) stabilizer comprising an amino acid, and
  c) salt;
wherein the composition is free of buffer, polyol, and surfactant; has a pH of about 5 to about 6; and has a conductivity of greater than 3.0 mS/cm.

In one embodiment, the stabilizer comprises two or more amino acids.

In one embodiment, the stabilizer comprises glycine and arginine.

In one embodiment, the stabilizer comprises glycine, arginine, and threonine.

In one embodiment, the salt comprises a divalent cation. The divalent cation may be selected from the group consisting of $Ca^{2+}$, and $Mg^{2+}$.

In one embodiment, the salt comprises $MgCl_2$ or $CaCl_2$.

In one embodiment, the salt is selected from NaCl, KCl, $Na_2SO_4$, $MgCl_2$, $CaCl_2$, and adipate.

In one embodiment, the stabilizer comprises glycine and arginine, and the salt comprises $CaCl_2$.

In one embodiment, the stabilizer comprises glycine, arginine, and threonine, and the salt comprises $CaCl_2$.

In one embodiment, the pH of any of the provided compositions is about 5.2.

In one embodiment, the invention provides a stable pharmaceutical composition comprising:
  a) adalimumab,
  b) stabilizer comprising an amino acid, and
  c) salt;
wherein the composition is free of buffer, polyol, and surfactant; has a pH of about 5 to about 6; and has a conductivity of greater than 3.0 mS/cm, wherein the composition has osmolality of about 180 to 420 mOsM; the composition is suitable for administration to a subject as a single dosage; the composition has a concentration of adalimumab in the range of 30 to about 50 mg/ml; and the dosage contains about 10 to 80 mg of adalimumab.

In one embodiment, the concentration of adalimumab is about 50 mg/ml and the dosage is about 40 mg.

In one embodiment, the dosage is about 40 mg and results in less pain upon administration to a subject in comparison to an adalimumab composition having a buffer comprising citrate.

In one embodiment, the composition is stable for one or more of:
  a) 7 days at −40° C.,
  b) 14 days at −40° C.,
  c) 30 days at −40° C.,
  d) 7 days at 5° C.,
  e) 14 days at 5° C.,
  f) 30 days at 5° C.,
  g) 7 days at 25° C.,
  h) 14 days at 25° C.,
  i) 30 days at 25° C.,
  j) 7 days at 40° C.,
  k) 14 days at 40° C., or
  l) 30 days at 40° C.

In one embodiment, the composition is contained in a container comprising no headspace.

In one embodiment, the composition has stability comparable to, or greater than, a Humira® formulation.

In one embodiment, the composition has fewer subvisible particles than a Humira® formulation.

In one embodiment, the invention provides a stable pharmaceutical composition in a container with zero headspace, the composition comprising:
  a) adalimumab,
  b) stabilizer comprising an amino acid, and
  c) salt;
wherein the composition is free of buffer, polyol, and surfactant; has a pH of about 5 to about 6;
and has a conductivity of greater than 3.0 mS/cm.

In one embodiment, the stabilizer comprises two or more amino acids.

In one embodiment, the stabilizer comprises glycine and arginine.

In one embodiment, the stabilizer comprises glycine, arginine, and threonine.

In one embodiment, the salt comprises a divalent cation. The divalent cation may be selected from the group consisting of $Ca^{2+}$, and $Mg^{2+}$.

In one embodiment, the salt comprises $MgCl_2$ or $CaCl_2$.

In one embodiment, the salt is selected from NaCl, KCl, $Na_2SO_4$, $MgCl_2$, $CaCl_2$, and adipate.

In one embodiment, the stabilizer comprises glycine and arginine, and the salt comprises $CaCl_2$.

In one embodiment, the stabilizer comprises glycine, arginine, and threonine, and the salt comprises $CaCl_2$.

In one embodiment, the pH of any of the provided compositions is about 5.2.

In one embodiment, the invention provides a stable pharmaceutical composition in a container with zero headspace, the composition comprising:
 a) adalimumab,
 b) stabilizer comprising an amino acid, and
 c) salt;
wherein the composition is free of buffer, polyol, and surfactant; has a pH of about 5 to about 6; and has a conductivity of greater than 3.0 mS/cm, wherein the composition has osmolality of about 180 to 420 mOsM; the composition is suitable for administration to a subject as a single dosage; the composition has a concentration of adalimumab in the range of 30 to about 50 mg/ml; and the dosage contains about 10 to 80 mg of adalimumab.

In one embodiment, the concentration of adalimumab is about 50 mg/ml and the dosage is about 40 mg.

In one embodiment, the dosage is about 40 mg and results in less pain upon administration to a subject in comparison to an adalimumab composition having a buffer comprising citrate.

In one embodiment, the composition is stable for one or more of:
 a) 7 days at −40° C.,
 b) 14 days at −40° C.,
 c) 30 days at −40° C.,
 d) 7 days at 5° C.,
 e) 14 days at 5° C.,
 f) 30 days at 5° C.,
 g) 7 days at 25° C.,
 h) 14 days at 25° C.,
 i) 30 days at 25° C.,
 j) 7 days at 40° C.,
 k) 14 days at 40° C., or
 l) 30 days at 40° C.

In one embodiment, the composition is contained in a container comprising no headspace.

In one embodiment, the composition has stability comparable to, or greater than, a Humira® formulation.

In one embodiment, the composition has fewer subvisible particles than a Humira® formulation.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 10. Sub-visible particles 10 μm in solutions in containers with zero headspace stored at 40° C. for 30 days.

DETAILED DESCRIPTION OF THE INVENTION

Figure 1:
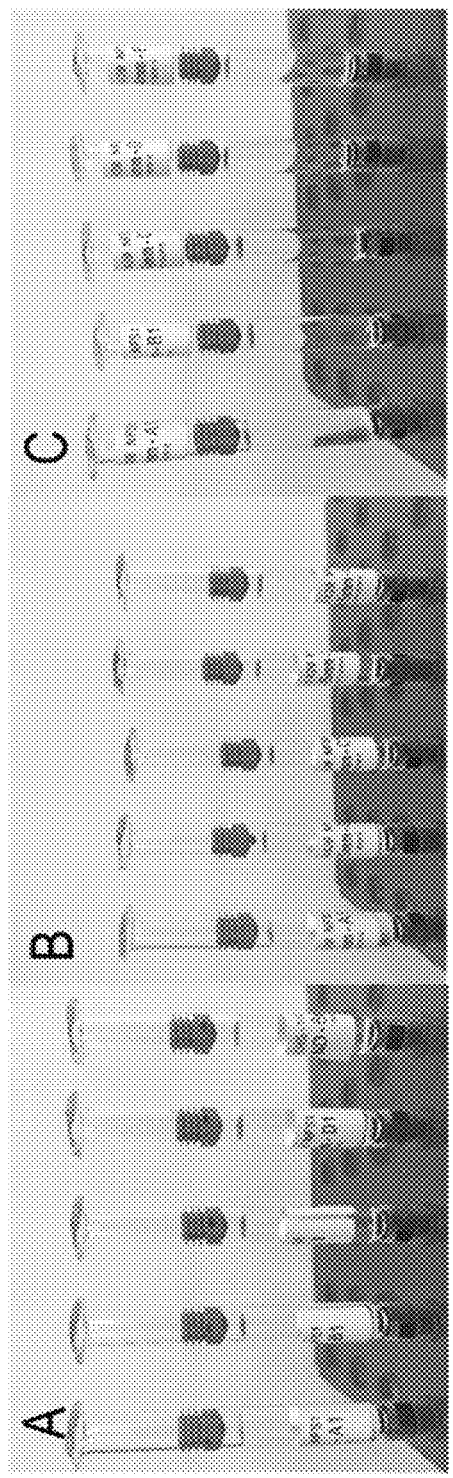
FIG. 1. Reduced headspace in syringes filled with non-degassed bulk aqueous protein solution following the process in Example 1. Resulting headspaces are shown in panels A, B, and C for syringes that had initial headspaces of 6 millimeters 5 millimeters, and 4 millimeters, respectively.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. In the case of conflict, the present document, including definitions will control.

Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

Definitions

Unless otherwise defined, all technical and scientific terms used herein have the same meaning as commonly understood by one of ordinary skill in the art to which this invention pertains. In the case of conflict, the present document, including definitions will control.

As used herein the term "optionally" refers to distinct methods or compositions one of which contains the subsequent step(s) or composition(s) and one of which does not.

As used herein the term "allowing" refers to any method of causing a result to occur including but not limited to taking no action.

As used herein, the term "container" refers to a pharmaceutically acceptable container comprising a chamber suitable to house a liquid or semi-solid drug product. As used herein the "closed end" of the container refers to the end of the chamber having either no opening or an attached delivery device or means for attaching a delivery device. As used herein the term "open end" of the container refers to the end of the chamber opposite the closed end. The "open end" of the container is configured as to receive a liquid or semi-solid drug product. The "proximal end" of the open end of the container refers to the end closest to the closed end of the container. The "distal end" of the open end of the container refers to the end farthest from the closed end of the container. Containers include, for example, vials, syringes, cartridges, capsules, and ampoules.

As used herein, the term "pliable container" refers to a non-rigid pharmaceutically acceptable container comprising a chamber suitable to house a liquid or semi-solid drug product. A pliable container is capable of flexing, deforming, collapsing, or bending to conform to the shape or volume of the contents within. Pliable containers include, for example, polypropylene and polyurethane bags.

As used herein, the term "delivery device" refers to a device suitable for delivering a liquid or semi-solid drug product to a patient. The delivery device may be suitable for delivery of drug product directly to a patient or via an intermediary step (e.g. intravenous bag or line). Delivery devices include, for example, screw-on ports, hollow needles, microneedles, cannulas, and jet injectors.

As used herein the term "syringe" refers to a chamber attached to a hollow needle or means for attaching a hollow needle wherein the chamber is of sufficient size to house a liquid or semi-solid drug product. As used herein the "closed end" of the syringe refers to the end of the chamber having the attached hollow needle or means for attaching the hollow needle. As used herein the term "open end" of the syringe refers to the end of the chamber opposite the closed end. The "open end" of the syringe is configured as to receive a liquid or semi-solid drug product. The "proximal end" of the open end of the syringe refers to the end closest to the closed end of the syringe. The "distal end" of the open end of the syringe refers to the end farthest from the closed end of the syringe.

As used herein the term "aqueous drug substance solution" refers to a liquid or semi-solid that contains water and a drug product and optionally one or more pharmaceutically acceptable excipients.

The term "drug product" refers to the active pharmaceutical ingredient in a pharmaceutical product (e.g. an aqueous drug substance solution). In one embodiment, the drug product is a biologic drug substance. In another embodiment, the drug product is a non-biologic drug substance.

The term "pharmaceutically acceptable" describes a material that is not biologically or otherwise undesirable (i.e. without causing an unacceptable level of undesirable biological effects or interacting in a deleterious manner.)

As used herein the term "biologic drug substance" includes, but is not limited to, vaccines, blood and blood components, allergenics, somatic cells, gene therapy, tissues, isolated natural proteins, recombinant proteins, biogenerics and biosimilars.

The term "biosimilar" or "biosimilars," as used herein, refers to a biological product designed to have active properties similar to an FDA-licensed biological product.

As used herein the term "protein" refers to a chain of amino acids bound by peptide bonds. Both naturally-occurring proteins, non-naturally-occurring proteins and other polypeptides are included in the present invention. In one embodiment, a protein for use in the present invention is an immunoglobulin. Non-limiting examples of proteins are described herein and additional examples of proteins are known in the art.

In one embodiment, a protein utilized in the methods and compositions of the present invention includes, but is not limited to, etanercept, filgrastim, pegfilgrastim, an interferon, a human growth hormone (e.g somatropin), and a hyaluronidase.

In one embodiment, the interferon includes, but is not limited to, Interferon alpha 2a (Roferon A), Interferon alpha 2b (Intron A/Reliferon/Uniferon), Human leukocyte Interferon-alpha (HuIFN-alpha-Le) (Multiferon), Interferon beta 1a, liquid (Rebif), Interferon beta 1a, lyophilized (Avonex), Interferon beta 1a, (Cinnovex), Interferon beta 1b (Betaseron/Betaferon), Interferon gamma 1b (Actimmune), PEGylated interferon alpha 2a (Pegasys), PEGylated interferon alpha 2a (Reiferon Retard), PEGylated interferon alpha 2b (PegIntron), and PEGylated interferon alpha 2b (Pegetron).

In one embodiment, the hyaluronidase includes, but is not limited to, the hyaluronidase active ingredient in the product sold under the tradename Hydase™ (developed and manufactured by PrimaPharm Inc., distributed by Akorn Inc.), Vitrase (Bausch+Lomb/Valeant Pharmaceuticals), Amphadase (Amphastar Pharmaceuticals), Wydase, and Hylenex (Halozyme Therapeutics).

As used herein, the term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')$_2$ fragment, or a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

As used herein, the term "antibody" or "antibodies" is intended to refer to immunoglobulin molecules comprised of four polypeptide chains, two heavy (H) chains and two light (L) chains connected by disulfide bonds. Antibodies capable of being utilized in the present invention include but are not limited to recombinant human antibodies including human monoclonal antibodies and 'fully' human monoclonal antibodies. Non-limiting examples of antibodies are described herein and additional examples of antibodies are known in the art.

In one embodiment, an antibody utilized in the methods and compositions of the present invention includes tumor necrosis factor (TNF)-α antibodies (also referred to as anti-TNFα antibodies). TNFα antibodies include, but are not limited to, adalimumab (adalimumab is sold under the trademark Humira® and is described in further detail in U.S. Pat. Nos. 6,090,382; 6,258,562; 6,509,015; and 8,664,945, each of which is incorporated herein by reference in its entirety), infliximab (infliximab is sold under the trademark REMICADE®; Remicade is a registered trademark of Janssen Biotech, Inc.), certolizumab pegol (pegol is sold under the trademark CIMZIA®; Cimzia is a registered trademark of UCB Pharma, SA) and golimumab (golimumab is sold under the trademark SIMPONI®; Simponi is a registered trademark of Johnson & Johnson).

In another embodiment, an antibody utilized in the methods and compositions of the present invention includes, but is not limited to, natalizumab (natalizumab is sold under the trademark TYSABRI®; Tysabri is a registered trademark of Biogen Idec MA, Inc.), ranibizumab (ranibizumab is sold under the trademark LUCENTIS®; Lucentis is a registered trademark of Genentech, Inc.), bevicizumab (bevicizumab is sold under the trademark AVASTIN®; Avastin is a registered trademark of Genentech, Inc.), rituximab (rituximab is sold under the trademark RITUXAN®; Rituxan is a registered trademark of Biogen Idec, Inc.), eculizumab (eculizumab is sold under the trademark SOLIRIS®; Soliris is a registered trademark of Alexion Pharmaceuticals, Inc.), ustekinumab (ustekinumab is sold under the trademark STELARA®; Stelara is a registered trademark of Johnson & Johnson, Inc.), denosumab (denosumab is sold under the trademarks PROLIA®; Prolia is a registered trademark of Amgen, Inc. and XGEVA®; Xgeva is a registered trademark of Amgen, Inc.), tocilizumab (tocilizumab is sold under the trademark ACTEMRA®; Actemra is a registered trademark of Chugai Seiyaku Kabushiki Kaisha Corp.), ipilimumab (ipilimumab is sold under the trademark YERVOY®; Yervoy is a registered trademark of Bristol-Myers Squibb Comp.), omalizumab (omalizumab is sold under the trademark XOLAIR®; Xolair is a registered trademark of Novartis AG), ramucirumab (ramucirumab is sold under the trademark CYRAMZA®; Cyramza is a registered trademark of ImClone LLC), vedolizumab (vedolizumab is sold under the trademark ENTYVIO®; Entyvio is a registered trademark of Millennium Pharmaceuticals, Inc.), belimumab (belimumab is sold under the trademark BENLYSTA®; Benlysta is a registered trademark of GlaxoSmithKline Intellectual Property Limited), epratuzumab, nivolumab, secukinumab, gevokizumab.

As used herein, the term "non-biologic drug substance" refers to a pharmaceutical agent that is not classified as biologic drug, including but not limited to, small molecule drugs and Non Biological Complex Drugs (NBCD). Small molecules are organic compounds characterized by low molecular weight (typically <900 daltons). NBCD are synthetic complex compounds and they contain non-homomolecular, closely related molecular structures with often nanoparticular properties. Non-limiting examples of non-biologic drug substances are described herein and additional examples of non-biologic drug substances are known in the art.

In another embodiment, a non-biologic drug substance utilized in the methods and compositions of the present invention includes, but is not limited to, an opioid and an antihistamine.

In another embodiment, an opioid includes, but is not limited to, morphine, hydromorphone, and oxycodone.

In another embodiment, the antihistamine includes, but is not limited to, an $H_1$ antagonist, $H_1$ inverse agonist, $H_2$-antihistamine, $H_3$-antihistamine, and $H_4$-antihistamine.

In one embodiment, the $H_1$ antagonist includes, but is not limited to, Acrivastine, Azelastine, Bilastine, Bromodiphenhydramine, Brompheniramine, Buclizine, Carbinoxamine, Cetirizine, Chlorodiphenhydramine, Chlorphenamine, Chlorpromazine, Clemastine, Cyclizine, Cyproheptadine, Dexbrompheniramine, Dexchlorpheniramine, Dimenhydrinate, Dimetindene, Diphenhydramine, Doxylamine, Ebastine, Embramine, Fexofenadine (Allegra), Hydroxyzine (Vistaril), Loratadine (Claritin), Meclizine, Mirtazapine, Olopatadine, Orphenadrine, Phenindamine, Pheniramine, Phenyltoloxamine, Promethazine, Quetiapine (Seroquel), Rupatadine, Tripelennamine, and Triprolidine.

In one embodiment, the $H_1$ inverse agonist includes, but is not limited to, Cetirizine, Levocetirizine, Desloratadine, and Pyrilamine.

In one embodiment, the $H_2$-antihistamine includes, but is not limited to, Cimetidine, Famotidine, Lafutidine, Nizatidine, Ranitidine, Roxatidine, and Tiotidine.

In one embodiment, the $H_3$-antihistamine includes, but is not limited to, Clobenpropit, ABT-239, Ciproxifan, Conessine, A-349821 (see, Esbenshade T A et al. (2004) "Pharmacological and behavioral properties of A-349821, a selective and potent human histamine H3 receptor antagonist". Biochemical Pharmacology. 68 (5): 933-45), and Thioperamide.

In one embodiment, the $H_4$-antihistamine includes, but is not limited to, Thioperamide, JNJ 7777120, and VUF-6002.

As used herein, the term "filling" refers to transferring the aqueous drug substance solution from a bulk container to a container. Containers can be filled individually or a plurality of containers can be filled simultaneously and/or sequentially. Preferably filling occurs in a gaseous environment consisting essentially of ambient atmosphere or at least on soluble gas, more preferably the gaseous environment is at an ambient pressure of about 1 atmosphere.

In one embodiment, filling occurs at a temperature at about room temperature. In another embodiment, filling occurs at a temperature from about 20° C. to about 90° C. In another embodiment, filling occurs at a temperature that does not exceed about 90° C., about 85° C., about 80° C., about 75° C., about 70° C., about 65° C., about 60° C., about 55° C., about 50° C., about 45° C., about 40° C., about 35° C., about 30° C., about 25° C., or about 20° C.

As used herein, the term "degassing" refers to removing molecules in a gaseous state from a container, from an aqueous solution (e.g. the aqueous drug substance solution), or from both the container and an aqueous solution. Preferably degassing occurs via a pressure vacuum. Degassing may occur for a length of time sufficient to achieve the desired degree of degassing. In one embodiment, degassing of the bulk aqueous drug substance solution occurs for 2 minutes or more. In another embodiment, degassing of the bulk aqueous drug substance solution occurs for 30 minutes or less and more preferably 60 minutes or less. In yet another embodiment, degassing of the bulk aqueous drug substance solution occurs for about 60 minutes, about 45 minutes, about 30 minutes, or about 15 minutes. In one embodiment, degassing of the container solution occurs for about 60 minutes, about 45 minutes, about 30 minutes, about 15 minutes, about 10 minutes, about 5 minutes, about 3 minutes, about 2 minutes, about 1 minute, or about 0.5 minutes, for at least 0.5 minutes. In certain embodiments, the bulk aqueous drug substance solution or the container solution is degassed by at least 10%.

As used herein, the term "pressure vacuum" or "vacuum" refers to creating a gaseous pressure lower than the ambient air pressure. A pressure vacuum is useful for various aspects of the present invention, including, but not limited to, degassing a solution, reducing or removing gas from within a container (e.g. the headspace), and closing a container (e.g. vacuum stoppering). In one embodiment, the pressure is 700 Torr or less, 500 Torr or less, 400 Torr or less, 300 Torr or less, 200 Torr or less, 100 Torr or less or 75 Torr or less. In another embodiment, degassing occurs via a pressure vacuum wherein the vacuum pressure is about 29.9 inHg, about 29.8 inHg, about 29.7 inHg, about 29.6 inHg, about 29.5 inHg, about 29.4 inHg, about 29.3 inHg, about 29.2 inHg, about 29.1 inHg, about 29 inHg, about 28.9 inHg, about 28.8 inHg, about 28.7 inHg, about 28.6 inHg, about 28.5 inHg, about 28.4 inHg, about 28.3 inHg, about 28.2 inHg, about 28.1 inHg, about 28 inHg, about 27.9 inHg, about 27.8 inHg, about 27.7 inHg, about 27.6 inHg, about 27.5 inHg, about 27.4 inHg, about 27.3 inHg, about 27.2 inHg, about 27.1 inHg, about 27 inHg, about 26.9 inHg, about 26.8 inHg, about 26.7 inHg, about 26.6 inHg, about 26.5 inHg, about 26.4 inHg, about 26.3 inHg, about 26.2 inHg, about 26.1 inHg, about 26 inHg, about 25.9 inHg, about 25.8 inHg, about 25.7 inHg, about 25.6 inHg, about 25.5 inHg, about 25.4 inHg, about 25.3 inHg, about 25.2 inHg, about 25.1 inHg, about 25 inHg, about 24.9 inHg, about 24.8 inHg, about 24.7 inHg, about 24.6 inHg, about 24.5 inHg, about 24.4 inHg, about 24.3 inHg, about 24.2 inHg, about 24.1 inHg, about 24 inHg, about 23.9 inHg, about 23.8 inHg, about 23.7 inHg, about 23.6 inHg, about 23.5 inHg, about 23.4 inHg, about 23.3 inHg, about 23.2 inHg, about 23.1 inHg, about 23 inHg, about 22.9 inHg, about 22.8 inHg, about 22.7 inHg, about 22.6 inHg, about 22.5 inHg, about 22.4 inHg, about 22.3 inHg, about 22.2 inHg, about 22.1 inHg, about 22 inHg, about 21.9 inHg, about 21.8 inHg, about 21.7 inHg, about 21.6 inHg, about 21.5 inHg, about 21.4 inHg, about 21.3 inHg, about 21.2 inHg, about 21.1 inHg, about 21 inHg, about 20.9 inHg, about 20.8 inHg, about 20.7 inHg, about 20.6 inHg, about 20.5 inHg, about 20.4 inHg, about 20.3 inHg, about 20.2 inHg, about 20.1 inHg, or about 20 inHg. In another embodiment, the pressure is about 300 mbar, about 299 mbar, about 298 mbar, about 297 mbar, about 296 mbar, about 295 mbar, about 294 mbar, about 293 mbar, about 292 mbar, about 291 mbar, about 290 mbar, about 289 mbar, about 288 mbar, about 287 mbar, about 286 mbar, about 285 mbar, about 284 mbar, about 283 mbar, about 282 mbar, about 281 mbar, about 280 mbar, about 279 mbar, about 278 mbar, about 277 mbar, about 276 mbar, about 275 mbar, about 274 mbar, about 273 mbar, about 272 mbar, about 271 mbar, about 270 mbar, about 269 mbar, about 268 mbar, about 267 mbar, about 266 mbar, about 265 mbar, about 264 mbar, about 263 mbar, about 262 mbar, about 261 mbar, about 260 mbar, about 259 mbar, about 258 mbar, about 257 mbar, about 256 mbar, about 255 mbar, about 254 mbar, about 253 mbar, about 252 mbar, about 251 mbar, about 250 mbar, about 249 mbar, about 248 mbar, about 247 mbar, about 246 mbar, about 245 mbar, about 244 mbar, about 243 mbar, about 242 mbar, about 241 mbar, about 240 mbar, about 239 mbar, about 238 mbar, about 237 mbar, about 236 mbar, about 235 mbar, about 234 mbar, about 233 mbar, about 232 mbar, about 231 mbar, about 230 mbar, about 229 mbar, about 228 mbar, about 227 mbar, about 226 mbar, about 225 mbar, about 224 mbar, about 223 mbar, about 222 mbar, about 221 mbar, about 220 mbar, about 219 mbar, about 218 mbar, about 217 mbar, about 216 mbar, about 215 mbar, about 214 mbar, about 213 mbar, about 212 mbar, about 211 mbar, about 210 mbar, about 209 mbar, about 208 mbar, about 207 mbar, about 206 mbar, about 205 mbar, about 204 mbar, about 203 mbar, about 202 mbar, about 201 mbar, about 200 mbar, about 199 mbar, about 198 mbar, about 197 mbar, about 196 mbar, about 195 mbar, about 194 mbar, about 193 mbar, about 192 mbar, about 191 mbar, about 190 mbar, about 189 mbar, about 188 mbar, about 187 mbar, about 186 mbar, about 185 mbar, about 184 mbar, about 183 mbar, about 182 mbar, about 181 mbar, about 180 mbar, about 179 mbar, about 178 mbar, about 177 mbar, about 176 mbar, about 175 mbar, about 174 mbar, about 173 mbar, about 172 mbar, about 171 mbar, about 170 mbar, about 169 mbar, about 168 mbar, about 167 mbar, about 166 mbar, about 165 mbar, about 164 mbar, about 163 mbar, about 162 mbar, about 161 mbar, about 160 mbar, about 159 mbar, about 158 mbar, about 157 mbar, about 156 mbar, about 155 mbar, about 154 mbar, about 153 mbar, about 152 mbar, about 151 mbar, about 150 mbar, about 149 mbar, about 148 mbar, about 147 mbar, about 146 mbar, about 145 mbar, about 144 mbar, about 143 mbar, about 142 mbar, about 141 mbar, about 140 mbar, about 139 mbar, about 138 mbar, about 137 mbar, about 136 mbar, about 135 mbar, about 134 mbar, about 133 mbar, about 132 mbar, about 131 mbar, about 130 mbar, about 129 mbar, about 128 mbar, about 127 mbar, about 126 mbar, about 125 mbar, about 124 mbar, about 123 mbar, about 122 mbar, about 121 mbar, about 120 mbar, about 119 mbar, about 118 mbar, about 117 mbar, about 116 mbar, about 115 mbar, about 114 mbar, about 113 mbar, about 112 mbar, about 111 mbar, about 110 mbar, about 109 mbar, about 108 mbar, about 107 mbar, about 106 mbar, about 105 mbar, about 104 mbar, about 103 mbar, about 102 mbar, about 101 mbar, about 100 mbar, about 99 mbar, about 98 mbar, about 97 mbar, about 96 mbar, about 95 mbar, about 94 mbar, about 93 mbar, about 92 mbar, about 91 mbar, about 90 mbar, about 89 mbar, about 88 mbar, about 87 mbar, about 86 mbar, about 85 mbar, about 84 mbar, about 83 mbar, about 82 mbar, about 81 mbar, about 80 mbar, about 79 mbar, about 78 mbar, about 77 mbar, about 76 mbar, about 75 mbar, about 74 mbar, about 73 mbar, about 72 mbar, about 71 mbar, about 70 mbar, about 69 mbar, about 68 mbar, about 67 mbar, about 66 mbar, about 65 mbar, about 64 mbar, about 63 mbar, about 62 mbar, about 61 mbar, about 60 mbar, about 59 mbar, about 58 mbar, about 57 mbar, about 56 mbar, about 55 mbar, about 54 mbar, about 53 mbar, about 52 mbar, about 51 mbar, about 50 mbar, about 49 mbar, about 48 mbar, about 47 mbar, about 46 mbar, about 45 mbar, about 44 mbar, about 43 mbar, about 42 mbar, about 41 mbar, about 40 mbar, about 39 mbar, about 38 mbar, about 37 mbar, about 36 mbar, about 35 mbar, about 34 mbar, about 33 mbar, about 32 mbar, about 31 mbar, about 30 mbar, about 29 mbar, about 28 mbar, about 27 mbar, about 26 mbar, about 25 mbar, about 24 mbar, about 23 mbar, about 22 mbar, about 21 mbar, about 20 mbar, about 19 mbar, about 18 mbar, about 17 mbar, about 16 mbar, about 15 mbar, about 14 mbar, about 13 mbar, about 12 mbar, about 11 mbar, about 10 mbar, about 9 mbar, about 8 mbar, about 7 mbar, about 6 mbar, about 5 mbar, about 4 mbar, about 3 mbar, about 2 mbar, or about 1 mbar.

As used herein, the terms "purge" and "purging" refer to replacing the atmospheric air or vacuum above the container solution with a defined gas. Preferably the container solution is purged with a soluble gas. In certain embodiments, purging is filling the environment surrounding the container and/or in the container with the soluble gas. Preferably purging is conducted at ambient pressure or about 1 atmosphere.

As used herein, the term "soluble gas" refers to any gas which dissolves into an aqueous solution. A soluble gas has a greater capacity to dissolve into an aqueous solution than atmosphere. A soluble gas used in the present invention may be a non-reactive gas or an inert gas. Suitable soluble gases include, but are not limited to: carbon dioxide, gaseous water, gaseous ethanol and gaseous formic acid. In one embodiment, the inert gas is carbon dioxide.

In one embodiment the temperature of the soluble gas is at about room temperature. Higher temperatures may also be useful since a higher gas temperature will reduce initial dissolution of the gas into the aqueous solution during the filling and stoppering process. In another embodiment, the soluble gas is at a temperature from about 20° C. to about 90° C. In another embodiment, the temperature of the soluble gas does not exceed about 90° C., about 85° C., about 80° C., about 75° C., about 70° C., about 65° C., about 60° C., about 55° C., about 50° C., about 45° C., about 40° C., about 35° C., about 30° C., about 25° C., or about 20° C.

In another embodiment, the soluble gas is a pharmaceutical grade soluble gas. In another embodiment, the soluble gas has purity of at least 90.000%, 91.000%, 92.000%, 93.000%, 94.000%, 95.000%, 96.000%, 97.000%, 98.000%, 98.500%, 98.250%, 98.500%, 98.750%, 99.000%, 99.100%, 99.200%, 99.300%, 99.400%, 99.500%, 99.600%, 99.700%, 99.800%, 99.900%, 99.910%, 99.920%, 99.930%, 99.940%, 99.950%, 99.960%, 99.970%, 99.980%, 99.990%, 99.991%, 99.992%, 99.993%, 99.994%, 99.995%, 99.996%, 99.997%, 99.998%, or 99.999%.

In another embodiment, the soluble gas is provided in a gas cylinder. In a further embodiment, gas cylinders are not switched during the methods of the present invention. In another embodiment, a single source of soluble gas (i.e. a single gas cylinder) is used to provide the soluble gas for a method of the present invention.

In one embodiment, carbon dioxide is provided as gas (e.g. in gas cylinders). In another embodiment, carbon dioxide is provided as liquid carbon dioxide and vaporized to gas as needed prior to use in the methods herein. In another embodiment, the carbon dioxide pharmaceutical grade, at least 99% pure, room temperature, and provided as a gas. In a further embodiment, the carbon dioxide is at least 99.5% pure. In yet a further embodiment, the carbon dioxide is at least 99.9% pure. In a still a further embodiment, the carbon dioxide is at least 99.998% pure.

As used herein, the term "non-reactive gas" refers to any gas which does not readily react with other compounds. A non-reactive gas is generally non-oxidizing and non-hydrolyzing. A gas has a tendency for non-reactivity is due to the valence, the outermost electron shell, being complete. Non-reactive gases include inert gases and nitrogen ($N_2$).

As used herein, the term "inert gas" refers to any gas which does not readily undergo chemical reactions. Inert gases are non-oxidizing and non-hydrolyzing. Preferably an inert gas used in the present invention readily dissolves in water. Inert gases comprise noble gases (helium, neon, argon, krypton, xenon, radon), and nitrogen ($N_2$).

As used herein, the term "stopper" refers to any article capable of preventing the aqueous drug substance solution from exiting the open end of the container.

As used herein, the term "inserting a stopper" refers to placing a stopper in the open end of the container so as to prevent the aqueous drug substance solution from exiting the open end of the container. Preferably, the stopper is inserted such that the leading edge of the stopper is at least 2 millimeters below the distal end of the open end of the container. The "leading edge" of the stopper refers to the extreme end of the stopper that first enters the chamber of the container as the stopper is being inserted. The stopper may be inserted under atmospheric pressure or under a pressure vacuum. If the stopper is inserted under a pressure vacuum, preferably the pressure vacuum is at a pressure of 700 Torr or less.

As used herein "headspace" refers to the area within the chamber of the container between the aqueous drug substance solution and the stopper when the open end of the container is oriented away from the pull of gravity.

In one embodiment of the present invention, the headspace created in a container when closed or stoppered, but prior to incubation, comprises at least about 70%, 75%, 80%, 85%, 90%, 91%, 92%, 93%, 94%, 95%, 96%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% soluble gas.

In another embodiment, the headspace represents about 0.5 mL, about 0.4 mL, about 0.3 mL, about 0.2 mL, about 0.19 mL, about 0.16 mL, about 0.13 mL, about 0.1 mL, about 0.09 mL, about 0.08 mL, about 0.07 mL, about 0.06 mL, about 0.05 mL, about 0.04 mL, about 0.03 mL, about 0.025 mL, or about 0.01 mL, more preferably about 40%, about 35%, about 30%, about 25%, about 20%, about 15%, about 12%, about 10%, about 9%, about 8%, about 7%, about 6%, about 5%, about 4%, about 3%, about 2%, about 1.5%, about 1%, about 0.75%, about 0.5%, about 0.25%, or about 0.1% of the volume of the container solution, more preferably less than 0.5%, preferably less than 0.001%, more preferably 0.0% of the total volume of the container following storage at a temperature below the temperature of the stoppering step or the closing step. In other embodiments, the headspace represents more than 1% of the total volume of the container prior to storage at a temperature below the temperature of the stoppering step or the closing step.

In another embodiment, the headspace is defined as the distance between the top of the container solution and the stopper when the open end of the container is oriented away from the pull of gravity. In yet a further embodiment, the container is a syringe. In yet a further embodiment, the headspace in the syringe is: less than or equal to about 10 mm, 9 mm, 8 mm, 7 mm, 6 mm, 5 mm, 4 mm, 3 mm, 2 mm, or 1 mm; or about 10 mm, about 9 mm, about 8 mm, about 7 mm, about 6 mm, about 5 mm, about 4 mm, about 3 mm, about 2 mm, or about 1 mm.

As used herein, the term "no detectable headspace" refers to a closed container comprising aqueous drug substance solution in which no headspace can be detected by optical means. Examples of containers with no detectable headspace include containers with no headspace detectable by human vision, no headspace, and zero headspace.

As used herein, the term "no headspace" or "zero headspace" refers to a container comprising aqueous drug substance solution in which no headspace can be detected using the methods of the present invention. Such methods include visibly observing the presence or absence of a headspace and subjecting the container to reduced atmospheric pressure and observing whether or not a headspace forms. Observations may be by naked eye or magnification up to 10×.

As used herein the term "stable" or "stabilized" refers to an aqueous drug substance solution that does not lose more than 20%, 15%, 10%, or 5% of its activity relative to activity of the composition at the beginning of storage. The term also should be understood to mean that the aqueous drug substance solution is at least comparable to, and alternatively better than commercially available compositions of the same drug substance, in terms of its ability to resist chemical and physical alteration. Chemical alteration includes, but is not limited to, hydrolysis, proteolysis, deamidation, oxidation, racemization, beta-elimination, and methylation. For example, a drug substance in a container without a headspace will not oxidize as a result of the lack of oxygen. Therefore, a drug substance in a container without a headspace is more stable than the same drug substance in a container with a headspace where it can be oxidized. Physical alteration, resulting from mechanical or other stresses, includes, but is not limited to, conformational changes, precipitation, denaturation, adsorption to surfaces, formation of particulates (visible and sub-visible particles), protein aggregates, and/or protein fragments which may occur during formulation, manufacturing, packaging, storage, shipping, transport, handling, or administration. In one embodiment, a stable aqueous solution is a solution meeting the U.S. Pharmacopeial Convention (USP) reference standard 787 titled "Subvisible Particulate Matter In Therapeutic Protein Injections." Cut-offs include: If the container volume is <100 mL, the solution has less than 6000 particles/container >10 micrometer (μm) in size and 600 particles/container >25 μm in size; and if the container volume is >100 mL; the solution has less than 25 particles/mL >10 μm in size and 3 particles/mL >25 μm in size.

In one embodiment, a stable aqueous solution is a solution having less than about 6000 sub-visible particles ≥10 μm in size per milliliter of solution. In another embodiment, a stable aqueous solution is a solution having less than about 600 sub-visible particles ≥25 micrometer μm in size per milliliter of solution. In yet another embodiment, a stable aqueous solution is a solution having less than about 6000 sub-visible particles ≥10 μm in size per 0.8 milliliter of solution. In still yet another embodiment, a stable aqueous solution is a solution having less than about 600 sub-visible particles ≥25 micrometer μm in size per 0.8 milliliter of solution.

Stability of a drug substance in an aqueous solution may also be defined as the percentage of monomer, aggregate, or fragment, or combinations thereof, of the protein in the formulation. A drug substance "retains its physical stability" in a solution if it shows substantially no signs of aggregation, precipitation and/or denaturation upon visual examination of color and/or clarity, or as measured by UV light scattering or by size exclusion chromatography. In one embodiment of the invention, a stable aqueous solution is a solution having less than about 10%, or less than about 5% of the protein being present as aggregate in the solution.

As used herein, the term "amino acid" refers to a naturally occurring or functionalized amino acid. Amino acids include, but are not limited to, histidine, glycine, methionine, serine, proline, and arginine and combinations thereof.

In one embodiment, the concentration of amino acid is from about 1 mM to about 500 mM. In one embodiment, the amino acid is present at a concentration from about 10 mM to about 400 mM. In another embodiment, the concentration of amino acid is from about 10 mM to about 300 mM. In another embodiment, the amino acid is present at a concentration from about 20 mM to about 200 mM. In another embodiment, the amino acid is present at about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 205 mM, about 210 mM, about 215 mM, about 220 mM, about 225 mM, about 230 mM, about 235 mM, about 240 mM, about 245 mM, about 250 mM, about 255 mM, about 260 mM, about 265 mM, about 270 mM, about 275 mM, about 280 mM, about 285 mM, about 290 mM, about 295 mM, about 300 mM about 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 405 mM, about 410 mM, about 415 mM, about 420 mM, about 425 mM, about 430 mM, about 435 mM, about 440 mM, about 445 mM, about 450 mM, about 455 mM, about 460 mM, about 465 mM, about 470 mM, about 475 mM, about 480 mM, about 485 mM, about 490 mM, about 495 mM, or about 500 mM.

In another embodiment, the total amount of amino acid does not exceed about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 205 mM, about 210 mM, about 215 mM, about 220 mM, about 225 mM, about 230 mM, about 235 mM, about 240 mM, about 245 mM, about 250 mM, about 255 mM, about 260 mM, about 265 mM, about 270 mM, about 275 mM, about 280 mM, about 285 mM, about 290 mM, about 295 mM, about 300 mM, about 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 405 mM, about 410 mM, about 415 mM, about 420 mM, about 425 mM, about 430 mM, about 435 mM, about 440 mM, about 445 mM, about 450 mM, about 455 mM, about 460 mM, about 465 mM, about 470 mM, about 475 mM, about 480 mM, about 485 mM, about 490 mM, about 495 mM, about 500 mM, about 600 mM, about 650 mM, about 700 mM, about 750 mM, about 800 mM, about 850 mM, about 900 mM, about 950 mM, or about 1000 mM.

As used herein, the term "buffer" refers to a solution that resists changes in pH by the action of its acid-base conjugate components. A weak acid and its conjugate base is a buffer. A weak base and its conjugate acid is a buffer. A buffer of this invention has a pH in the range from about 4.0 to about 9.0; from about pH 5.0 to about 8.0; or from about pH 5.5 to about 7.5. A pH of any point in between the above ranges is also contemplated. Buffers include, but are not limited to, phosphate, pyrophosphate, citrate, acetate, glutamate, gluconate, histidine, succinate, adipate, maleate, and tartrate, and combinations thereof.

In one embodiment, the concentration of buffer is from about 1 mM to about 150 mM. In another embodiment, the concentration of buffer is from about 5 mM to about 50 mM. In another embodiment the concentration of the buffer comprises about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, and about 100 mM.

As used herein, the term "stabilizer" refers to pharmaceutically acceptable excipient which imparts stability to an aqueous solution or a drug substance in an aqueous solution. A stabilizer includes, but is not limited to, amino acid, salt, polymers, chelating agents (e.g. DPTA, EDTA) and metal ion.

As used herein, the term "cyclodextrin" refers to cyclic oligosaccharides. Cyclodextrins suitable for use in the present invention include, but are not limited to, alpha-, beta- and gamma-cyclodextrins, αCD, βCD, and γCD, respectively. Preferred cyclodextrins include derivatized cyclodextrins. Derivatized cyclodextrin many contain a range of derivatives attached through the three available hydroxyl groups on each glucopyranose unit. The terms substituted and derivitized are used to refer to hydroxyl groups that have been replace with another group. Up to 18 (αCD), 21 (βCD), or 24 (γCD) degrees of substitution may be achieved, with numerous positional and regioisomers possible. Examples of derivatized cyclodextrins include, but are not limited to, methyl-beta-cyclodextrins ("MβCD"); randomly methylated-beta-cyclodextrin ("RMβCD"); Sulfobutylether-beta-cyclodextrins ("SBEβCD") (e.g. Captisol® which has six to seven sulfobutyl ether groups per cyclodextrin molecule); hydroxypropyl-beta-cyclodextrins ("HPβCD") (e.g. Cavasol® W7 HP HPβCD, Cavitron™ W7 HP7 HPβCD, and Cavitron™ W7 HP5 HPβCD) including 2-hydroxypropyl-beta-cyclodextrin; hydroxypropyl-gamma-cyclodextrins ("HPγCD"), including 2-hydroxypropyl-gamma-cyclodextrins. A preferred cyclodextrin is hydroxypropyl-beta-cyclodextrin ("HPβCD").

The hydroxypropyl beta cyclodextrin is a partially substituted poly (hydroxypropyl) ether beta cyclodextrin. In one embodiment, the number of hydroxypropyl groups per anhydroglucose unit, expressed as molar substitution is no less than (NLT) 0.40 to no more than (NMT) 1.50. Put otherwise, the average substitution of HPβCD is about 0.4 to about 1.50. In another embodiment, the average substitution of HPβCD is at least about 0.61. HPβCD with higher degree of substitution provide better protection for proteins.

In another embodiment, the average substitution of HPβCD is about 0.4, about 0.41, about 0.42, about 0.43, about 0.44, about 0.45, about 0.46, about 0.47, about 0.48, about 0.49, about 0.5, about 0.51, about 0.52, about 0.53, about 0.54, about 0.55, about 0.56, about 0.57, about 0.58, about 0.59, about 0.6, about 0.61, about 0.62, about 0.63, about 0.64, about 0.65, about 0.66, about 0.67, about 0.68, about 0.69, about 0.7, about 0.71, about 0.72, about 0.73, about 0.74, about 0.75, about 0.76, about 0.77, about 0.78, about 0.79, about 0.8, about 0.81, about 0.82, about 0.83, about 0.84, about 0.85, about 0.86, about 0.87, about 0.88, about 0.89, about 0.9, about 0.91, about 0.92, about 0.93, about 0.94, about 0.95, about 0.96, about 0.97, about 0.98, about 0.99, about 1, about 1.01, about 1.02, about 1.03, about 1.04, about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, about 1.31, about 1.32, about 1.33, about 1.34, about 1.35, about 1.36, about 1.37, about 1.38, about 1.39, about 1.4, about 1.41, about 1.42, about 1.43, about 1.44, about 1.45, about 1.46, about 1.47, about 1.48, about 1.49, about 1.5, about 1.51, about 1.52, about 1.53, about 1.54, about 1.55, about 1.56, about 1.57, about 1.58, about 1.59, about 1.6, about 1.61, about 1.62, about 1.63, about 1.64, about 1.65, about 1.66, about 1.67, about 1.68, about 1.69, about 1.7, about 1.71, about 1.72, about 1.73, about 1.74, about 1.75, about 1.76, about 1.77, about 1.78, about 1.79, about 1.8, about 1.81, about 1.82, about 1.83, about 1.84, about 1.85, about 1.86, about 1.87, about 1.88, about 1.89, about 1.9, about 1.91, about 1.92, about 1.93, about 1.94, about 1.95, about 1.96, about 1.97, about 1.98, about 1.99, about 2, about 2.01, about 2.02, about 2.03, about 2.04, about 2.05, about 2.06, about 2.07, about 2.08, about 2.09, about 2.1, about 2.11, about 2.12, about 2.13, about 2.14, about 2.15, about 2.16, about 2.17, about 2.18, about 2.19, about 2.2, about 2.21, about 2.22, about 2.23, about 2.24, about 2.25, about 2.26, about 2.27, about 2.28, about 2.29, about 2.3, about 2.31, about 2.32, about 2.33, about 2.34, about 2.35, about 2.36, about 2.37, about 2.38, about 2.39, about 2.4, about 2.41, about 2.42, about 2.43, about 2.44, about 2.45, about 2.46, about 2.47, about 2.48, about 2.49, about 2.5, about 2.51, about 2.52, about 2.53, about 2.54, about 2.55, about 2.56, about 2.57, about 2.58, about 2.59, about 2.6, about 2.61, about 2.62, about 2.63, about 2.64, about 2.65, about 2.66, about 2.67, about 2.68, about 2.69, about 2.7, about 2.71, about 2.72, about 2.73, about 2.74, about 2.75, about 2.76, about 2.77, about 2.78, about 2.79, about 2.8, about 2.81, about 2.82, about 2.83, about 2.84, about 2.85, about 2.86, about 2.87, about 2.88, about 2.89, about 2.9, about 2.91, about 2.92, about 2.93, about 2.94, about 2.95, about 2.96, about 2.97, about 2.98, about 2.99, or about 3.

The degree of substitution can be ascertained using conventional methods such as NMR and HPLC.

In one embodiment, the cyclodextrin meets USP and/or EP requirements.

In a another embodiment the amount of HPβCD is from about 0.1% to about 50% w/v, about 3% to about 21% w/v, about 6% to about 12% w/v, about greater than 10 mM, from about greater than 10 mM to about 150 mM, from about 25 mM to about 100 mM, from about 50 mM to about 75 mM, about 25 mM, about 50 mM, about 70 mM or about 75 mM.

In a further embodiment, the amount of HPβCD is about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, about 100 mM, about 101 mM, about 102 mM, about 103 mM, about 104 mM, about 105 mM, about 106 mM, about 107 mM, about 108 mM, about 109 mM, about 110 mM, about 111 mM, about 112 mM, about 113 mM, about 114 mM, about 115 mM, about 116 mM, about 117 mM, about 118 mM, about 119 mM, about 120 mM, about 121 mM, about 122 mM, about 123 mM, about 124 mM, about 125 mM, about 126 mM, about 127 mM, about 128 mM, about 129 mM, about 130 mM, about 131 mM, about 132 mM, about 133 mM, about 134 mM, about 135 mM, about 136 mM, about 137 mM, about 138 mM, about 139 mM, about 140 mM, about 141 mM, about 142 mM, about 143 mM, about 144 mM, about 145 mM, about 146 mM, about 147 mM, about 148 mM, about 149 mM, about 150 mM, about 151 mM, about 152 mM, about 153 mM, about 154 mM, about 155 mM, about 156 mM, about 157 mM, about 158 mM, about 159 mM, about 160 mM, about 161 mM, about 162 mM, about 163 mM, about 164 mM, about 165 mM, about 166 mM, about 167 mM, about 168 mM, about 169 mM, about 170 mM, about 171 mM, about 172 mM, about 173 mM, about 174 mM, about 175 mM, about 176 mM, about 177 mM, about 178 mM, about 179 mM, about 180 mM, about 181 mM, about 182 mM, about 183 mM, about 184 mM, about 185 mM, about 186 mM, about 187 mM, about 188 mM, about 189 mM, about 190 mM, about 191 mM, about 192 mM, about 193 mM, about 194 mM, about 195 mM, about 196 mM, about 197 mM, about 198 mM, about 199 mM, or about 200 mM.

Cyclodextrins have pharmaceutical utility as stabilizers and solubilizers which prevent protein aggregation. Cyclodextrins non-covalently complex with proteins through association of the cyclodextrin hydrophobic cavity with hydrophobic amino acids (e.g. Phe, Tyr, Trp) on the protein surface. Unlike non-ionic surfactants, cyclodextrins do not form micelles and do not significantly reduce surface tension at liquid-air interfaces. Additionally, cyclodextrins are effective at higher concentration than non-ionic surfactants. Thus, the stabilizing effect of cyclodextrins on proteins, and protein formulations, is understood to be a result of direct interaction with the protein rather than a surface effect.

As used herein, the term "polyol" means an alcohol containing multiple hydroxyl groups. Examples of polyols include, but are not limited to, mannitol, sorbitol, trehalose, and others.

As used herein, the term "salt" means pharmaceutically acceptable salts. Salt includes, but is not limited to, NaCl, KCl, $Na_2SO_4$, $MgCl_2$, $MgSO_4$, $ZnCl_2$ and $CaCl_2$. In one embodiment, the salt comprises a divalent cation. Divalent cations include, but are not limited to, Ca', Mg'. In one embodiment, salt with a divalent cation interacts with buffer, excipient or protein, and forms a complex. This interaction enhances the stability of protein under storage and stress conditions.

As used herein, the term "sugar" means monosaccharides, disaccharides, and polysaccharides. Examples of sugars include, but are not limited to, sucrose, glucose, dextrose, sorbitol, maltose, lactose, and others.

As used herein, the term "surfactant" refers to compounds such as polyoxyethylensorbitan fatty acid esters (e.g. polysorbates, Tween®), polyoxyethylene alkyl ethers (e.g. Brij®), alkylphenylpolyoxyethylene ethers (e.g. Triton-X®), polyoxyethylene-polyoxypropylene copolymers (e.g. poloxamers, Pluronic®), and sodium dodecyl sulfate. Surfactants are characterized by the ability to form micelles, preferentially accumulate at liquid-air interfaces, and disrupt and/or displace protein at liquid-air interfaces. As result, surfactants significantly reducing the surface tension of liquids.

Techniques for determining if a substance forms micelles include surface tension measurements and extrinsic fluorescence spectroscopy. Surface tension measurement techniques include tensiometry and pendant drop methods. Extrinsic fluorescence spectroscopy measures the changes in the emission spectrum of a dye, indicating the formation of the micelle as the local environment around dye changes from hydrophilic to hydrophobic. Non-surfactant excipients of the present invention (e.g. HPβCD) do not form micelles at the concentrations used herein.

As used herein, the term "tonicity modifier" or "tonicity agent" refers any molecule that contributes to the osmolality of a solution. Note that the tonicity modifier may also provide some degree of conformational or colloidal stabilization as well. The osmolality of a pharmaceutical composition is preferably adjusted to maximize the active ingredient's stability and/or to minimize discomfort to the patient upon administration. It is generally preferred that a pharmaceutical composition for direct administration to a patient be isotonic with serum, i.e., having the same or similar osmolality, which is achieved by addition of a tonicity modifier. However, hypertonic formulations which would then be diluted in an isotonic vehicle are also within the scope of this invention. Examples of tonicity modifiers suitable for modifying osmolality include, but are not limited to amino acids (e.g., cysteine, arginine, histidine and glycine), salts (e.g., sodium chloride, potassium chloride and sodium citrate) and/or nonelectrolytes (e.g., sugars or polyols, such as, for example, sucrose, glucose and mannitol).

In one embodiment, the concentration of the tonicity modifier in the formulation is preferably between about 1 mM to about 1 M, more preferably about 50 mM to about 500 mM. Tonicity modifiers are well known in the art and are manufactured by known methods and available from commercial suppliers.

As used herein, the term "substantially free" means that either no substance is present or only minimal, trace amounts of the substance are present which do not have any substantial impact on the properties of the composition. In a particular embodiment, a composition is substantially free of a substance if at least 95%, 96%, 97%, 98%, 99%, 99.5%, or 99.8% of the substance has been removed. In another embodiment, substantially free means the substance is not present in amount sufficient to perform a function in composition for which a skilled artisan would use the substance. If reference is made to no amount of a substance, or a composition being free of a substance, it should be understood as "no detectable amount."

Methods for Making Containers with Aqueous Solutions and Zero Headspace

Headspace in a container allows increase of mechanical stress on the drug product as well as provides a gas-solution interface. Both mechanical stress and gas-solution interfaces are detrimental to the stability of protein drug substances. The present invention is directed to providing containers with zero headspace to reduce the mechanical stress and eliminate the gas-solution interface thus providing a more stable protein drug substance.

In one embodiment, the present invention is directed to a method for preparing a container with zero headspace comprising an aqueous drug substance solution, the method comprising:
 a) providing a container with a closed end and open end;
 b) providing a bulk aqueous drug substance solution;
 c) filling the container via the open end with the bulk aqueous drug substance solution to create a container solution;
 d) degassing the container solution via a pressure vacuum;
 e) purging the container with at least one soluble gas;
 f) optionally repeating the degassing and purging steps;
 g) degassing the container solution via a pressure vacuum and while under vacuum, inserting a stopper into the open end of the container creating a headspace; and
 h) storing the container at a temperature below the temperature at which the the stoppering step occurred,
wherein the stopper can move within the container while maintaining a seal, and wherein the storage step results in the container having zero headspace.

In certain embodiments, the present invention is directed to methods of filling a container to reduce headspace comprising, consisting of or consisting essentially of:
 a) providing a container with a closed end and an open end;
 b) providing a bulk aqueous drug substance solution;
 c) optionally and preferably degassing the bulk aqueous drug substance solution;
 d) filling the container via the open end with the bulk aqueous drug substance solution to create a container solution, preferably the container is filled to from about 5% to about 95% of the total volume of the container;
 e) optionally degassing the container solution, preferably degassing occurs via a pressure vacuum, more preferably degassing occurs via a pressure vacuum wherein the pressure is 700 Torr or less, most preferably degassing occurs via a pressure vacuum wherein the pressure is 700 Torr or less and degassing occurs for 60 minutes or less;
 f) purging the container with at least one soluble gas at a time selected from the group consisting of prior to the filling step, during the filling step, after the filling step and a combination thereof, preferably the at least one soluble gas is selected from carbon dioxide, gaseous water, gaseous ethanol and gaseous formic acid, more preferably carbon dioxide, wherein optionally purging the container during the filling step occurs under a pressure vacuum, preferably a pressure vacuum wherein the pressure is 700 Torr or less;
 g) inserting a stopper into the open end of the container creating a headspace; and
 h) storing the container at a temperature below the temperature of the stoppering step, preferably storage occurs for at least 4 days,
wherein the stopper can move within the container while maintaining a seal and wherein the storage step reduces the headspace to less than 0.1%, preferably less than 0.01%, more preferably 0.0% of the total volume of the container, and optionally wherein the headspace created during the inserting step represents more than 1% of the total volume of the container.

In certain other embodiments, the present invention is directed to methods of filling a container to reduce headspace comprising, consisting of or consisting essentially of:
 a) providing a container with a closed end and an open end;
 b) providing a bulk aqueous drug substance solution;
 c) filling the container via the open end with the bulk aqueous drug substance solution to create a container solution;
 d) degassing the container solution at pressure of about 250 Torr or less for at least about 2 minutes;
 e) purging the container with at least one soluble gas at ambient pressure;
 f) repeating the degassing and purging steps;
 g) inserting a stopper into the open end of the container creating a headspace; and
 h) storing the container at a temperature below the temperature of the stoppering step,
wherein the stopper can move within the container while maintaining a seal; stoppering occurs in an environment consisting essentially of the soluble gas; and the storage step reduces the headspace to less than 0.1% of the volume of the container.

In certain other embodiments, the present invention is directed to methods of filling a pliable container to reduce headspace comprising, consisting of or consisting essentially of:
 a) providing a pliable container comprising an opening;
 b) providing a bulk aqueous drug substance solution;
 c) filling the pliable container via the opening with the bulk aqueous drug substance solution to create a container solution;
 d) purging the pliable container with at least one soluble gas at a time selected from the group consisting of prior to the filling step, during the filling step, after the filling step and a combination thereof;
 e) closing the opening of the pliable container creating a headspace; and
 f) storing the pliable container at a temperature below the temperature of the closing step, wherein the storage step reduces the headspace to less than 0.1% of the volume of the pliable container.

In certain other embodiments, the present invention is directed to methods of filling a pliable container to reduce headspace comprising, consisting of or consisting essentially of:
 a) providing a pliable container with a closed end and an open end;
 b) providing a bulk aqueous drug substance solution;
 c) filling the pliable container via the open end with the bulk aqueous drug substance solution to create a container solution;
 d) degassing the container solution at pressure of about 250 Torr or less for at least about 2 minutes;
 e) purging the pliable container with at least one soluble gas at ambient pressure;
 f) repeating the degassing and purging steps;
 g) closing the open end of the container creating a headspace; and
 h) storing the pliable container at a temperature below the temperature of the closing step,
wherein closing occurs in an environment consisting essentially of the soluble gas; and the storage step reduces the headspace to less than 0.1% of the volume of the pliable container.

In certain other embodiments, the present invention is directed to methods of filling a container to reduce headspace comprising, consisting of or consisting essentially of:
 a) filling a container via an open end with a degassed bulk aqueous drug substance solution to create a container solution;
 b) purging the container with at least one soluble gas at a time selected from the group consisting of prior to the filling step, during the filling step, after the filling step and a combination thereof;
 c) inserting a stopper into the open end of the container creating a headspace; and
 d) allowing absorption of the headspace into the container solution, thereby reducing the headspace,
wherein the stopper can move within the container while maintaining a seal; and the headspace is reduced to less than about 0.1% of the volume of the container.

In certain other embodiments, the present invention is directed to methods of filling a container to reduce headspace comprising, consisting of or consisting essentially of:
 a) filling a container via an open end with a degassed bulk aqueous drug substance solution to create a container solution;
 b) degassing the container solution at pressure of about 250 Torr or less for at least about 2 minutes;
 c) purging the container with at least one soluble gas at ambient pressure;
 d) repeating the degassing and purging steps;
 e) inserting a stopper into the open end of the container creating a headspace; and
 f) storing the container at a temperature below the temperature of the stoppering step,
wherein the stopper can move within the container while maintaining a seal; stoppering occurs in an environment consisting essentially of the soluble gas; and the storage step reduces the headspace to less than 0.1% of the volume of the container.

In certain other embodiments, the present invention is directed to methods of stabilizing an aqueous drug substance solution comprising, consisting of, or consisting essentially of:
 a) providing a container with a closed end and an open end;
 b) providing a bulk aqueous drug substance solution;
 c) optionally and preferably degassing the bulk aqueous drug substance solution, preferably degassing occurs via a pressure vacuum;
 d) filling the container via the open end with the bulk aqueous drug substance solution to create a container solution, preferably the container is filled to from about 5% to about 95% of the total volume of the container;
 e) optionally degassing the container solution, preferably degassing occurs via a pressure vacuum, more preferably degassing occurs via a pressure vacuum wherein the pressure is 700 Torr or less, most preferably degassing occurs via a pressure vacuum wherein the pressure is 700 Torr or less and degassing occurs for 60 minutes or less;
 f) purging the container with at least one soluble gas at a time selected from the group consisting of prior to the filling step, during the filling step, after the filling step and a combination thereof, preferably the inert gas is selected from carbon dioxide, gaseous water, gaseous ethanol and gaseous formic acid, more preferably carbon dioxide, wherein optionally purging the container during the filling step occurs under a pressure vacuum, preferably a pressure vacuum wherein the pressure is 700 Torr or less;
 g) inserting a stopper into the open end of the container creating a headspace; and
 h) storing the container at a temperature below the temperature of the stoppering step, preferably storage occurs for at least 4 days,
wherein the stopper can move within the container while maintaining a seal and wherein the storage step reduces the headspace to less than 0.1%, preferably less than 0.01%, more preferably 0.0% of the total volume of the container and optionally wherein the headspace created during the inserting step represents more than 1% of the total volume of the container.

In certain other embodiments, the present invention is directed to methods of stabilizing an aqueous drug substance solution comprising, consisting of, or consisting essentially of:
 a) providing a container with a closed end and an open end;
 b) providing a bulk aqueous drug substance solution;
 c) filling the container via the open end with the bulk aqueous drug substance solution to create a container solution;
 d) degassing the container solution at pressure of about 250 Torr or less for at least about 2 minutes;
 e) purging the container with at least one soluble gas at ambient pressure;
 f) repeating the degassing and purging steps;
 g) inserting a stopper into the open end of the container creating a headspace; and
 h) storing the container at a temperature below the temperature of the stoppering step,
wherein the stopper can move within the container while maintaining a seal; stoppering occurs in an environment consisting essentially of the soluble gas; and the storage step reduces the headspace to less than 0.1% of the volume of the container.

In certain other embodiments, the present invention is directed to methods of stabilizing an aqueous drug substance solution comprising, consisting of, or consisting essentially of:

a) providing a pliable container comprising an opening;
b) providing a bulk aqueous drug substance solution;
c) filling the pliable container via the opening with the bulk aqueous drug substance solution to create a container solution;
d) purging the pliable container with at least one soluble gas at a time selected from the group consisting of prior to the filling step, during the filling step, after the filling step and a combination thereof;
e) closing the opening of the pliable container creating a headspace; and
f) storing the pliable container at a temperature below the temperature of the closing step, wherein the storage step reduces the headspace to less than about 0.1% of the volume of the pliable container.

In certain other embodiments, the present invention is directed to methods of stabilizing an aqueous drug substance solution comprising, consisting of, or consisting essentially of:
a) providing a pliable container comprising an opening;
b) providing a bulk aqueous drug substance solution;
c) filling the container via the open end with the bulk aqueous drug substance solution to create a container solution;
d) degassing the container solution at pressure of about 250 Torr or less for at least about 2 minutes;
e) purging the container with at least one soluble gas at ambient pressure;
f) repeating the degassing and purging steps;
e) closing the opening of the pliable container creating a headspace; and
f) storing the pliable container at a temperature below the temperature of the closing step, wherein closing occurs in an environment consisting essentially of the soluble gas; and the storage step reduces the headspace to less than about 0.1% of the volume of the pliable container.

In certain other embodiments, the present invention is directed to methods of stabilizing an aqueous drug substance solution comprising, consisting of, or consisting essentially of:
a) filling a container via an open end with a degassed bulk aqueous drug substance solution to create a container solution;
b) purging the container with at least one soluble gas at a time selected from the group consisting of prior to the filling step, during the filling step, after the filling step and a combination thereof;
c) inserting a stopper into the open end of the container creating a headspace; and
d) allowing absorption of the headspace into the container solution, thereby reducing the headspace, wherein the stopper can move within the container while maintaining a seal; and the headspace is reduced to less than 0.1% of the volume of the container.

In certain other embodiments, the present invention is directed to methods of stabilizing an aqueous drug substance solution comprising, consisting of, or consisting essentially of:
a) filling a container via an open end with a degassed bulk aqueous drug substance solution to create a container solution;
b) degassing the container solution at pressure of about 250 Torr or less for at least about 2 minutes;
c) purging the container with at least one soluble gas at ambient pressure;
d) repeating the degassing and purging steps;
e) inserting a stopper into the open end of the container creating a headspace; and
f) allowing absorption of the headspace into the container solution, thereby reducing the headspace, wherein the stopper can move within the container while maintaining a seal; stoppering occurs in an environment consisting essentially of the soluble gas; and the headspace is reduced to less than 0.1% of the volume of the container.

In certain other embodiments, the present invention is directed to a container comprising, consisting of, or consisting essentially of an aqueous drug substance solution with reduced headspace prepared by any of the preceding methods of filling a container to reduce headspace.

In certain other embodiments, the present invention is directed to a pliable container comprising, consisting of, or consisting essentially of an aqueous drug substance solution with reduced headspace prepared by any of the preceding methods of filling a pliable container to reduce headspace.

In certain other embodiments, the present invention is directed to a container comprising, consisting of, or consisting essentially of a stable aqueous drug substance solution with reduced headspace prepared by any of the preceding methods of stabilizing an aqueous drug substance solution.

In certain other embodiments, the present invention is directed to a pliable container comprising, consisting of, or consisting essentially of a stable aqueous drug substance solution with reduced headspace prepared by any of the preceding methods of stabilizing an aqueous drug substance solution.

In certain other embodiments, the present invention is directed to a container comprising, consisting of, or consisting essentially of an aqueous drug substance solution wherein the container has no visibly detectable headspace at room temperature.

In certain other embodiments, the present invention is directed to a container comprising, consisting of, or consisting essentially of an aqueous drug substance solution wherein the container has no visibly detectable headspace at room temperature; and the aqueous drug substance solution comprises adalimumab, does not contain surfactant, and optionally does not contain polyol.

In another embodiment, the present invention is directed to a method for detecting headspace in a container comprising, consisting of, or consisting essentially of an aqueous drug substance solution comprising, consisting of, or consisting essentially of:
a) incubating the container suspected of having no headspace at room temperature;
b) subjecting the container to a pressure vacuum; and
c) inspecting the container for presence of a headspace, wherein the presence of a headspace in step c) indicates a headspace that was not visible prior to subjecting the container to a pressure vacuum.

In certain other embodiments the container is a syringe.

In certain other embodiments the container is closed with a delivery device, more preferably a needle.

In certain other embodiments the headspace is reduced by absorbance of the headspace by the container solution.

In certain other embodiments, surfactant in the bulk aqueous drug substance solution is present a concentration below about 0.1%, below about 0.05%, below about 0.01%. In another embodiment, the bulk aqueous drug substance solution is free or substantially free of surfactant.

In certain other embodiments, the volume of the container solution is at least about 5%, 10%, 25%, 40%, 50%, 60%, 70%, 80%, 90%, 95%, 97%, 98%, or 99% of the volume of the container or at most about 60%, about 65%, about 70%, about 75%, about 80%, about 85%, about 90%, about 93%, about 95%, about 97%, or about 98% of the volume of the container or about 0.1 mL to about 2 mL, about 0.25 mL to about 1.5 mL, about 0.5 mL to about 1 mL, about 0.1 mL, about 0.25 mL, about 0.5 mL, about 1 mL, about 1.5 mL, about 2 mL, about 1 L, about 5 L, about 10 L, about 15 L, or about 20 L.

In certain other embodiments, the storing step occurs at least about 1 hour, 2 hours, 4 hours, 8 hours, 12 hours, 24 hours, 36 hours, 48 hours, 60 hours, 72 hours, 84 hours, or 96 hours.

Degassing

In one embodiment, degassing occurs at vacuum pressure disclosed herein.

In another embodiment, degassing occurs at about 40 mbar for about 2 minutes. In another embodiment, degassing occurs at about 40 mbar for about 3 minutes.

In another embodiment of the present invention, vacuum applied to a solution does not reduce the pressure below the vapor pressure of the solution. In another embodiment, when an aqueous solution is subjected to a pressure vacuum, the pressure is below ambient air pressures and above the boiling point pressure of the aqueous solution. The pressure at which an aqueous solution boils is readily determined by one of ordinary skill in the art.

In one embodiment, the boiling point pressure of the aqueous solution is about 30 mbar, about 29 mbar, about 28 mbar, about 27 mbar, about 26 mbar, about 25 mbar, about 24 mbar, about 23 mbar, about 22 mbar, about 21 mbar, or about 20 mbar. In a further embodiment, the boiling point pressure of the aqueous solution is about 22 mbar. In yet another embodiment, the pressure is about 50% above, about 49% above, about 48% above, about 47% above, about 46% above, about 45% above, about 44% above, about 43% above, about 42% above, about 41% above, about 40% above, about 39% above, about 38% above, about 37% above, about 36% above, about 35% above, about 34% above, about 33% above, about 32% above, about 31% above, about 30% above, about 29% above, about 28% above, about 27% above, about 26% above, about 25% above, about 24% above, about 23% above, about 22% above, about 21% above, about 20% above, about 19% above, about 18% above, about 17% above, about 16% above, about 15% above, about 14% above, about 13% above, about 12% above, about 11% above, about 10% above, about 9% above, about 8% above, about 7% above, about 6% above, about 5% above, about 4% above, about 3% above, about 2% above, or about 1% above the boiling point pressure of the aqueous solution.

In another embodiment, when an aqueous solution is subjected to a pressure vacuum, the pressure is below the boiling point pressure of the aqueous solution provided the pressures vacuum is applied for brief period of time to minimize or prevent boiling, spilling, or loss of the aqueous solution. In one embodiment, the pressure is selected from about 40 mbar, about 39 mbar, about 38 mbar, about 37 mbar, about 36 mbar, about 35 mbar, about 34 mbar, about 33 mbar, about 32 mbar, about 31 mbar, about 30 mbar, about 29 mbar, about 28 mbar, about 27 mbar, about 26 mbar, about 25 mbar, about 24 mbar, about 23 mbar, about 22 mbar, about 21 mbar, about 20 mbar, about 19 mbar, about 18 mbar, about 17 mbar, about 16 mbar, about 15 mbar, about 14 mbar, about 13 mbar, about 12 mbar, about 11 mbar, about 10 mbar, about 9 mbar, about 8 mbar, about 7 mbar, about 6 mbar, about 5 mbar, about 4 mbar, about 3 mbar, about 2 mbar, and about 1 mbar; and the pressure vacuum is applied for a period of time selected from about 20 seconds, about 19.5 seconds, about 19 seconds, about 18.5 seconds, about 18 seconds, about 17.5 seconds, about 17 seconds, about 16.5 seconds, about 16 seconds, about 15.5 seconds, about 15 seconds, about 14.5 seconds, about 14 seconds, about 13.5 seconds, about 13 seconds, about 12.5 seconds, about 12 seconds, about 11.5 seconds, about 11 seconds, about 10.5 seconds, about 10 seconds, about 9.5 seconds, about 9 seconds, about 8.5 seconds, about 8 seconds, about 7.5 seconds, about 7 seconds, about 6.5 seconds, about 6 seconds, about 5.5 seconds, about 5 seconds, about 4.5 seconds, about 4 seconds, about 3.5 seconds, about 3 seconds, about 2.5 seconds, about 2 seconds, about 1.5 seconds, about 1 seconds, and about 0.5 seconds. In one embodiment, a pressure vacuum at about 18 mbar pressure is applied for about 1.5 seconds. In another embodiment, a pressure vacuum at about 18 mbar pressure is applied for about 1 second. In yet another embodiment, a pressure vacuum at about 18 mbar pressure is applied for about 0.5 seconds.

Purging

In one embodiment of the invention, the container is purged with a soluble gas for sufficient time to achieve at least about 70%, 75%, 80%, 85%, 90%, 91%, 92%, 93%, 94%, 95%, 96%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% soluble gas in the container.

In another embodiment of the present invention, containers are purged with a soluble gas at a pressure of about 5 to 10 psi. Alternatively, containers are purged with a soluble gas at a pressure exceeding about 5 to 10 psi provided the enclosure in which the container is being purged comprises a pressure regulation feature (e.g. a backpressure shutoff) which is set to about 5 to 10 psi. In another embodiment of the present invention, the pressure applied to the container by soluble gas purging does not exceed about 43.5 psi.

Duration of Method Steps

In another embodiment of the invention, the duration that a vacuum is applied to a container, a container is purged with a soluble gas, or a solution is exposed to a soluble gas does not exceed about 5, 10, 15, 20, 25, 30, 35, 40, 45, 50, 55, 60, 65, 70, 75, 80, 85, 95, 100, 105, 110, 115, 120, 125, 130, 135, 140, 145, 150, 155, 160, 170, 175, 180, 210, 240, 270, 300, 330, 360, 390, 420, 450, 480, 510, 540, 570, 600, 630, 660, 690, 720, 750, 780, 810, 840, 870, 900, 930, 960, 990, 1020, 1050, 1080, 1110, 1140, 1170, 1200, 1230, 1260, 1290, 1320, 1350, 1380, 1410, 1440, 1470, 1500, 1530, 1560, 1590, 1620, 1650, 1680, 1710, 1740, 1770, or 1800 seconds; is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 95, 100, 105, 110, 115, 120, 125, 130, 135, 140, 145, 150, 155, 160, 170, 175, 180, 210, 240, 270, 300, 330, 360, 390, 420, 450, 480, 510, 540, 570, 600, 630, 660, 690, 720, 750, 780, 810, 840, 870, 900, 930, 960, 990, 1020, 1050, 1080, 1110, 1140, 1170, 1200, 1230, 1260, 1290, 1320, 1350, 1380, 1410, 1440, 1470, 1500, 1530, 1560, 1590, 1620, 1650, 1680, 1710, 1740, 1770, or 1800 seconds; or is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 145, 155, 160, 165, 170, 175, 180, 210, 240, 270, 300, 330, 360, 390, 420, 450, 480, 510, 540, 570, 600, 630, 660, 690, 720, 750, 780, 810, 840, 870, 900, 930, 960, 990, 1020, 1050, 1080, 1110, 1140, 1170, 1200, 1230, 1260, 1290, 1320, 1350, 1380, 1410, 1440, 1470, 1500, 1530, 1560, 1590, 1620, 1650, 1680, 1710, 1740, 1770, or 1800 seconds.

Vacuum Tubes

In another embodiment of the invention, a vacuum insertion tube used for inserting a stopper in a container may be categorized as a short or long vacuum insertion tube. Short vacuum insertion tubes are characterized by only being able to insert a stopper at the flange level of the container. Long vacuum insertion tubes are characterized by being able to insert a stopper in the container anywhere between the flange level of the container and the solution level.

Storing

Storing preferably occurs at a temperature below the temperature of the stoppering step or the closing step. More preferably storing occurs at a temperature from about −30° C. to about 15° C. without freezing the container solution, more preferably from above the freezing point of the container solution to about 15° C., more preferably from about 1° C. to about 10° C., more preferably from about 2° C. to about 8° C., more preferably at about 4° C. In one embodiment, storage occurs for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 48 hours, about 60 hours, about 72 hours, about 84 hours, or about 96 hours. In another embodiment, storage occurs for at least 24 hours, at least 2 days, at least 3 days, or at least 4 days. In a further embodiment, storage occurs at about 4° C. for about 12 hours. In another embodiment, storage occurs at about 4° C. for about 24 hours. In yet another embodiment, storage occurs at about 4° C. for about 48 hours. In still another embodiment, storage occurs at about 4° C. for about 72 hours.

Syringes

In one embodiment of the present invention, the container with zero headspace is a syringe that does not leak aqueous drug product solution when the syringe cap is removed. Syringes are filled at the open end with the needle and cap already attached. The needle is covered with a cap that seals the tip of the needle. In a syringe with a headspace, when the cap is removed the pressure of the headspace can push a drop of the aqueous drug product solution out of the needle. This drop can be up to 50 µL, which may constitute 5% or 10% of the dose intended for the patient in 1.0 mL and 0.5 mL doses, respectively. This may result in a patient not receiving the full dose of the therapeutic agent. To address this, syringes are overfilled with the aqueous drug product solution to account for the waste. Since containers of the present invention do not contain a headspace, aqueous drug product solution is not pushed out when a needle cap is removed. This ensures that patients receive the full intended dose of the aqueous drug product solution without having to incur the cost of overfilling the syringe to account for waste.

In another embodiment of the present invention, an aqueous drug product solution in a syringe with no headspace can be administered to a patient without needing to remove air bubbles from the syringe. In general, air bubbles should not be administered to a patient as part of an aqueous drug product solution dose. Some routes of administration are particularly sensitive to air bubbles. For example, administration of air bubbles during ophthalmic administration can result in blurred vision and possibly endophthalmitis or retinal detachments. The administration instruction for Lucentis, approved for intravitreal injection, require holding an overfilled syringe with the needle pointed up, tapping the syringe to dislodge air bubbles so they rise to the needle, and then expelling drug product to expel air bubbles prior to administration. This requires wasting valuable drug product and may result in inaccurate dosing since the doctor must push the plunger until the stopper is aligned with a mark on the syringe. Since containers of the present invention do not contain a headspace or air bubbles, aqueous drug products can be administered from a container with a pre-set dose without overfilling or pre-administration removal of air bubbles. This ensures that patients receive the full intended dose of the aqueous drug product solution without having to overfill the syringe and waste valuable drug product.

Silicone Oil

In another embodiment of the invention, the portion of the container which a stopper contacts in coated with silicone oil. In a further embodiment of the invention, the entire interior surface of the container is coated with silicone oil. In an embodiment of the invention, the silicone oil is baked on or incubated on the container. In yet another embodiment of the invention, the container is a syringe and the amount of silicone oil is a low, regular, or high amount. A low amount of silicone oil is less than about 0.4 mg per syringe barrel. A regular amount of silicone oil is about 0.4 mg per syringe barrel or about 0.4 to 0.7 mg per syringe barrel. A high amount of silicone oil is about 0.8 mg, about 0.8 mg+/−0.4 mg per barrel, or greater than about 0.7 mg per syringe barrel. In another embodiment of the invention, the amount of silicone oil does not exceed about 2.0, 1.5, 1.2, 1.0, 0.8, 0.6, 0.5, or 0.4 mg per syringe barrel.

Machines for Making Containers with Aqueous Solutions and Zero Headspace

Another embodiment of the present invention is filler-finisher system for preparing a container with an aqueous drug substance solution without a headspace. The system may be single machine, device, or filler-finisher, or may be a collection of machines, devices, or articles of manufacture that prepare a container with an aqueous drug substance solution without a headspace. Herein, the term "filler-finisher" refers such a system, as a single machine and a as collection of machines. The filler-finisher comprises means for performing steps of a method of the present invention. In one embodiment, the filler-finisher comprises the means for filling a container with an aqueous drug substance solution. In another embodiment, the filler-finisher comprises the means for applying a vacuum to a container comprising an aqueous drug substance solution. In another embodiment, the filler-finisher comprises the means for purging the container and the aqueous drug substance solution with a soluble gas. In yet another embodiment of the invention, the filler-finisher comprises the means for closing or stoppering the containers.

In an embodiment of the present invention, the filler-finisher comprises a filling chamber in which containers are filled with an aqueous drug substance solution and a closing or stoppering unit capable of closing filled containers. In an embodiment of the present invention, a vacuum can be applied to the filling chamber. In a further embodiment of the present invention, the filling chamber can be purged with a gas. In a further embodiment of the present invention, the stoppering unit is contained within the filling chamber.

In another embodiment of the present invention, the stoppering unit is contained within a stoppering chamber. In an embodiment of the present invention, a vacuum can be applied to the stoppering chamber. In a further embodiment of the present invention, the stoppering chamber can be purged with a gas.

In one embodiment of the present invention, purging occurs by flooding a sealed chamber in the filler-finisher with a gas. In one embodiment, the gas is supplied by a tank connected to the filler-finisher. In another embodiment, the filler-finisher comprises a valve for regulating the flow of gas into the sealed chamber. In another embodiment, purging occurs in the same chamber that a vacuum can be applied.

In one embodiment of the present invention, the filler-finisher comprises a vacuum pump that degasses a chamber of the filler-finisher. In another embodiment, the degassed chamber can contain containers. In another embodiment of the present invention, the filler-finisher comprises a variable speed vacuum pump. A variable speed vacuum pump can reduce variability in pressure when a specific vacuum pressure is desired. In another embodiment, pressure variability in chambers to which vacuum is about 15 mbar from target pressure, about 5 mbar from target pressure, or about 2 mbar from target pressure. In a further embodiment, vacuum pressure is determined with a ceramic pressure censor. In another embodiment of the present invention, chambers to which vacuum is applied have no or negligible gas leakage. In one embodiment, the vacuum decay is less than 1 mbar/min under 5 mbar. In another embodiment, the decay is less than 0.5 mbar/min under 1 mbar. In a further embodiment, the decay is less than 0.033 mbar/min under 0.11 mbar.

In another embodiment of the present invention, the filler-finisher comprises means for setting and regulating the temperature of a chamber. In another embodiment, the filler-finisher has means for setting and regulating the temperature of a gas used to purge a chamber. In one embodiment, the means for regulating temperature comprises a heating element or comprises a cooling element.

In another embodiment of the present invention, chambers within the filler-finisher are sanitized. In another embodiment, a method of the present invention is performed with the filler-finisher under aseptic conditions. In another embodiment, the particulate count in the chambers meets or exceeds ISO 5 or EU Grade A clean room requirements. In a further embodiment, the filler-finisher comprises a non-viable particle counter. In yet another embodiment, the filler-finisher comprises means for air sampling of viable particles.

In another embodiment of the present invention, the filler-finisher comprises a filling apparatus with a filling needle for filling the containers. In an embodiment of the present invention, the filling apparatus inserts the filling needle into the container near the closed end of the container prior to filling of the container. Once filling begins, the filling needle is removed from the container as filling progresses. In another embodiment, the filling apparatus may remain stationary and the container may be moved to cause the insertion and removal of the filling needle from the container. This process of diving the filling needle into the container reduces splashing, air bubble formation, mixing and other physical stresses on the aqueous drug substance solution during the filling process.

In another embodiment of the present invention, the filler-finisher accurately fills the container with aqueous drug substance solution within about 5% of alert limits and within about 10% of action limits.

In another embodiment of the present invention, a filling bag containing an aqueous drug substance solution is connected to the filler-finisher. In a further embodiment, the filling bag can be directly filled from a drug substance bag. This eliminates the need for a separate formulation or pooling step which add time, cost to the filling process and also imparts additional undesirable stress on the drug substance. In another embodiment, the filling bag is placed as close to the filler-finisher as possible to minimize line loss and agitation of drug product during filling. In yet a further embodiment, the filling bag is attached to the filler-finisher.

In another embodiment of the present invention, the filler-finisher is semi-automated or fully automated to perform a method of the present invention. In another embodiment of the present invention, the filler-finisher is microprocessor controlled. In yet another embodiment of the present invention, the filler-finisher comprises a robotic element to perform a step of a method of the present invention. In yet another embodiment of the present invention, the filler-finisher is a SA25 Aseptic Workcell (Vanrx Pharmasystems, Inc., Burnaby, British Columbia, Canada).

Aqueous Drug Substance Solutions

The zero headspace methods described herein can be used to prepare a stable aqueous drug substance solution in an container with zero headspace. In one embodiment, the stable aqueous drug substance solution comprises a biologic drug substance. In another embodiment, stable aqueous drug substance solution comprises a non-biologic drug substance.

Stable Aqueous Drug Substance Solution

In one embodiment of the invention, the aqueous drug substance solution in a container with a reduced headspace, or zero headspace, is stable at a temperature for a period of time. Conditions under which the aqueous drug substance solution in a container with a reduced or zero headspace is stable include, but is not limited to, are: 40° C. for 6-10 days, at least 5 days, at least 1 week, at least 2 weeks, at least 3 weeks, at least 4 weeks, or at least 1 month; 30° C. for 6-10 days, at least 5 days, at least 1 week, at least 2 weeks, at least 3 weeks, at least 4 weeks, at least 1 month, at least 2 months, at least 9 weeks, at least 3 months, or at least 13 weeks; 25° C. for 6-10 days, at least 5 days, at least 1 week, at least 2 weeks, at least 3 weeks, at least 4 weeks, at least 1 month, at least 2 months, at least 9 weeks, at least 3 months, or at least 13 weeks; 5° C. for at least 1 week, at least 2 weeks, at least 3 weeks, at least 4 weeks, at least 1 month, at least 2 months, at least 9 weeks, at least 3 months, at least 13 weeks, at least 4 months, at least 5 months, at least 6 months, at least 7 months, at least 8 months, at least 9 months, at least 10 months, at least 11 months, or at least 12 months; and −40° C. for at least 1 week, at least 2 weeks, at least 3 weeks, at least 4 weeks, at least 1 month, at least 2 months, at least 9 weeks, at least 3 months, at least 13 weeks, at least 4 months, at least 5 months, at least 6 months, at least 7 months, at least 8 months, at least 9 months, at least 10 months, at least 11 months, at least 12 months, at least 18 months, or at least 24 months. In another embodiment of the invention, the aqueous drug substance solution in a container with a reduced headspace is stable under shear stress, blunt force, agitation, mixing, and conditions.

In another embodiment of the present invention, an aqueous drug substance solution in a container with a reduced headspace, or zero headspace, has stability equal to, or greater than, the stability of the same aqueous drug substance solution in a container with a headspace.

In another embodiment of the present invention, an aqueous drug substance solution in a container with a reduced headspace, or zero headspace, is stable without including known stabilizing excipients. In one embodiment, an aqueous drug substance solution that (i) is free, or substantially free, of buffer, stabilizer, polyol, salt, sugar, surfactant, or combinations thereof; and (ii) is in a container with a reduced headspace, or zero headspace; is stable. In one embodiment, an aqueous drug substance solution that is stable in a container with a reduced, or zero headspace, is free, or substantially free, of buffer. In another embodiment, an aqueous drug substance solution that is stable in a container with a reduced, or zero headspace, is free, or substantially free, of polyol. In yet another embodiment, an aqueous drug substance solution that is stable in a container with a reduced, or zero headspace, is free, or substantially free, of surfactant. In still another embodiment, an aqueous drug substance solution that is stable in a container with a reduced, or zero headspace, is free, or substantially free, of polyol and surfactant. In another embodiment, an aqueous drug substance solution that is stable in a container with a reduced, or zero headspace, is free, or substantially free, of buffer, polyol, and surfactant.

In one embodiment, an aqueous drug substance solution that is stable in a container with a reduced, or zero headspace, comprises amino acid and is free, or substantially free, of buffer, polyol, salt, sugar, surfactant, or combinations thereof. In another embodiment, an aqueous drug substance solution that is stable in a container with a reduced, or zero headspace, comprises salt and is free, or substantially free, of buffer, polyol, stabilizer, sugar, surfactant, or combinations thereof. In yet another embodiment, an aqueous drug substance solution that is stable in a container with a reduced, or zero headspace, comprises amino acid and salt and is free, or substantially free, of buffer, polyol, sugar, surfactant, or combinations thereof. In another embodiment, an aqueous drug substance solution that is stable in a container with a reduced, or zero headspace, comprises amino acid and salt and is free, or substantially free, of buffer. In another embodiment, an aqueous drug substance solution that is stable in a container with a reduced, or zero headspace, comprises amino acid and salt and is free, or substantially free, of polyol. In another embodiment, an aqueous drug substance solution that is stable in a container with a reduced, or zero headspace, comprises amino acid and salt and is free, or substantially free, of surfactant. In another embodiment, an aqueous drug substance solution that is stable in a container with a reduced, or zero headspace, comprises amino acid and salt and is free, or substantially free, of buffer and polyol. In another embodiment, an aqueous drug substance solution that is stable in a container with a reduced, or zero headspace, comprises amino acid and salt and is free, or substantially free, of buffer and surfactant. In another embodiment, an aqueous drug substance solution that is stable in a container with a reduced, or zero headspace, comprises amino acid and salt and is free, or substantially free, of polyol and surfactant. In another embodiment, an aqueous drug substance solution that is stable in a container with a reduced, or zero headspace, comprises amino acid and salt and is free, or substantially free, of buffer, polyol, and surfactant.

In one embodiment, an aqueous drug substance solution that (i) is free, or substantially free, of buffer, stabilizer, polyol, salt, sugar, surfactant, or combinations thereof; and (ii) is in a container with a reduced headspace, or zero headspace; has stability equal to or greater than a second aqueous drug substance solution that (a) comprises the same drug substance and the excipient excluded from the aqueous drug substance solution, and (b) is in a container that contains a headspace.

In one embodiment, an aqueous drug substance solution that (i) is free, or substantially free, of buffer, stabilizer, polyol, salt, sugar, surfactant, or combinations thereof; and (ii) is in a container with a reduced headspace, or zero headspace; has stability equal to or greater than a second aqueous drug substance solution that (a) comprises the same drug substance and the excipient excluded from the aqueous drug substance solution, and (b) is in a container that contains a headspace.

In one embodiment, an aqueous drug substance solution that (i) is free, or substantially free, of surfactant; and (ii) is in a container with a reduced headspace, or zero headspace; has stability equal to or greater than a second aqueous drug substance solution that (a) comprises the same drug substance and surfactant, and (b) is in a container that contains a headspace. In another embodiment, an aqueous drug substance solution that (i) is free, or substantially free, of polyol; and (ii) is in a container with a reduced headspace, or zero headspace; has stability equal to or greater than a second aqueous drug substance solution that (a) comprises the same drug substance and polyol, and (b) is in a container that contains a headspace. In yet another embodiment, an aqueous drug substance solution that (i) is free, or substantially free, of buffer; and (ii) is in a container with a reduced headspace, or zero headspace; has stability equal to or greater than a second aqueous drug substance solution that (a) comprises the same drug substance and buffer, and (b) is in a container that contains a headspace. In one embodiment, an aqueous drug substance solution that (i) is free, or substantially free, of surfactant and polyol; and (ii) is in a container with a reduced headspace, or zero headspace; has stability equal to or greater than a second aqueous drug substance solution that (a) comprises the same drug substance, surfactant and polyol, and (b) is in a container that contains a headspace. In another embodiment, an aqueous drug substance solution that (i) is free, or substantially free, of surfactant and buffer; and (ii) is in a container with a reduced headspace, or zero headspace; has stability equal to or greater than a second aqueous drug substance solution that (a) comprises the same drug substance, surfactant, and buffer, and (b) is in a container that contains a headspace. In still another embodiment, an aqueous drug substance solution that (i) is free, or substantially free, of buffer and polyol; and (ii) is in a container with a reduced headspace, or zero headspace; has stability equal to or greater than a second aqueous drug substance solution that (a) comprises the same drug substance, buffer, and polyol, and (b) is in a container that contains a headspace. In another embodiment, an aqueous drug substance solution that (i) is free, or substantially free, of buffer, surfactant, and polyol; and (ii) is in a container with a reduced headspace, or zero headspace; has stability equal to or greater than a second aqueous drug substance solution that (a) comprises the same drug substance, buffer, surfactant, and polyol, and (b) is in a container that contains a headspace.

In another embodiment of the present invention, an aqueous drug substance solution that is stable in a container with a reduced, or zero headspace, has a conductivity of about 2.5 mS/cm or greater. In another embodiment, the conductivity of the aqueous drug substance solution is from greater than 2.5 mS/cm to about 20 mS/cm. In another embodiment, the conductivity of the aqueous drug substance solution is from about 3 mS/cm to about 10 mS/cm. In another embodiment, the conductivity of the aqueous drug substance solution is about 2.75 mS/cm, about 3 mS/cm, about 4 mS/cm, about 5 mS/cm, about 6 mS/cm, about 7 mS/cm, about 8 mS/cm, about 9 mS/cm, about 10 mS/cm, about 11 mS/cm, about 12 mS/cm, about 13 mS/cm, about 14 mS/cm, about 15 mS/cm, about 16 mS/cm, about 17 mS/cm, about 18 mS/cm, about 19 mS/cm, or about 20 mS/cm.

In another embodiment of the present invention, an aqueous drug substance solution in a container with a reduced headspace, or zero headspace, is stable after being subject to physical stresses including, but not limited to freeze thaw cycles, shipping, and dropping tests.

Various analytical techniques for measuring drug substance stability may be employed. These include, but are not limited to ambient light, differential scanning calorimetry (DSC), dynamic light scattering (DLS), and techniques for measuring the type and degree of particulates that may be present in protein formulations, are available in the art and are reviewed in Peptide and Protein Drug Delivery, 247-301 (Vincent Lee ed., Marcel Dekker, New York, N.Y., 1991) and Jones, 1993 Adv. Drug Delivery Rev. 10: 29-90, for examples. Stability can be measured at a selected temperature for a selected time period.

Shipping Stability

In one embodiment of the present invention, containers with zero headspace that can be exposed to low atmospheric pressure (e.g. air-shipped or stored at high altitude) while maintaining the sterility of the drug product in the container. Containers with drug product prepared by methods of the present invention can air-shipped without risk of contamination to the drug product. Drug product is filled into containers under aseptic and contaminant free conditions. It is important that no contaminants are introduced to the drug product prior to administration to the subject. Some containers have closure devices that can move within the container while maintaining a seal that is intended to keep the drug product sterile. For example, pre-filled syringes are closed with a stopper that is placed inside the body of the syringe. Thus the drug product is kept separated from the environment. However, once the pre-filled syringe is exposed to non-aseptic environments, contaminants may be present on the inside wall of the pre-filled syringe, above the stopper.

If the pre-filled syringe has a headspace under the stopper, then that gas can expand and contract. When a pre-filled syringe is air-shipped, or otherwise subjected to high altitude, the atmospheric pressure outside the syringe drops. In response, the headspace inside the syringe will expand and push the stopper up. Depending on the size of the headspace and the drop in atmospheric pressure, the end of the stopper closest to the drug product may rise more than the height of the stopper. In other words, the stopper may rise above the point where the inner wall of the syringe was exposed to non-aseptic conditions. If this happens, contaminants can be introduced to the drug product which many degrade the drug product or may be harmful to a patient.

The present invention permits containers with drug product to be exposed to reduced atmospheric pressure without risk of contaminating the drug product. A container of the present invention does not contain a headspace. Aqueous solutions compress and expand at much lower rate than gases. Therefore, in the pre-filled syringe example above, if a pre-filled syringe without a headspace is subjected to low atmospheric pressure, the stopper will not rise in the syringe since there is no gas headspace to expand and push the syringe up. Thus, containers prepared by the methods of the present invention can be exposed to low atmospheric pressure (e.g. air-shipped or stored at high altitude) while maintaining the sterility of the drug product in the container.

Formulations for Therapeutic Molecules in Containers with Zero Headspace

An advantage of the present invention is that removing the headspace from a container stabilizes the aqueous solution, including the therapeutic molecule, therein. As a result, therapeutic molecules in containers with zero headspace can be formulated in solutions without excipients traditionally needed to provide stability.

An aqueous drug substance solution in a container with reduced or zero headspace comprises drug substance and aqueous vehicle. In one embodiment, the aqueous vehicle is water. In another embodiment, the water is sterile purified pharmaceutical grade water. In another embodiment, the aqueous drug substance solution in a container with reduced or zero headspace consists essentially of drug substance and aqueous vehicle. In yet another embodiment, the aqueous drug substance solution in a container with reduced or zero headspace consists of drug substance and aqueous vehicle.

In one embodiment of the present invention, an aqueous drug substance solution in a container with reduced or zero headspace comprises adalimumab and water.

In another embodiment of the present invention, the aqueous drug substance solution in a container with reduced or zero headspace comprises drug substance and an excipient. Excipients useful in the aqueous solution comprising a drug substance are known by those of skill in the art.

Buffer Free Formulations

In another embodiment, the aqueous drug substance solution is free of buffer. In another embodiment, an aqueous drug substance solution that is free of buffer in a zero head space container is as stable or more stable than an aqueous drug substance solution with buffer in a container with a headspace.

Surfactant Free Formulations

In another embodiment, the aqueous drug substance solution is free of surfactant. In another embodiment, an aqueous drug substance solution that is free of surfactant in a zero head space container is as stable or more stable than an aqueous drug substance solution with surfactant in a container with a headspace.

Polyol Free Formulations

In another embodiment, the aqueous drug substance solution is free of polyol. In another embodiment, an aqueous drug substance solution that is free of polyol in a zero head space container is as stable or more stable than an aqueous drug substance solution with polyol in a container with a headspace.

Amino Acid Free Formulations

In another embodiment, the aqueous drug substance solution is free of amino acid. In a further embodiment, the solution is free of stabilizing amino acid but contains a buffering amino acid. In another embodiment, an aqueous drug substance solution that is free of amino in a zero head space container is as stable or more stable than an aqueous drug substance solution with amino acid in a container with a headspace.

Stabilizer Free Formulations

In another embodiment, the aqueous drug substance solution is free of stabilizer. In another embodiment, an aqueous drug substance solution that is free of stabilizer in a zero head space container is as stable or more stable than an aqueous drug substance solution with stabilizer in a container with a headspace.

Salt Free Formulations

In another embodiment, the aqueous drug substance solution is free of salt. In another embodiment, an aqueous drug substance solution that is free of salt in a zero head space container is as stable or more stable than an aqueous drug substance solution with salt in a container with a headspace.

Osmolality

In one embodiment, the osmolality of the provided formulations is from about 180 to about 500 mOsM, more preferably between 250 and 350 mOsM. However, it is to be understood that the osmolality can be either higher or lower as specific conditions require.

pH Ranges for Formulations in Containers with Zero Headspace

Based on the results observed in the Examples below, it is now expected that the zero headspace methods herein can be used with solutions having a wide range of pH values, including acidic pH values. The solution will remain pH stable despite dissolved $CO_2$ creating carbonic acid in aqueous solutions which has the potential to alter the pH.

Thus result is unexpected because the zero headspace method was expected to create zero headspace for solutions with a pH of about 5 and above. Without being bound to a particular theory, when $CO_2$ contacts water it reacts with it to form carbonic acid. Carbonic acid is a very weak acid, having pK1=6.38. If the pH of the solution is raised, especially above pH 6, the carbonic acid begins to deprotonate to bicarbonate anion, with a charge of −1. This species is effectively trapped in solution because of its charge. It would need to grab back a proton in order to dissociate to $CO_2$ and water again. Therefore it was expected that, for buffer pHs higher than about 6, there would be a huge sink for $CO_2$ and the zero headspace method should have a high probability of working well. At a mildly acidic pH of ~5, there would still be ~10% of all the $CO_2$ that would be deprotonated, so there ought to be a decent chance that the zero headspace method would work. However, at highly acidic pHs, like 4, it was expected that this sink would essentially be absent, so that the overall solubility of $CO_2$ would be so limited that the zero headspace method might not be effective enough to create a strong enough vacuum to pull the stopper down. Expressed another way, the partial pressure of $CO_2$ at acidic pHs would be relatively high, compared to what it would be at alkaline pH, so a small headspace would remain.

In the zero headspace method, the container with the solution is subjected to a pressure vacuum to remove ambient atmosphere, which also degasses the solution, then purged with $CO_2$, then subjected to vacuum again and stoppered while under vacuum. As a result, the solution is degassed and the $CO_2$ headspace is created at a low pressure (e.g. 40-45 mbar). Thus, the amount of $CO_2$ dissolved into the solution by the method is very low, requiring a small sink for $CO_2$. Therefore, as demonstrated in the examples below, the method can produce containers with zero headspace with acidic solutions.

Adalimumab Formulations in Containers with Zero Headspace

In certain other embodiments the aqueous drug substance solution comprises adalimumab and is free of surfactant.

In certain other embodiments the aqueous drug substance solution comprises adalimumab. Adaliuamb is destabilized by physical stresses and readily forms particles. To address this problem, all FDA approved formulations of adalimumab contain a surfactant (e.g. polysorbate 80) to stabilize adalimumab during fill and finish manufacturing, shipping, and handling. However, surfactants are susceptible to oxidation and hydrolytic reaction, and the impurities and degradation of surfactant can impact product quality. Thus, there is a need for stable adalimumab products that do not contain a surfactant.

In another embodiment of the present invention, adalimumab in an aqueous solution in a container with a reduced headspace, or zero headspace, has stability equal to, or greater than, the stability of a Humira® in a container with a headspace. In yet another embodiment of the present invention, adalimumab in an aqueous solution in a syringe with a zero headspace has stability equal to, or greater than, the stability of a Humira® pre-filled syringe that has a headspace. In a further embodiment, the number of particles in an aqueous adalimumab solution in a container with a reduced headspace, or zero headspace, is equal to or less than the number of particles in Humira in a container with a headspace. In a yet a further embodiment, the aqueous adalimumab solution in a container with a reduced headspace, or zero headspace, does not contain a surfactant. In a yet a further embodiment, the aqueous adalimumab solution in a container with a reduced headspace, or zero headspace, does not contain a polyol. In a yet a further embodiment, the aqueous adalimumab solution in a container with a reduced headspace, or zero headspace, does not contain a sugar. In a yet a further embodiment, the aqueous adalimumab solution in a container with a reduced headspace, or zero headspace, does not contain a buffer.

Adalimumab may be at a concentration from about 20 to about 250 milligrams per milliliter (mg/mL), from about 40 to about 150 mg/mL, from about 30 to about 50 mg/mL, at about 50 mg/mL, at about 100 mg/mL, or at about 150 mg/mL.

In certain other embodiments the aqueous drug substance solution comprises adalimumab and about 0.1%, 0.05%, 0.01% of a surfactant.

In certain embodiments, the aqueous drug substance solution comprising adalimumab further comprises a stabilizer, has a pH of about 5 to about 6, and the adalimumab is present at a concentration from about 50 mg/mL to about 150 mg/mL.

In certain other embodiments the aqueous drug substance solution comprises adalimumab and is free of polyol.

In other embodiments the aqueous drug substance solution comprising adalimumab comprises a buffer, a stabilizer and is free of polyol and surfactant.

In one embodiment of the present invention, an aqueous drug substance solution in a container with reduced or zero headspace comprises adalimumab and buffer. In another embodiment, an aqueous drug substance solution in a container with reduced or zero headspace comprises adalimumab and salt. In yet another embodiment, an aqueous drug substance solution in a container with reduced or zero headspace comprises adalimumab and stabilizer. In a further embodiment, the stabilizer is amino acid. In still a further embodiment, the amino acid is a combination of two or more amino acids. In another embodiment of the present invention, an aqueous drug substance solution in a container with reduced or zero headspace comprises adalimumab and cyclodextrin.

In one embodiment of the present invention, an aqueous drug substance solution in a container with reduced or zero headspace comprises adalimumab, buffer, and stabilizer. In another embodiment of the present invention, an aqueous drug substance solution in a container with reduced or zero headspace comprises adalimumab and stabilizer. In another embodiment of the present invention, an aqueous drug substance solution in a container with reduced or zero headspace comprises adalimumab, salt, and stabilizer. In another embodiment of the present invention, an aqueous drug substance solution in a container with reduced or zero headspace comprises adalimumab, buffer, salt, and stabilizer.

In one embodiment of the present invention, an aqueous drug substance solution in a container with reduced or zero headspace comprises adalimumab, buffer, and amino acid. In another embodiment of the present invention, an aqueous drug substance solution in a container with reduced or zero headspace comprises adalimumab, amino acid, and cyclodextrin. In another embodiment of the present invention, an aqueous drug substance solution in a container with reduced or zero headspace comprises adalimumab, salt, and amino acid. In another embodiment of the present invention, an aqueous drug substance solution in a container with reduced or zero headspace comprises adalimumab, salt, amino acid, and cyclodextrin. In another embodiment of the present invention, an aqueous drug substance solution in a container with reduced or zero headspace comprises adalimumab, buffer, salt, amino acid, and cyclodextrin.

In one embodiment of the present invention, unless the an aqueous drug substance solution in a container with reduced or zero headspace comprising adalimumab expressly includes buffer, the adalimumab drug substance solution is free, or substantially free, of buffer. In another embodiment of the present invention, unless the an aqueous drug substance solution in a container with reduced or zero headspace comprising adalimumab expressly includes polyol, the adalimumab drug substance solution is free, or substantially free, of polyol. In another embodiment of the present invention, unless the an aqueous drug substance solution in a container with reduced or zero headspace comprising adalimumab expressly includes surfactant, the adalimumab drug substance solution is free, or substantially free, of surfactant. In another embodiment of the present invention, unless the an aqueous drug substance solution in a container with reduced or zero headspace comprising adalimumab expressly includes salt, the adalimumab drug substance solution is free, or substantially free, of salt. In another embodiment of the present invention, unless the an aqueous drug substance solution in a container with reduced or zero headspace comprising adalimumab expressly includes sugar, the adalimumab drug substance solution is free, or substantially free, of sugar. In another embodiment of the present invention, unless the an aqueous drug substance solution in a container with reduced or zero headspace comprising adalimumab expressly includes polyol and surfactant, the adalimumab drug substance solution is free, or substantially free, of polyol and surfactant. In another embodiment of the present invention, unless the an aqueous drug substance solution in a container with reduced or zero headspace comprising adalimumab expressly includes buffer and surfactant, the adalimumab drug substance solution is free, or substantially free, of buffer and surfactant. In another embodiment of the present invention, unless the an aqueous drug substance solution in a container with reduced or zero headspace comprising adalimumab expressly includes polyol and buffer, the adalimumab drug substance solution is free, or substantially free, of polyol and buffer. In another embodiment of the present invention, unless the an aqueous drug substance solution in a container with reduced or zero headspace comprising adalimumab expressly includes buffer, polyol, and surfactant, the adalimumab drug substance solution is free, or substantially free, of buffer, polyol, and surfactant.

In one embodiment of the present invention, an aqueous drug substance solution in a container with reduced or zero headspace comprising adalimumab and buffer is free, or substantially free, of a combination of citrate buffer and phosphate buffer.

In one embodiment of the present invention, an aqueous drug substance solution in a container with reduced or zero headspace comprising adalimumab has a pH of about 4 to about 8. In another embodiment of the present invention, the pH is about 5 to about 7. In yet another embodiment, the pH is about 5 to about 5.5. In still a further embodiment the pH is about 5.1, 5.2, 5.3, 5.4, or 5.5. In another embodiment, the pH is 5.2.

In one embodiment of the present invention, an aqueous drug substance solution in a container with reduced or zero headspace comprises adalimumab, buffer, and amino acid; wherein the buffer comprises phosphate, pyrophosphate, citrate, acetate, glutamate, gluconate, histidine, succinate, adipate, maleate, tartrate, and combinations thereof, but not a combination of phosphate and citrate; and wherein the amino acid comprises alanine, cysteine, glutamate, threonine, lysine, histidine, glycine, methionine, serine, proline, arginine, sarcosine, glycine betaine, and combinations thereof.

In one embodiment of the present invention, an aqueous drug substance solution in a container with reduced or zero headspace comprises adalimumab, salt, amino acid, and cyclodextrin; wherein the salt comprises NaCl, KCl, $Na_2SO_4$, $MgCl_2$, and $CaCl_2$; wherein the amino acid comprises alanine, cysteine, glutamate, threonine, lysine, histidine, glycine, methionine, serine, proline, arginine, sarcosine, glycine betaine, and combinations thereof; and wherein cyclodextrin comprises HPβCD.

In one embodiment of the present invention, an aqueous drug substance solution in a container with reduced or zero headspace comprises adalimumab, amino acid, and salt; wherein the salt comprises NaCl, KCl, $Na_2SO_4$, $MgCl_2$, and $CaCl_2$; and wherein the amino acid comprises alanine, cysteine, glutamate, threonine, lysine, histidine, glycine, methionine, serine, proline, arginine, sarcosine, glycine betaine, and combinations thereof.

In one embodiment of the present invention, an aqueous drug substance solution in a container with reduced or zero headspace comprises adalimumab, buffer, salt, amino acid, and HPβCD; wherein the buffer comprises phosphate, pyrophosphate, citrate, acetate, glutamate, gluconate, histidine, succinate, adipate, maleate, tartrate, and combinations thereof, but not a combination of phosphate and citrate; wherein the salt comprises NaCl, KCl, $Na_2SO_4$, $MgCl_2$, and $CaCl_2$; and wherein the amino acid comprises alanine, cysteine, glutamate, threonine, lysine, histidine, glycine, methionine, serine, proline, arginine, sarcosine, glycine betaine, and combinations thereof.

In one embodiment of the present invention, an aqueous drug substance solution in a container with reduced or zero headspace comprising adalimumab and buffer, the concentration of buffer is from about 1 mM to about 100 mM. In another embodiment, the concentration of buffer is from about 5 mM to about 50 mM. In another embodiment, concentration of buffer is about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM.

In one embodiment of the present invention, an aqueous drug substance solution in a container with reduced or zero headspace comprising adalimumab and amino acid, the concentration of amino acid is from about 1 mM to about 500 mM. In another embodiment, the concentration of amino acid is from about 10 mM to about 300 mM. In another embodiment, the concentration of amino acid is about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 205 mM, about 210 mM, about 215 mM, about 220 mM, about 225 mM, about 230 mM, about 235 mM, about 240 mM, about 245 mM, about 250 mM, about 255 mM, about 260 mM, about 265 mM, about 270 mM, about 275 mM, about 280 mM, about 285 mM, about 290 mM, about 295 mM, about 300 mM, about 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, or about 400 mM.

In one embodiment of the present invention, an aqueous drug substance solution in a container with reduced or zero headspace comprising adalimumab and salt, the concentration of salt is from about 1 mM to about 250 mM. In another embodiment, the concentration of salt is from about 5 mM to about 100 mM. In another embodiment, the concentration of salt is from about 10 mM to about 50 mM. In another embodiment, the concentration of salt is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM.

In one embodiment of the present invention, an aqueous drug substance solution in a container with reduced or zero headspace comprising adalimumab and cyclodextrin, the concentration of cyclodextrin is from about 1 mM to about 100 mM. In another embodiment, the concentration of cylclodextrin is from about 20 mM to about 80 mM. in yet another embodiment, the concentration of cylclodextrin is from about 40 mM to about 70 mM. In still another embodiment, the concentration of cylclodextrin is about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, or about 75 mM.

In one embodiment of the present invention, an aqueous drug substance solution in a container with reduced or zero headspace comprises about 50 mg/mL to about 150 mg/mL adalimumab and about 10 mM to about 40 mM buffer. In a further embodiment, the pH of the aqueous drug substance solution is about 5.2. In yet a further embodiment, the aqueous drug substance solution is free, or substantially free, of salt, amino acid, polyol, sugar, surfactant, or combinations thereof.

In one embodiment of the present invention, an aqueous drug substance solution in a container with reduced or zero headspace comprises about 50 mg/mL to about 150 mg/mL adalimumab and about 15 mM to about 100 mM salt. In a further embodiment, the pH of the aqueous drug substance solution is about 5.2. In yet a further embodiment, the aqueous drug substance solution is free, or substantially free, of buffer, amino acid, polyol, sugar, surfactant, or combinations thereof.

In one embodiment of the present invention, an aqueous drug substance solution in a container with reduced or zero headspace comprises about 50 mg/mL to about 150 mg/mL adalimumab and about 50 mM to about 400 mM total amino acid. In a further embodiment, the amino acid is selected from the group consisting of arginine, glycine, threonine, and combinations thereof. In a further embodiment, the pH of the aqueous drug substance solution is about 5.2. In yet a further embodiment, the aqueous drug substance solution is free, or substantially free, of buffer, salt, polyol, sugar, surfactant, or combinations thereof.

In one embodiment of the present invention, an aqueous drug substance solution in a container with reduced or zero headspace comprises about 50 mg/mL to about 150 mg/mL adalimumab, about 10 mM to about 40 mM buffer, about 15 mM to about 35 mM arginine, and about 200 mM to about 250 mM glycine. In a further embodiment, the pH of the aqueous drug substance solution is about 5.2. In yet a further embodiment, the aqueous drug substance solution is free, or substantially free, of salt, polyol, sugar, surfactant, or combinations thereof.

In one embodiment of the present invention, an aqueous drug substance solution in a container with reduced or zero headspace comprises about 50 mg/mL to about 150 mg/mL adalimumab, about 10 mM to about 50 mM salt, about 100 mM to about 180 mM glycine, and about 40 mM to about 100 mM cyclodextrin. In a further embodiment, the pH of the aqueous drug substance solution is about 5.2. In yet a further embodiment, the aqueous drug substance solution is free, or substantially free, of buffer, polyol, sugar, surfactant, or combinations thereof.

In one embodiment of the present invention, an aqueous drug substance solution in a container with reduced or zero headspace comprises about 50 mg/mL to about 150 mg/mL adalimumab, about 5 mM to about 50 mM salt, and about 50 mM to about 400 mM total amino acid. In a further embodiment, the amino acid is selected from the group consisting of arginine, glycine, threonine, and combinations thereof. In one embodiment the amino acid comprises about 15 mM to about 35 mM arginine and about 100 mM to about 180 mM glycine. In another embodiment, the amino acid comprises about 15 mM to about 35 mM arginine, about 100 mM to about 180 mM glycine, and about 10 mM to about 50 mM threonine. In a further embodiment, the pH of the aqueous drug substance solution is about 5.2. In yet a further embodiment, the aqueous drug substance solution is free, or substantially free, of buffer, polyol, sugar, surfactant, or combinations thereof.

In one embodiment of the present invention, an aqueous drug substance solution in a container with reduced or zero headspace comprises about 50 mg/mL to about 150 mg/mL adalimumab, about 10 mM to about 40 mM buffer, about 10 mM to about 50 mM salt, about 100 mM to about 180 mM glycine, and about 40 mM to about 100 mM cyclodextrin. In a further embodiment, the pH of the aqueous drug substance solution is about 5.2. In yet a further embodiment, the aqueous drug substance solution is free, or substantially free, of polyol, sugar, surfactant, or combinations thereof.

EXEMPLARY EMBODIMENTS

A. A method of preparing a rigid container with reduced headspace comprising:
  a) providing a rigid container with a closed end and an open end;
  b) providing a bulk aqueous drug substance solution;
  c) filling the container via the open end with the bulk aqueous drug substance solution to create a container solution;
  d) purging the container with at least one soluble gas at a time selected from the group consisting of prior to the filling step, during the filling step, after the filling step and a combination thereof;
  e) inserting a stopper into the open end of the container creating a headspace; and
  f) storing the container at a temperature below the temperature of the stoppering step,
  wherein the stopper can move within the container while maintaining an airtight seal; and the storage step reduces the headspace to less than 0.1% of the volume of the container.

B. The method of embodiment A, wherein the container is a syringe and the closed end is closed with a needle.

C. The method of embodiment A, wherein the container is a cartridge.

D. The method of embodiment A, wherein the container is filled with between about 0.1 mL and about 10 L of bulk aqueous drug substance solution.

E. The method of embodiment A, wherein the container solution is degassed after the filling step and the container is purged after degassing.

F. The method of embodiment E, wherein the container solution is degassed under a pressure vacuum of at least about 27.5 inHg.

G. The method of embodiment A, wherein the container solution is degassed for about 0.1 to about 60 minutes.

H. The method of embodiment E, wherein the container is purged until the pressure reaches about ambient pressure.

I. The method of embodiment A, wherein the soluble gas is maintained at a temperature within 10° C. of the ambient temperature.

J. The method of embodiment A, wherein the soluble gas is carbon dioxide.

K. The method of embodiment J, wherein the total purging time with carbon dioxide is ten minutes or less.

L. The method of embodiment E, wherein the degassing and purging steps are repeated prior to stoppering the container.

M. The method of embodiment A, wherein stoppering the container occurs under a pressure vacuum.

N. The method of embodiment M, wherein the pressure vacuum is at least about 27.5 inHg.

O. The method of embodiment A, wherein the stoppering step is conducted at room temperature.

P. The method of embodiment A, wherein the stoppering step is conducted at a temperature between room temperature and below the temperature at which the drug substance denatures or degrades.

Q. The method of embodiment P, wherein the storing step is conducted at a temperature at least about 15° C. below the stoppering step without freezing the container solution.

R. The method of embodiment A, wherein the container is stored at a temperature from about −30° C. to about 15° C. without freezing the container solution.

S. The method of embodiment A, wherein the container is stored for at least 4 hours.

T. The method of embodiment A, wherein the storage step results in no visibly detectable headspace.

U. The method of embodiment T, wherein the storage step results in zero headspace.

V. The method of embodiment A, wherein the bulk aqueous drug substance solution is a bulk aqueous non-biologic molecule solution.

W. The method of embodiment V, wherein the bulk aqueous non-biologic molecule solution is a pharmaceutical composition comprising a small molecule.

X. The method of embodiment A, wherein the bulk aqueous drug substance solution is a bulk aqueous protein solution.

Y. The method of embodiment X, wherein the bulk aqueous protein solution is a pharmaceutical composition comprising an antibody.

Z. The method of embodiment A, wherein the bulk aqueous drug substance solution is free or substantially free of surfactant.

AA. The method of embodiment A, wherein the bulk aqueous drug substance solution is free or substantially free of polyol.

AB. The method of embodiment A, wherein the bulk aqueous drug substance solution is free or substantially free of sugar.

AC. The method of embodiment A, wherein the bulk aqueous drug substance solution is free or substantially free of buffer.

AD. The method of embodiment A, wherein the bulk aqueous drug substance solution is free or substantially free of salt.

AE. The method of embodiment A, wherein the bulk aqueous drug substance solution comprises an amino acid.

AF. The method of embodiment AE, wherein the amino acid is selected from alanine, lysine, threonine, valine, leucine, isoleucine, histidine, glycine, methionine, serine, proline, and arginine and combinations thereof.

AG. The method of embodiment A, wherein the bulk aqueous drug substance solution comprises a salt.

AH. The method of embodiment AG, wherein the salt comprises a sodium cation or calcium cation.

AI. The method of embodiment AG, wherein the salt comprises NaCl, $Na_2SO_4$ or $CaCl_2$.

AJ. The method of embodiment Y, wherein the antibody is adalimumab.

AK. The method of embodiment AJ, wherein the pharmaceutical composition is free or substantially free of surfactant.

AL. The method of embodiment AJ, wherein the pharmaceutical composition is free or substantially free of polyol.

AM. The method of embodiment AJ, wherein the pharmaceutical composition is free or substantially free of sugar.

AN. The method of embodiment AJ, wherein the pharmaceutical composition is free or substantially free of buffer.

AO. The method of embodiment AJ, wherein the pharmaceutical composition is free or substantially free of salt.

AP. The method of embodiment AJ, wherein the pharmaceutical composition is free or substantially free of surfactant, polyol, sugar, buffer or combinations thereof.

AQ. The method of embodiment AJ, wherein the pharmaceutical composition is free or substantially free of surfactant, polyol, sugar, and buffer.

AR. The method of embodiment AJ, wherein the pharmaceutical composition is free or substantially free of surfactant, polyol, sugar, and salt.

AS. The method of embodiment AJ, wherein the pharmaceutical composition comprises an amino acid.

AT. The method of embodiment AS, wherein the amino acid is selected from alanine, lysine, threonine, valine, leucine, isoleucine, histidine, glycine, methionine, serine, proline, and arginine and combinations thereof.

AU. The method of embodiment AS, wherein the amino acid is arginine.

AV. The method of embodiment AS, wherein the amino acid is arginine and glycine.

AW. The method of embodiment AS, wherein the amino acid is serine, lysine, and valine.

AX. The method of embodiment AS, wherein the amino acid is threonine, valine, and leucine.

AY. The method of embodiment AS, wherein the amino acid is lysine, methionine, and proline.

AZ. The method of embodiment AS, wherein the amino acid is serine, lysine, and leucine.

BA. The method of embodiment AS, wherein the amino acid is threonine, leucine, and methionine.

BB. The method of embodiment AJ, wherein the pharmaceutical composition comprises a salt.

BC. The method of embodiment BB, wherein the salt comprises a sodium cation or calcium cation.

BD. The method of embodiment BB, wherein the salt comprises NaCl, $Na_2SO_4$ or $CaCl_2$.

BE. The method of embodiment AJ, wherein the pharmaceutical composition comprises an amino acid and a salt.

BF. The method of embodiment BE, wherein the amino acid is selected from alanine, lysine, threonine, valine, leucine, isoleucine, histidine, glycine, methionine, serine, proline, and arginine and combinations thereof.

BG. The method of embodiment BE, wherein the salt comprises a sodium cation or calcium cation.

BH. The method of embodiment BE, wherein the salt comprises NaCl, $Na_2SO_4$ or $CaCl_2$.

BI. The method of embodiment BE, wherein the amino acid comprises arginine and glycine and the salt comprises a calcium cation.

BJ. The method of embodiment BI, wherein the salt is $CaCl_2$.

BK. The method of embodiment BI, wherein the amino acid is arginine and glycine and the salt is $CaCl_2$.

BL. The method of embodiment BE, wherein the amino acid comprises arginine, glycine and threonine and the salt comprises a calcium cation.

BM. The method of embodiment BL, wherein the salt is $CaCl_2$.

BN. The method of embodiment BL, wherein the amino acid is arginine, glycine and threonine and the salt is $CaCl_2$.

BO. A container prepared by the method of embodiment A or E, comprising a container solution within the container and no visibly detectable headspace.

BP. The container of embodiment BO, wherein the container has zero headspace.

BQ. The container of embodiment BO, wherein the container is a syringe or a cartridge.

BR. The container of embodiment BQ, wherein the syringe comprises a closed end closed with a needle.

BS. The container of embodiment BO, wherein the container solution is an aqueous non-biologic molecule solution.

BT. The container of embodiment BS, wherein the non-biologic molecule solution is a pharmaceutical composition comprising a small molecule.

BU. The container of embodiment BO, wherein the container solution is an aqueous protein solution.

BV. The container of embodiment BU, wherein the protein solution is a pharmaceutical composition comprising an antibody.

BW. The container of embodiment BO, wherein the container solution is free or substantially free of surfactant.

BX. The container of embodiment BO, wherein the container solution is free or substantially free of polyol.

BY. The container of embodiment BO, wherein the container solution is free or substantially free of sugar.

BZ. The container of embodiment BO, wherein the container solution is free or substantially free of buffer.

CA. The container of embodiment BO, wherein the container solution is free or substantially free of salt.

CB. The container of embodiment BO, wherein the container solution comprises an amino acid.

CC. The container of embodiment CB, wherein the amino acid is selected from alanine, lysine, threonine, valine, leucine, isoleucine, histidine, glycine, methionine, serine, proline, and arginine and combinations thereof.

CD. The container of embodiment BO, wherein the container solution comprises a salt.

CE. The container of embodiment CD, wherein the salt comprises a sodium cation or calcium cation.

CF. The container of embodiment CD, wherein the salt comprises NaCl, $Na_2SO_4$ or $CaCl_2$.

CG. The container of embodiment BV, wherein the antibody is adalimumab.

CH. The container of embodiment CG, wherein the pharmaceutical composition is free or substantially free of surfactant.

CI. The container of embodiment CG, wherein the pharmaceutical composition is free or substantially free of polyol.

CJ. The container of embodiment CG, wherein the pharmaceutical composition is free or substantially free of sugar.

CK. The container of embodiment CG, wherein the pharmaceutical composition is free or substantially free of buffer.

CL. The container of embodiment CG, wherein the pharmaceutical composition is free or substantially free of salt.

CM. The container of embodiment CG, wherein the pharmaceutical composition is free or substantially free of surfactant, polyol, sugar, buffer or combinations thereof.

CN. The container of embodiment CG, wherein the pharmaceutical composition is free or substantially free of surfactant, polyol, sugar, and buffer.

CO. The container of embodiment CG, wherein the pharmaceutical composition is free or substantially free of surfactant, polyol, sugar, and salt.

CP. The container of embodiment CG, wherein the pharmaceutical composition comprises an amino acid.

CQ. The container of embodiment CP, wherein the amino acid is selected from alanine, lysine, threonine, valine, leucine, isoleucine, histidine, glycine, methionine, serine, proline, and arginine and combinations thereof.

CR. The container of embodiment CP, wherein the amino acid is arginine.

CS. The container of embodiment CP, wherein the amino acid is arginine and glycine.

CT. The container of embodiment CP, wherein the amino acid is serine, lysine, and valine.

CU. The container of embodiment CP, wherein the amino acid is threonine, valine, and leucine.

CV. The container of embodiment CP, wherein the amino acid is lysine, methionine, and proline.

CW. The container of embodiment CP, wherein the amino acid is serine, lysine, and leucine.

CX. The container of embodiment CP, wherein the amino acid is threonine, leucine, and methionine.

CY. The container of embodiment CG, wherein the pharmaceutical composition comprises a salt.

CZ. The container of embodiment CY, wherein the salt comprises a sodium cation or calcium cation.

DA. The container of embodiment CY, wherein the salt comprises NaCl, $Na_2SO_4$ or $CaCl_2$.

DB. The container of embodiment CG, wherein the pharmaceutical composition comprises an amino acid and a salt.

DC. The container of embodiment DB, wherein the amino acid is selected from alanine, lysine, threonine, valine, leucine, isoleucine, histidine, glycine, methionine, serine, proline, and arginine and combinations thereof.

DD. The container of embodiment DB, wherein the salt comprises a sodium cation or calcium cation.

DE. The container of embodiment DB, wherein the salt comprises NaCl, $Na_2SO_4$ or $CaCl_2$.

DF. The container of embodiment DB, wherein the amino acid comprises arginine and glycine and the salt comprises a calcium cation.

DG. The container of embodiment DF, wherein the salt is $CaCl_2$.

DH. The container of embodiment DF, wherein the amino acid is arginine and glycine and the salt is $CaCl_2$.

DI. The container of embodiment DB, wherein the amino acid comprises arginine, glycine and threonine and the salt comprises a calcium cation.

DJ. The container of embodiment DI, wherein the salt is $CaCl_2$.

DK. The container of embodiment DI, wherein the amino acid is arginine, glycine and threonine and the salt is $CaCl_2$.

DL. The container of embodiment BO, wherein the container solution is stable for at least one week at 40° C. or two weeks at 25° C.

DM. The container of embodiment BO, wherein the container solution is stable (i) for at least three months; (ii) for at least six months; or (iii) for at least one year.

DN. The container of embodiment BO, wherein the container solution is has stability comparable to, or better than, the same container solution in a container with a headspace.

DO. The container of embodiment BO, wherein the container solution is free or substantially free of surfactant; and has stability comparable to, or better than, an aqueous solution of the same drug substance that contains surfactant in a container with a headspace.

DP. The container of embodiment BO, wherein the container solution is free or substantially free of polyol; and has stability comparable to, or better than, an aqueous solution of the same drug substance that contains polyol in a container with a headspace.

DQ. The container of embodiment BO, wherein the container solution is free or substantially free of sugar; and has stability comparable to, or better than, an aqueous solution of the same drug substance that contains sugar in a container with a headspace.

DR. The container of embodiment BO, wherein the container solution is free or substantially free of buffer; and has stability comparable to, or better than, an aqueous solution of the same drug substance that contains buffer in a container with a headspace.

DS. The container of embodiment BO, wherein the container solution is free or substantially free of surfactant, polyol, sugar, buffer or combinations thereof; and has stability comparable to, or better than, an aqueous solution of the same drug substance that contains surfactant, polyol, sugar, buffer or combinations thereof in a container with a headspace.

DT. The container of embodiment BO, wherein the container solution is isotonic.

DU. An machine for performing the method of embodiment A, wherein the machine comprises
  a) means for filling a container with a bulk aqueous drug substance solution;
  b) means for purging the container with a soluble gas; and
  c) means for inserting a stopper into the open end of the container.

DV. the machine of embodiment DU, wherein the purging and stoppering of the container occurs within a sealed chamber.

DW. the machine of embodiment DU, wherein the filling, purging, and stoppering of the container occurs within a sealed chamber.

DX. An machine for performing the method of embodiment E, wherein the machine comprises
  a) means for filling a container with a bulk aqueous drug substance solution;
  b) means for degassing the container solution;
  c) means for purging the container with a soluble gas; and
  d) means for inserting a stopper into the open end of the container.

DY. the machine of embodiment DX, wherein the degassing, purging, and stoppering of the container occurs within a sealed chamber.

DZ. the machine of embodiment DX, wherein the filling, degassing, purging, and stoppering of the container occurs within a sealed chamber.

EA. A container prepared by the machine of any one of embodiments DU to DX, wherein the container comprises a container solution within the container and no visibly detectable headspace.

EB. The container of embodiment EA, wherein the container has zero headspace.

EC. The container of embodiment EA, wherein the container is a syringe or a cartridge.

ED. The container of embodiment EC, wherein the syringe comprises a closed end closed with a needle.

EE. The container of embodiment EA, wherein the container solution is an aqueous non-biologic molecule solution.

EF. The container of embodiment EE, wherein the non-biologic molecule solution is a pharmaceutical composition comprising a small molecule.

EG. The container of embodiment EA, wherein the container solution is a aqueous protein solution.

EH. The container of embodiment EG, wherein the protein solution is a pharmaceutical composition comprising an antibody.

EI. A machine for preparing the container of embodiment BO, wherein the machine comprises
  a) means for filling a container with a bulk aqueous drug substance solution;
  b) means for purging the container with a soluble gas; and
  c) means for inserting a stopper into the open end of the container.

EJ. the machine of embodiment EI, wherein the purging and stoppering of the container occurs within a sealed chamber.

EK. the machine of embodiment EI, wherein the filling, purging, and stoppering of the container occurs within a sealed chamber.

EL. An machine for preparing the container of embodiment BO, wherein the machine comprises
  a) means for filling a container with a bulk aqueous drug substance solution;
  b) means for degassing the container solution;
  c) means for purging the container with a soluble gas; and
  d) means for inserting a stopper into the open end of the container.

EM. the machine of embodiment EL, wherein the degassing, purging, and stoppering of the container occurs within a sealed chamber.

EN. the machine of embodiment EL, wherein the filling, degassing, purging, and stoppering of the container occurs within a sealed chamber.

EQ. A method of preparing a syringe with reduced headspace comprising:
  a) filling a syringe comprising an open end with a bulk aqueous drug substance solution to create a syringe solution;
  b) degassing the syringe under a pressure vacuum of at least about 27.5 inHg;
  c) purging the syringe with carbon dioxide;
  d) degassing the syringe under a pressure vacuum of at least about 27.5 inHg;
  e) inserting a stopper into the open end of the syringe creating a headspace; and
  f) storing the syringe at a temperature below the temperature of the stoppering step,
  wherein the stopper can move within the syringe while maintaining an airtight seal; and the storage step results in the syringe having no visibly detectable headspace.

EP. A syringe prepared by the method of embodiment EO, comprising a syringe solution within the syringe and no visibly detectable headspace.

EQ. The syringe of embodiment EP, wherein the container has zero headspace.

ER. The syringe of embodiment EP, wherein the syringe comprises a closed end closed with a needle.

ES. The syringe of embodiment EP, wherein the syringe solution is an aqueous non-biologic molecule solution.

ET. The syringe of embodiment ES, wherein the non-biologic molecule solution is a pharmaceutical composition comprising a small molecule.

EU. The syringe of embodiment EP, wherein the syringe solution is a aqueous protein solution.

EV. The syringe of embodiment EU, wherein the protein solution is a pharmaceutical composition comprising an antibody.

EW. The syringe of embodiment EP, wherein the syringe solution is free or substantially free of surfactant.

EX. The syringe of embodiment EP, wherein the syringe solution is free or substantially free of polyol.

EY. The syringe of embodiment EP, wherein the syringe solution is free or substantially free of sugar.

EZ. The syringe of embodiment EP, wherein the syringe solution is free or substantially free of buffer.

FA. The syringe of embodiment EP, wherein the syringe solution is free or substantially free of salt.

FB. The syringe of embodiment EP, wherein the syringe solution comprises an amino acid.

FC. The syringe of embodiment FB, wherein the amino acid is selected from alanine, lysine, threonine, valine, leucine, isoleucine, histidine, glycine, methionine, serine, proline, and arginine and combinations thereof.

FD. The syringe of embodiment EP, wherein the syringe solution comprises a salt.

FE. The syringe of embodiment FD, wherein the salt comprises a sodium cation or calcium cation.

FF. The syringe of embodiment FD, wherein the salt comprises NaCl, $Na_2SO_4$ or $CaCl_2$.

FG. The syringe of embodiment EV, wherein the antibody is adalimumab.

FH. The syringe of embodiment FG, wherein the pharmaceutical composition is free or substantially free of surfactant.

FI. The syringe of embodiment FG, wherein the pharmaceutical composition is free or substantially free of polyol.

FJ. The syringe of embodiment FG, wherein the pharmaceutical composition is free or substantially free of sugar.

FK. The syringe of embodiment FG, wherein the pharmaceutical composition is free or substantially free of buffer.

FL. The syringe of embodiment FG, wherein the pharmaceutical composition is free or substantially free of salt.

FM. The syringe of embodiment FG, wherein the pharmaceutical composition is free or substantially free of surfactant, polyol, sugar, buffer or combinations thereof.

FN. The syringe of embodiment FG, wherein the pharmaceutical composition is free or substantially free of surfactant, polyol, sugar, and buffer.

FO. The syringe of embodiment FG, wherein the pharmaceutical composition is free or substantially free of surfactant, polyol, sugar, and salt.

FP. The syringe of embodiment FG, wherein the pharmaceutical composition comprises an amino acid.

FQ. The syringe of embodiment FP, wherein the amino acid is selected from alanine, lysine, threonine, valine, leucine, isoleucine, histidine, glycine, methionine, serine, proline, and arginine and combinations thereof.

FR. The syringe of embodiment FP, wherein the amino acid is arginine.

FS. The syringe of embodiment FP, wherein the amino acid is arginine and glycine.

FT. The syringe of embodiment FP, wherein the amino acid is serine, lysine, and valine.

FU. The syringe of embodiment FP, wherein the amino acid is threonine, valine, and leucine.

FV. The syringe of embodiment FP, wherein the amino acid is lysine, methionine, and proline.

FW. The syringe of embodiment FP, wherein the amino acid is serine, lysine, and leucine.

FX. The syringe of embodiment FP, wherein the amino acid is threonine, leucine, and methionine.

FY. The syringe of embodiment FG, wherein the pharmaceutical composition comprises a salt.

FZ. The syringe of embodiment FY, wherein the salt comprises a sodium cation or calcium cation.

GA. The syringe of embodiment FY, wherein the salt comprises NaCl, $Na_2SO_4$ or $CaCl_2$.

GB. The syringe of embodiment FG, wherein the pharmaceutical composition comprises an amino acid and a salt.

GC. The syringe of embodiment GB, wherein the amino acid is selected from alanine, lysine, threonine, valine, leucine, isoleucine, histidine, glycine, methionine, serine, proline, and arginine and combinations thereof.

GD. The syringe of embodiment GB, wherein the salt comprises a sodium cation or calcium cation.

GE. The syringe of embodiment GB, wherein the salt comprises NaCl, $Na_2SO_4$ or $CaCl_2$.

GF. The syringe of embodiment GB, wherein the amino acid comprises arginine and glycine and the salt comprises a calcium cation.

GG. The syringe of embodiment GF, wherein the salt is $CaCl_2$.

GH. The syringe of embodiment GF, wherein the amino acid is arginine and glycine and the salt is $CaCl_2$.

GI. The syringe of embodiment GB, wherein the amino acid comprises arginine, glycine and threonine and the salt comprises a calcium cation.

GJ. The syringe of embodiment GI, wherein the salt is $CaCl_2$.

GK. The syringe of embodiment GI, wherein the amino acid is arginine, glycine and threonine and the salt is $CaCl_2$.

GL. The syringe of embodiment EP, wherein the syringe solution is stable for at least one week at 40° C. or two weeks at 25° C.

GM. The syringe of embodiment EP, wherein the syringe solution is stable (i) for at least three months; (ii) for at least six months; or (iii) for at least one year.

GN. The syringe of embodiment EP, wherein the syringe solution has stability comparable to, or better than, the same syringe solution in a syringe with a headspace.

GO. The syringe of embodiment EP, wherein the syringe solution is free or substantially free of surfactant; and has stability comparable to, or better than, an aqueous solution of the same drug substance that contains surfactant in a syringe with a headspace.

GP. The syringe of embodiment EP, wherein the syringe solution is free or substantially free of polyol; and has stability comparable to, or better than, an aqueous solution of the same drug substance that contains polyol in a syringe with a headspace.

GQ. The syringe of embodiment EP, wherein the syringe solution is free or substantially free of sugar; and has stability comparable to, or better than, an aqueous solution of the same drug substance that contains sugar in a syringe with a headspace.

GR. The syringe of embodiment EP, wherein the syringe solution is free or substantially free of buffer; and has stability comparable to, or better than, an aqueous solution of the same drug substance that contains buffer in a syringe with a headspace.

GS. The syringe of embodiment EP, wherein the syringe solution is free or substantially free of surfactant, polyol, sugar, buffer or combinations thereof; and has stability comparable to, or better than, an aqueous solution of the same drug substance that contains surfactant, polyol, sugar, buffer or combinations thereof in a syringe with a headspace.

GT. The syringe of embodiment EP, wherein the syringe solution is isotonic.

GU. A method of preparing a pliable container with reduced headspace comprising:
    a) providing a pliable container with a closed end and an open end;
    b) providing a bulk aqueous drug substance solution;
    c) filling the container via the open end with the bulk aqueous drug substance solution to create a container solution;
    d) purging the container with at least one soluble gas at a time selected from the group consisting of prior to the filling step, during the filling step, after the filling step and a combination thereof;
    e) closing the open end of the container creating a headspace; and
    f) storing the container at a temperature below the temperature of the stoppering step,
    wherein the closed container maintains an airtight seal; and the storage step reduces the headspace to less than 0.1% of the volume of the container.

GV. The method of embodiment GU, wherein the container solution is degassed after the filling step and the container is purged after degassing.

GW. The method of embodiment GV, wherein the container solution is degassed under a pressure vacuum of at least about 27.5 inHg.

GX. The method of embodiment GU, wherein the container solution is degassed for about 0.1 to about 60 minutes.

GY. The method of embodiment GV, wherein the container is purged until the pressure reaches about ambient pressure.

GZ. The method of embodiment GU, wherein the soluble gas is maintained at a temperature within 10° C. of the ambient temperature.

HA. The method of embodiment GU, wherein the soluble gas is carbon dioxide.

HB. The method of embodiment HA, wherein the total purging time with carbon dioxide is ten minutes or less.

HC. The method of embodiment GV, wherein the degassing and purging steps are repeated prior to stoppering the container.

HD. The method of embodiment GU, wherein closing the container occurs under a pressure vacuum.

HE. The method of embodiment HD, wherein the pressure vacuum is at least about 27.5 inHg.

HF. The method of embodiment GU, wherein the closing step is conducted at room temperature.

HG. The method of embodiment GU, wherein the closing step is conducted at a temperature between room temperature and below the temperature at which the drug substance denatures or degrades.

HH. The method of embodiment HG, wherein the storing step is conducted at a temperature at least about 15° C. below the closing step without freezing the container solution.

HI. The method of embodiment GU, wherein the container is stored at a temperature from about −30° C. to about 15° C. without freezing the container solution.

HJ. The method of embodiment GU, wherein the container is stored for at least 4 hours.

HK. The method of embodiment GU, wherein the storage step results in no visibly detectable headspace.

HL. The method of embodiment HK, wherein the storage step results in zero headspace.

HM. The method of embodiment GU, wherein the bulk aqueous drug substance solution is a bulk aqueous non-biologic molecule solution.

HN. The method of embodiment HM, wherein the bulk aqueous non-biologic molecule solution is a pharmaceutical composition comprising a small molecule.

HO. The method of embodiment GU, wherein the bulk aqueous drug substance solution is a bulk aqueous protein solution.

HP. The method of embodiment HO, wherein the bulk aqueous protein solution is a pharmaceutical composition comprising an antibody.

HQ. The method of embodiment GU, wherein the bulk aqueous drug substance solution is free or substantially free of surfactant.

HR. The method of embodiment GU, wherein the bulk aqueous drug substance solution is free or substantially free of polyol.

HS. The method of embodiment GU, wherein the bulk aqueous drug substance solution is free or substantially free of sugar.

HT. The method of embodiment GU, wherein the bulk aqueous drug substance solution is free or substantially free of buffer.

HU. The method of embodiment GU, wherein the bulk aqueous drug substance solution is free or substantially free of salt.

HV. The method of embodiment GU, wherein the bulk aqueous drug substance solution comprises an amino acid.

HW. The method of embodiment HV, wherein the amino acid is selected from alanine, lysine, threonine, valine, leucine, isoleucine, histidine, glycine, methionine, serine, proline, and arginine and combinations thereof.

HX. The method of embodiment GU, wherein the bulk aqueous drug substance solution comprises a salt.

HY. The method of embodiment HX, wherein the salt comprises a sodium cation or calcium cation.

HZ. The method of embodiment HX, wherein the salt comprises NaCl, $Na_2SO_4$ or $CaCl_2$.

IA. The method of embodiment HP, wherein the antibody is adalimumab.

IB. The method of embodiment IA, wherein the pharmaceutical composition is free or substantially free of surfactant.

IC. The method of embodiment IA, wherein the pharmaceutical composition is free or substantially free of polyol.

ID. The method of embodiment IA, wherein the pharmaceutical composition is free or substantially free of sugar.

IE. The method of embodiment IA, wherein the pharmaceutical composition is free or substantially free of buffer.

IF. The method of embodiment IA, wherein the pharmaceutical composition is free or substantially free of salt.

IG. The method of embodiment IA, wherein the pharmaceutical composition is free or substantially free of surfactant, polyol, sugar, buffer or combinations thereof.

IH. The method of embodiment IA, wherein the pharmaceutical composition is free or substantially free of surfactant, polyol, sugar, and buffer.

II. The method of embodiment IA, wherein the pharmaceutical composition is free or substantially free of surfactant, polyol, sugar, and salt.

IJ. The method of embodiment IA, wherein the pharmaceutical composition comprises an amino acid.

IK. The method of embodiment IJ, wherein the amino acid is selected from alanine, lysine, threonine, valine, leucine, isoleucine, histidine, glycine, methionine, serine, proline, and arginine and combinations thereof.

IL. The method of embodiment IJ, wherein the amino acid is arginine.

IM. The method of embodiment IJ, wherein the amino acid is arginine and glycine.

IN. The method of embodiment IJ, wherein the amino acid is serine, lysine, and valine.

IO. The method of embodiment IJ, wherein the amino acid is threonine, valine, and leucine.

IP. The method of embodiment IJ, wherein the amino acid is lysine, methionine, and proline.

IQ. The method of embodiment IJ, wherein the amino acid is serine, lysine, and leucine.

IR. The method of embodiment IJ, wherein the amino acid is threonine, leucine, and methionine.

IS. The method of embodiment IA, wherein the pharmaceutical composition comprises a salt.

IT. The method of embodiment IS, wherein the salt comprises a sodium cation or calcium cation.

IU. The method of embodiment IS, wherein the salt comprises NaCl, $Na_2SO_4$ or $CaCl_2$.

IV. The method of embodiment IA, wherein the pharmaceutical composition comprises an amino acid and a salt.

IW. The method of embodiment IV, wherein the amino acid is selected from alanine, lysine, threonine, valine, leucine, isoleucine, histidine, glycine, methionine, serine, proline, and arginine and combinations thereof.

IX. The method of embodiment IV, wherein the salt comprises a sodium cation or calcium cation.

IY. The method of embodiment IV, wherein the salt comprises NaCl, $Na_2SO_4$ or $CaCl_2$.

IZ. The method of embodiment IV, wherein the amino acid comprises arginine and glycine and the salt comprises a calcium cation.

JA. The method of embodiment IZ, wherein the salt is $CaCl_2$.

JB. The method of embodiment IZ, wherein the amino acid is arginine and glycine and the salt is $CaCl_2$.

JC. The method of embodiment IV, wherein the amino acid comprises arginine, glycine and threonine and the salt comprises a calcium cation.

JD. The method of embodiment JC, wherein the salt is $CaCl_2$.

JE. The method of embodiment JC, wherein the amino acid is arginine, glycine and threonine and the salt is $CaCl_2$.

JF. A container prepared by the method of embodiment GU or GV, comprising a container solution within the container and no visibly detectable headspace.

JG. The container of embodiment JF, wherein the container has zero headspace.

JH. The container of embodiment JF, wherein the container is a syringe or a cartridge.

JI. The container of embodiment JH, wherein the syringe comprises a closed end closed with a needle.

JJ. The container of embodiment JF, wherein the container solution is an aqueous non-biologic molecule solution.

JK. The container of embodiment JJ, wherein the non-biologic molecule solution is a pharmaceutical composition comprising a small molecule.

JL. The container of embodiment JF, wherein the container solution is a aqueous protein solution.

JM. The container of embodiment JL, wherein the protein solution is a pharmaceutical composition comprising an antibody.

JN. The container of embodiment JF, wherein the container solution is free or substantially free of surfactant.

JO. The container of embodiment JF, wherein the container solution is free or substantially free of polyol.

JP. The container of embodiment JF, wherein the container solution is free or substantially free of sugar.

JQ. The container of embodiment JF, wherein the container solution is free or substantially free of buffer.

JR. The container of embodiment JF, wherein the container solution is free or substantially free of salt.

JS. The container of embodiment JF, wherein the container solution comprises an amino acid.

JT. The container of embodiment JS, wherein the amino acid is selected from alanine, lysine, threonine, valine, leucine, isoleucine, histidine, glycine, methionine, serine, proline, and arginine and combinations thereof.

JU. The container of embodiment JF, wherein the container solution comprises a salt.

JV. The container of embodiment JU, wherein the salt comprises a sodium cation or calcium cation.

JW. The container of embodiment JU, wherein the salt comprises NaCl, $Na_2SO_4$ or $CaCl_2$.

JX. The container of embodiment JM, wherein the antibody is adalimumab.

JY. The container of embodiment JX, wherein the pharmaceutical composition is free or substantially free of surfactant.

JZ. The container of embodiment JX, wherein the pharmaceutical composition is free or substantially free of polyol.

KA. The container of embodiment JX, wherein the pharmaceutical composition is free or substantially free of sugar.

KB. The container of embodiment JX, wherein the pharmaceutical composition is free or substantially free of buffer.

KC. The container of embodiment JX, wherein the pharmaceutical composition is free or substantially free of salt.

KD. The container of embodiment JX, wherein the pharmaceutical composition is free or substantially free of surfactant, polyol, sugar, buffer or combinations thereof.

KE. The container of embodiment JX, wherein the pharmaceutical composition is free or substantially free of surfactant, polyol, sugar, and buffer.

KF. The container of embodiment JX, wherein the pharmaceutical composition is free or substantially free of surfactant, polyol, sugar, and salt.

KG. The container of embodiment JX, wherein the pharmaceutical composition comprises an amino acid.

KH. The container of embodiment KG, wherein the amino acid is selected from alanine, lysine, threonine, valine, leucine, isoleucine, histidine, glycine, methionine, serine, proline, and arginine and combinations thereof.

KI. The container of embodiment KG, wherein the amino acid is arginine.

KJ. The container of embodiment KG, wherein the amino acid is arginine and glycine.

KK. The container of embodiment KG, wherein the amino acid is serine, lysine, and valine.

KL. The container of embodiment KG, wherein the amino acid is threonine, valine, and leucine.

KM. The container of embodiment KG, wherein the amino acid is lysine, methionine, and proline.

KN. The container of embodiment KG, wherein the amino acid is serine, lysine, and leucine.

KO. The container of embodiment KG, wherein the amino acid is threonine, leucine, and methionine.

KP. The container of embodiment JX, wherein the pharmaceutical composition comprises a salt.

KQ. The container of embodiment KP, wherein the salt comprises a sodium cation or calcium cation.

KR. The container of embodiment KP, wherein the salt comprises NaCl, $Na_2SO_4$ or $CaCl_2$.

KS. The container of embodiment JX, wherein the pharmaceutical composition comprises an amino acid and a salt.

KT. The container of embodiment KS, wherein the amino acid is selected from alanine, lysine, threonine, valine, leucine, isoleucine, histidine, glycine, methionine, serine, proline, and arginine and combinations thereof.

KU. The container of embodiment KS, wherein the salt comprises a sodium cation or calcium cation.

KV. The container of embodiment KS, wherein the salt comprises NaCl, $Na_2SO_4$ or $CaCl_2$.

KW. The container of embodiment KS, wherein the amino acid comprises arginine and glycine and the salt comprises a calcium cation.

KX. The container of embodiment KW, wherein the salt is $CaCl_2$.

KY. The container of embodiment KW, wherein the amino acid is arginine and glycine and the salt is $CaCl_2$.

KZ. The container of embodiment KS, wherein the amino acid comprises arginine, glycine and threonine and the salt comprises a calcium cation.

LA. The container of embodiment KZ, wherein the salt is $CaCl_2$.

LB. The container of embodiment KZ, wherein the amino acid is arginine, glycine and threonine and the salt is $CaCl_2$.

LC. The container of embodiment JF, wherein the container solution is stable for at least one week at 40° C. or two weeks at 25° C.

LD. The container of embodiment JF, wherein the container solution is stable (i) for at least three months; (ii) for at least six months; or (iii) for at least one year.

LE. The container of embodiment JF, wherein the container solution has stability comparable to, or better than, the same container solution in a container with a headspace.

LF. The container of embodiment JF, wherein the container solution is free or substantially free of surfactant; and has stability comparable to, or better than, an aqueous solution of the same drug substance that contains surfactant in a container with a headspace.

LG. The container of embodiment JF, wherein the container solution is free or substantially free of polyol; and has stability comparable to, or better than, an aqueous solution of the same drug substance that contains polyol in a container with a headspace.

LH. The container of embodiment JF, wherein the container solution is free or substantially free of sugar; and has stability comparable to, or better than, an aqueous solution of the same drug substance that contains sugar in a container with a headspace.

LI. The container of embodiment JF, wherein the container solution is free or substantially free of buffer; and has stability comparable to, or better than, an aqueous solution of the same drug substance that contains buffer in a container with a headspace.

LJ. The container of embodiment JF, wherein the container solution is free or substantially free of surfactant, polyol, sugar, buffer or combinations thereof; and has stability comparable to, or better than, an aqueous solution of the same drug substance that contains surfactant, polyol, sugar, buffer or combinations thereof in a container with a headspace.

LK. The container of embodiment JF, wherein the container solution is isotonic.

LL. A machine for performing the method of embodiment GU, wherein the machine comprises a) means for filling a container with a bulk aqueous drug substance solution;

b) means for purging the container with a soluble gas; and c) means for closing the open end of the container.

LM. The machine of embodiment LL, wherein the purging and stoppering of the container occurs within a sealed chamber.

LN. The machine of embodiment LL, wherein the filling, purging, and closing of the container occurs within a sealed chamber.

LO. A machine for performing the method of embodiment GX, wherein the machine comprises
   a) means for filling a container with a bulk aqueous drug substance solution;
   b) means for degassing the container solution;
   c) means for purging the container with a soluble gas; and
   d) means for closing the open end of the container.

LP. The machine of embodiment LO, wherein the degassing, purging, and closing of the container occurs within a sealed chamber.

LQ. The machine of embodiment LO, wherein the filling, degassing, purging, and closing of the container occurs within a sealed chamber.

LR. A container prepared by the machine of any one of embodiments LL to LO, wherein the container comprises a container solution within the container and no visibly detectable headspace.

LS. The container of embodiment LR, wherein the container has zero headspace.

LT. The container of embodiment LR, wherein the container solution is an aqueous non-biologic molecule solution.

LU. The container of embodiment LT, wherein the non-biologic molecule solution is a pharmaceutical composition comprising a small molecule.

LV. The container of embodiment LR, wherein the container solution is a aqueous protein solution.

LW. The container of embodiment LV, wherein the protein solution is a pharmaceutical composition comprising an antibody.

LX. A machine for preparing the container of embodiment JF, wherein the machine comprises
   a) means for filling a container with a bulk aqueous drug substance solution;
   b) means for purging the container with a soluble gas; and
   c) means for closing the open end of the container.

LY. The machine of embodiment LX, wherein the purging and closing of the container occurs within a sealed chamber.

LZ. The machine of embodiment LX, wherein the filling, purging, and closing of the container occurs within a sealed chamber.

MA. A machine for preparing the container of embodiment JF, wherein the machine comprises
   a) means for filling a container with a bulk aqueous drug substance solution;
   b) means for degassing the container solution;
   c) means for purging the container with a soluble gas; and
   d) means for closing the open end of the container.

MB. The machine of embodiment MA, wherein the degassing, purging, and closing of the container occurs within a sealed chamber.

MC. The machine of embodiment MA, wherein the filling, degassing, purging, and closing of the container occurs within a sealed chamber.

MD. A machine for preparing a container that contains an aqueous drug substance solution with no headspace comprising,
   a) an apparatus for filling the container with the aqueous drug substance solution,
   b) a sealable chamber which can be subjected to a vacuum and which can be purged with a soluble gas, and
   c) a apparatus for closing the container;
   wherein the machine is configured or programmed to fill the container with a defined amount of the aqueous drug substance solution, subject the aqueous drug substance solution to a vacuum in the sealed chamber, purge the aqueous drug substance solution with a soluble gas in the sealed chamber, and then close the container.

ME. The machine of embodiment MD, wherein the apparatus for filling the container is an apparatus for filling syringes.

MF. The machine of embodiment ME, wherein the apparatus for filling syringes comprises a filling needle.

MG. The machine of embodiment MF, wherein the apparatus is configured or programmed to insert the filling needle into the syringe, begin filling the container with the aqueous drug substance solution and withdraw the filling needle as the syringe is filled.

MH. The machine of embodiment MD, comprising a variable speed vacuum pump to create a vacuum in the sealable chamber.

MI. The machine of embodiment MD, comprising a pressure sensor for detecting pressure in the sealable chamber.

MJ. The machine of embodiment MD, wherein the sealable container has a vacuum decay of less than 1 mbar/min when under 5 mbar of pressure.

MK. The machine of embodiment MD, comprising an apparatus for purging the sealable container with a soluble gas.

ML. The machine of embodiment MK, wherein the apparatus purges the sealable chamber with a soluble gas supplied by a source connected to the machine.

MM. The machine of embodiment ML, wherein the soluble gas is $CO_2$.

MN. The machine of embodiment MM, wherein the $CO_2$ is supplied as a gas and not liquefied $CO_2$.

MO. The machine of embodiment MD, wherein the chambers in which container filling, vacuum, purging, and container closing occur are sanitized.

MP. The machine of embodiment MD, wherein the chambers in which container filling, vacuum, purging, and container closing occur meet or exceed ISO 5 or EU Grade A clean room requirements.

MQ. The machine of embodiment MD, comprising a non-viable particle counter.

MR. The machine of embodiment MD, comprising means for air sampling of viable particles.

MS. The machine of embodiment MD, comprising means for controlling the temperature within a chamber of the machine.

MT. The machine of embodiment MD, comprising an apparatus for supplying aqueous drug substance solution to the filling apparatus.

MU. The machine of embodiment MT, wherein the supply apparatus supplies the filling apparatus with an aqueous drug substance solution supplied by a source connected to the machine.

MV. The machine of embodiment MU, wherein the aqueous drug substance solution is an antibody solution.

MW. The machine of embodiment MV, wherein the antibody solution is an adalimumab solution.

MX. The machine of embodiment MW, wherein the adalimumab solution does not contain a surfactant.

MY. The machine of embodiment MW, wherein the adalimumab solution does not contain a polyol.

MZ. The machine of embodiment MW, wherein the adalimumab solution does not contain a sugar.

NA. The machine of embodiment MW, wherein the adalimumab solution does not contain a buffer.

NB. The machine of embodiment MD, wherein an apparatus is a robotic apparatus.

NC. The machine of embodiment MD, wherein the filling, vacuum, purging, and closing steps are automated.

ND. A stable pharmaceutical composition comprising:
a) adalimumab,
b) stabilizer comprising an amino acid, and
c) salt;
wherein the composition is free of buffer, polyol, surfactant, or combinations thereof; has a pH of about 5 to about 6; and has a conductivity of greater than 3.0 mS/cm.

NE. The pharmaceutical composition of embodiment ND, wherein the stabilizer comprises two or more amino acids.

NF. The pharmaceutical composition of embodiment NE, wherein the stabilizer comprises glycine and arginine.

NG. The pharmaceutical composition of embodiment NE, wherein the stabilizer comprises glycine, arginine, and threonine.

NH. The pharmaceutical composition of embodiment ND, wherein the salt comprises a divalent cation.

NI. The pharmaceutical composition of embodiment NH, wherein the divalent cation is selected from the group consisting of Ca2+, and Mg2+.

NJ. The pharmaceutical composition of embodiment NH, wherein the salt comprises $MgCl_2$ or $CaCl_2$.

NK. The pharmaceutical composition of embodiment ND, wherein the salt is selected from NaCl, KCl, $Na_2SO_4$, $MgCl_2$, $CaCl_2$, and adipate.

NL. The pharmaceutical composition of embodiment ND, wherein the stabilizer comprises glycine and arginine, and the salt comprises $CaCl_2$.

NM. The pharmaceutical composition of embodiment ND, wherein the stabilizer comprises glycine, arginine, and threonine, and the salt comprises $CaCl_2$.

NN. The pharmaceutical composition of embodiment ND, wherein the pH is about 5.2.

NO. The pharmaceutical composition of embodiment ND, wherein the composition has osmolality of about 180 to 420 mOsM; the composition is suitable for administration to a subject as a single dosage; the composition has a concentration of adalimumab in the range of 30 to about 50 mg/ml; and the dosage contains about 10 to 80 mg of adalimumab.

NP. The pharmaceutical composition of embodiment ND, wherein the concentration of adalimumab is about 50 mg/ml and the dosage is about 40 mg.

NQ. The pharmaceutical composition of embodiment ND, wherein the dosage is about 40 mg and results in less pain upon administration to a subject in comparison to an adalimumab composition having a buffer comprising citrate.

NR. The pharmaceutical composition of embodiment ND, wherein the composition is stable for:
a) 7 days at −40° C.,
b) 14 days at −40° C.,
c) 30 days at −40° C.,
d) 7 days at 5° C.,
e) 14 days at 5° C.,
f) 30 days at 5° C.,
g) 7 days at 25° C.,
h) 14 days at 25° C.,
i) 30 days at 25° C.,
j) 7 days at 40° C.,
k) 14 days at 40° C., or
l) 30 days at 40° C.

NS. The pharmaceutical composition of embodiment ND, wherein the composition is stable (i) for at least three months; (ii) for at least six months; or (iii) for at least one year.

NT. The pharmaceutical composition of embodiment ND, wherein the composition is contained in a container comprising no headspace.

NU. The pharmaceutical composition of embodiment NT, wherein the composition is free of surfactant; and has stability comparable to, or better than, an adalimumab composition that contains surfactant in a container with a headspace.

NV. The pharmaceutical composition of embodiment NT, wherein the composition is free of polyol; and has stability comparable to, or better than, an adalimumab composition that contains polyol in a container with a headspace.

NW. The pharmaceutical composition of embodiment NT, wherein the composition is free of buffer; and has stability comparable to, or better than, an adalimumab composition that contains buffer in a container with a headspace.

NX. The pharmaceutical composition of embodiment NT, wherein the composition is free of surfactant and polyol; and has stability comparable to, or better than, an adalimumab composition that contains surfactant and polyol in a container with a headspace.

NY. The pharmaceutical composition of embodiment NT, wherein the composition is free of surfactant and buffer; and has stability comparable to, or better than, an adalimumab composition that contains surfactant and buffer in a container with a headspace.

NZ. The pharmaceutical composition of embodiment NT, wherein the composition is free of polyol and buffer; and has stability comparable to, or better than, an adalimumab composition that contains polyol and buffer in a container with a headspace.

OA. The pharmaceutical composition of embodiment NT, wherein the composition is free of surfactant, polyol, and buffer; and has stability comparable to, or better than, an adalimumab composition that contains surfactant, polyol, and buffer in a container with a headspace.

OB. A stable pharmaceutical composition in a container with zero headspace, the composition comprising:
a) adalimumab,
b) stabilizer comprising an amino acid, and
c) salt;
wherein the composition is free of buffer, polyol, surfactant, or combinations thereof; has a pH of about 5 to about 6; and has a conductivity of greater than 3.0 mS/cm.

OC. The pharmaceutical composition of embodiment OB, wherein the stabilizer comprises two or more amino acids.

OD. The pharmaceutical composition of embodiment OC, wherein the stabilizer comprises glycine and arginine.

OE. The pharmaceutical composition of embodiment OC, wherein the stabilizer comprises glycine, arginine, and threonine.

OF. The pharmaceutical composition of embodiment OB, wherein the salt comprises a divalent cation.

OG. The pharmaceutical composition of embodiment OF, wherein the divalent cation is selected from the group consisting of Ca2+, and Mg2+.

OH. The pharmaceutical composition of embodiment OF, wherein the salt comprises $MgCl_2$ or $CaCl_2$.

OI. The pharmaceutical composition of embodiment OB, wherein the salt is selected from NaCl, KCl, $Na_2SO_4$, $MgCl_2$, $CaCl_2$, and adipate.

OJ. The pharmaceutical composition of embodiment OB, wherein the stabilizer comprises glycine and arginine, and the salt comprises $CaCl_2$.

OK. The pharmaceutical composition of embodiment OB, wherein the stabilizer comprises glycine, arginine, and threonine, and the salt comprises $CaCl_2$.

OL. The pharmaceutical composition of embodiment OB, wherein the pH is about 5.2.

OM. The pharmaceutical composition of embodiment OB, wherein the composition has osmolality of about 180 to 420 mOsM; the composition is suitable for administration to a subject as a single dosage; the composition has a concentration of adalimumab in the range of 30 to about 50 mg/ml; and the dosage contains about 10 to 80 mg of adalimumab.

ON. The pharmaceutical composition of embodiment OB, wherein the concentration of adalimumab is about 50 mg/ml and the dosage is about 40 mg.

OO. The pharmaceutical composition of embodiment OB, wherein the dosage is about 40 mg and results in less pain upon administration to a subject in comparison to an adalimumab composition having a buffer comprising citrate.

OP. The pharmaceutical composition of embodiment OB, wherein the composition is stable for:
a) 7 days at −40° C.,
b) 14 days at −40° C.,
c) 30 days at −40° C.,
d) 7 days at 5° C.,
e) 14 days at 5° C.,
f) 30 days at 5° C.,
g) 7 days at 25° C.,
h) 14 days at 25° C.,
i) 30 days at 25° C.,
j) 7 days at 40° C.,
k) 14 days at 40° C., or
l) 30 days at 40° C.

OQ. The pharmaceutical composition of embodiment OB, wherein the composition is stable (i) for at least three months; (ii) for at least six months; or (iii) for at least one year.

OR. The pharmaceutical composition of embodiment OB, wherein the composition is free of surfactant; and has stability comparable to, or better than, an adalimumab composition that contains surfactant in a container with a headspace.

OS. The pharmaceutical composition of embodiment OB, wherein the composition is free of polyol; and has stability comparable to, or better than, an adalimumab composition that contains polyol in a container with a headspace.

OT. The pharmaceutical composition of embodiment OB, wherein the composition is free of buffer; and has stability comparable to, or better than, an adalimumab composition that contains buffer in a container with a headspace.

OU. The pharmaceutical composition of embodiment OB, wherein the composition is free of surfactant and polyol; and has stability comparable to, or better than, an adalimumab composition that contains surfactant and polyol in a container with a headspace.

OV. The pharmaceutical composition of embodiment OB, wherein the composition is free of surfactant and buffer; and has stability comparable to, or better than, an adalimumab composition that contains surfactant and buffer in a container with a headspace.

OW. The pharmaceutical composition of embodiment OB, wherein the composition is free of polyol and buffer; and has stability comparable to, or better than, an adalimumab composition that contains polyol and buffer in a container with a headspace.

OX. The pharmaceutical composition of embodiment OB, wherein the composition is free of surfactant, polyol, and buffer; and has stability comparable to, or better than, an adalimumab composition that contains surfactant, polyol, and buffer in a container with a headspace.

OY. An article of manufacture comprising a stoppered syringe containing a stable aqueous pharmaceutical formulation; wherein there is no detectable headspace in the syringe; and wherein the stable aqueous pharmaceutical formulation comprises adalimumab and an ionic excipient, and is free or substantially free of buffer.

OZ. The article of manufacture of claim OY, wherein the pharmaceutical formulation is at least as stable as an adalimumab formulation comprising a buffer in a syringe with a detectable gas headspace.

PA. The article of manufacture of claim OY, wherein the pharmaceutical formulation is stable for one week at 40° C. or two weeks at 25° C.

PB. The article of manufacture of claim OY, wherein the pharmaceutical formulation is free or substantially free of surfactant.

PC. The article of manufacture of claim OY, wherein the pharmaceutical formulation is free or substantially free of polyol.

PD. The article of manufacture of claim OY, wherein the pharmaceutical formulation is free or substantially free of surfactant and polyol.

PE. The article of manufacture of claim OY, wherein the stoppered syringe has zero headspace.

PF. The article of manufacture of claim OY, wherein the ionic excipient comprises a stabilizer.

PG. The article of manufacture of claim OY, wherein the ionic excipient comprises a tonicity agent.

PH. The article of manufacture of claim OY, wherein the ionic excipient comprises a salt.

PI. The article of manufacture of claim OY, wherein the pharmaceutical composition comprises an amino acid.

PJ. The article of manufacture of claim PI, wherein the amino acid is selected from histidine, glycine, methionine, serine, proline, arginine, and combinations thereof.

PK. The article of manufacture of claim OY, wherein the pharmaceutical formulation is isotonic.

PL. The article of manufacture of claim OY, wherein the pharmaceutical formulation has stability comparable to, or better than, the same pharmaceutical formulation in a syringe with a headspace.

PM. The article of manufacture of claim OY, wherein the pharmaceutical formulation has stability comparable to, or better than, an aqueous adalimumab formulation that contains buffer in a syringe with a headspace.

PN. The article of manufacture of claim OY, wherein the pharmaceutical formulation, upon administration to a subject, results in a degree of pain or discomfort no worse than, or better than, that of an AbbVie-supplied Humira® composition, having a concentration of adalimumab equal to about 50 mg/mL.

EXAMPLES

Not to be held to a particular theory, the purging of the headspace with carbon dioxide or any other readily dissolvable gas (e.g. gaseous water, gaseous ethanol, carbon monoxide, gaseous formic acid) creates a vacuum once the temperature is lowered from room temperature to a range of 1 to 10° C. For example, in a stoppered syringe, the stopper moves to reduce the headspace to zero due to the fact carbon dioxide more readily dissolves in the aqueous drug substance solution at the lower temperature creating a vacuum in the headspace which was once occupied by the gaseous carbon dioxide and additionally increasing the volume of the solution. Alternatively, if a container is prepared with a low pressure headspace of a readily dissolvable gas, the low pressure gas will dissolve into the aqueous drug substance solution. Thus, in a syringe for example, the stopper moves to reduce the headspace to zero as the gas dissolved into the solution.

Additionally, if the bulk aqueous drug substance solution is degassed prior to filling the container, or while in the container, but prior to closure, the effect is greater because there is no gas in the solution which can escape into the headspace in place of the dissolved carbon dioxide. Inserting the stopper into the syringe under vacuum allows for closer placement of the stopper to the surface of the solution due to less atmospheric pressure pushing back against the stopper. However, because there is less carbon dioxide in the headspace when the stopper is inserted under vacuum the force generated by the dissolving of the carbon dioxide into the solution at low temperatures is also reduced such that the headspace is not completely removed.

The following Examples are provided solely for illustrative purposes and are not meant to limit the invention in any way.

Example 1. Filling a Syringe with an Aqueous Buffer Solution 1 mL syringes were filled at room temperature with 0.5 mL of a room temperature, non-degassed, aqueous buffer solution using a pipette to deliver the solution into the open end of the syringe. Next, the headspace in the syringe was purged with carbon dioxide at a flow rate of 10 milliliters/minute for 0.5 minutes using a glass pipette connected to a carbon dioxide cylinder via plastic tubing. A stopper was mechanically inserted into the open end of the syringe until the headspace was from 4 to 6 millimeters. The syringes were then stored at 4° C. at atmospheric pressure for four days. Surprisingly, following storage at 4° C. for four days the headspace in the syringes was reduced up to 80%. See FIG. 1 showing the resulting headspace in syringes with an initial headspace of 4 millimeters (see, FIG. 1C), 5 millimeters (see, FIG. 1B) and 6 millimeters (see, FIG. 1A.)

Example 2. Filling a Syringe with a Degassed Aqueous Buffer Solution

Figure 2:
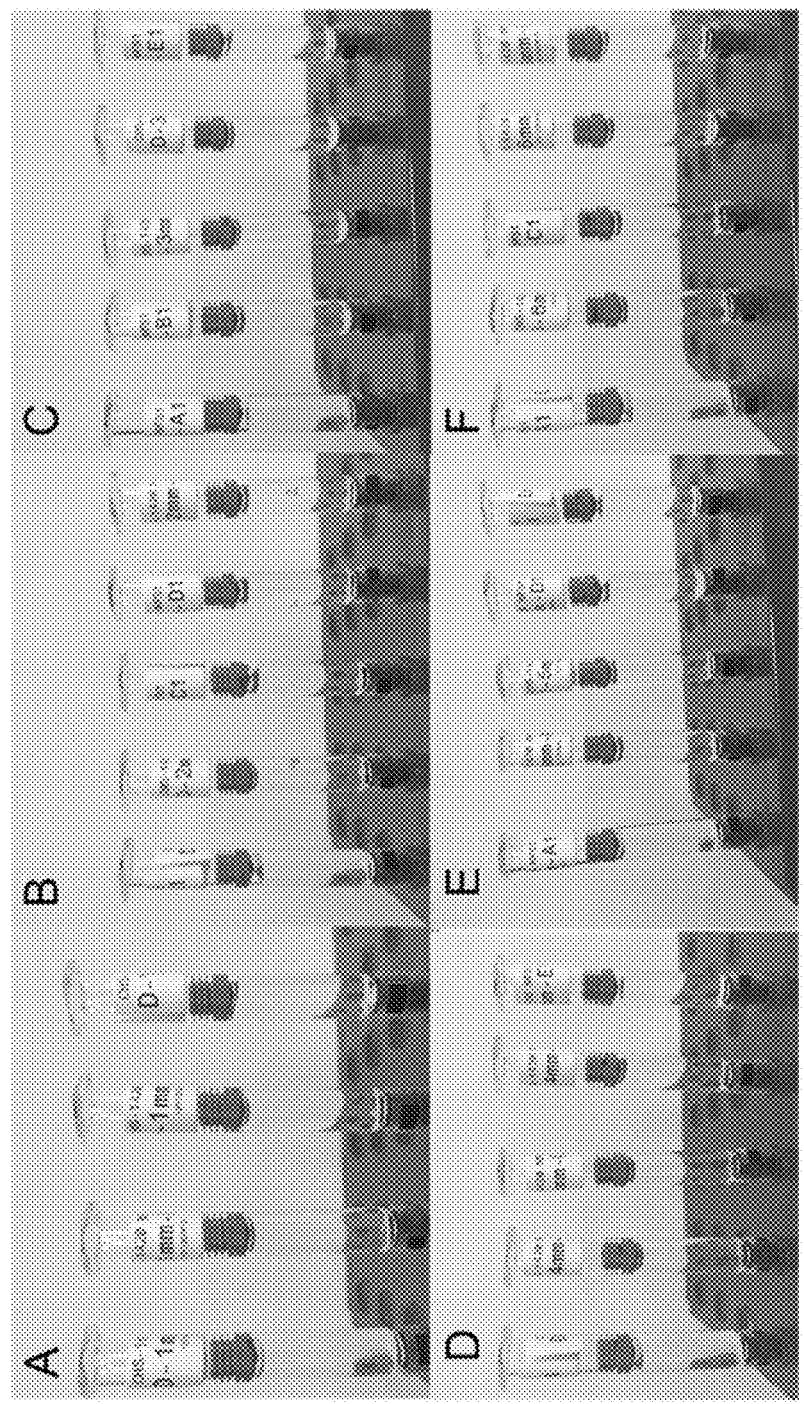
FIG. 2. Reduced headspace in syringes filled with degassed bulk aqueous protein solution following the process in Example 2. Resulting headspaces are shown in panels A, B, C, D, and E for syringes that had an initial headspace of 1 millimeters, 2 millimeters, 3 millimeters, 4 millimeters, 5 millimeters, and 6 millimeters, respectively.
Figure 3:
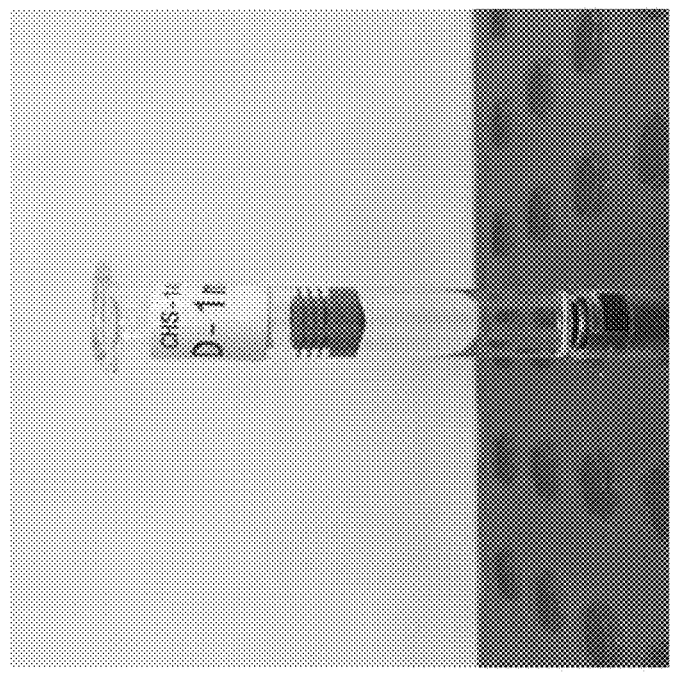
FIG. 3. Syringe filled with degassed bulk aqueous protein solution with no detectable headspace.

1 L of an aqueous buffer solution was degassed under 75 Torr of pressure at room temperature. 1 mL syringes were then filled at room temperature with 0.5 mL of room temperature degassed aqueous protein solution using a pipette to deliver the solution into the open end of the syringe. Next, the headspace in the syringe was purged with carbon dioxide at a flow rate of 10 milliliters/minute for 0.5 minutes using a glass pipette connected to a carbon dioxide cylinder via plastic tubing. A stopper was mechanically inserted into the open end of the syringe until the headspace was from 4 to 6 millimeters. The syringes were then stored at 4° C. at atmospheric pressure for four days. Surprisingly, following storage at 4° C. for four days the headspace in the syringes was reduced up to 100%. See FIG. 2 showing the resulting headspace in syringes with an initial headspace of 1 millimeter (FIG. 2A), 2 millimeters (FIG. 2B), 3 millimeters (FIG. 2C), 4 millimeters (FIG. 2D), 5 millimeters (FIG. 2E) and 6 millimeters (FIG. 2F.) See also FIG. 3 showing the resulting headspace in an additional syringe with an initial headspace of 1 millimeter. As demonstrated in FIG. 2, degassing the bulk aqueous protein solution results in an overall greater reduction in headspace. Further, degassing the bulk aqueous protein solution results in a final headspace that is independent of the initial headspace. Finally, as demonstrated in FIG. 3, degassing of the bulk aqueous solution is sufficient to achieve zero headspace.

Figure 4:
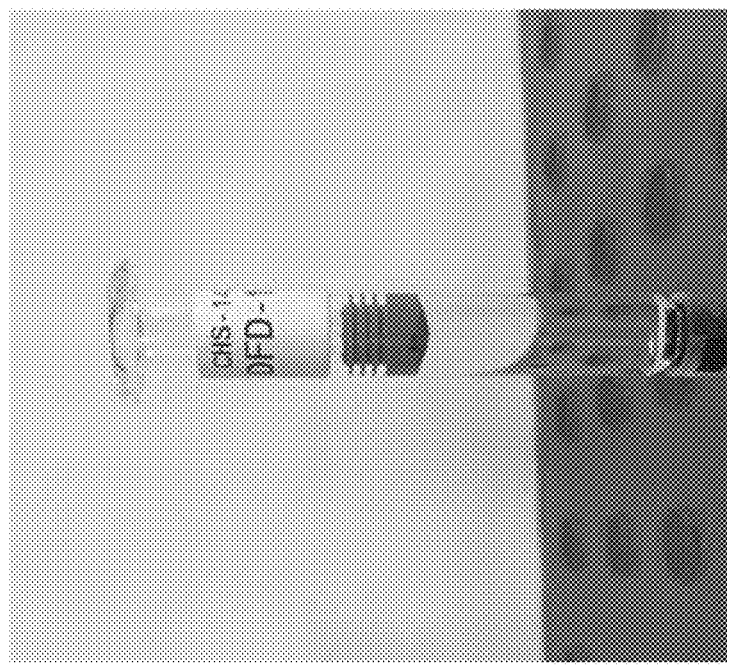
FIG. 4. Syringe filled with degassed bulk aqueous protein solution, that was further degassed after the syringe was filled, with no detectable headspace.

Example 3. Degassing a Syringe Filled with Degassed Aqueous Protein Solution 1 L of an aqueous protein solution was degassed under 75 Torr of pressure at room temperature. A 1 mL syringe was then filled at room temperature with 0.5 mL of room temperature degassed aqueous protein solution using a pipette to deliver the solution into the open end of the syringe. The syringe was then degassed under 75 Torr of pressure. Next, the headspace in the syringe was purged with carbon dioxide at a flow rate of 10 milliliters/minute for 0.5 minutes using a glass pipette connected to a carbon dioxide cylinder via plastic tubing. A stopper was mechanically inserted into the open end of the syringe until the headspace was about 1 millimeter. The syringe was then stored at 4° C. at atmospheric pressure for four days. Surprisingly, following storage at 4° C. for four days the headspace in the syringe was reduced 100%. See FIG. 4 showing the absence of headspace in a syringe with an initial headspace of 1 millimeter. Optionally, prior to stoppering the syringe, the degassing and purging steps are repeated.

Example 4. Filling a Syringe with an Aqueous Buffer Solution and Degassing 1 mL syringes were filled at room temperature with 0.5 mL of a room temperature, non-degassed, aqueous buffer solution using a pipette to deliver the solution into the open end of the syringe. The syringe was then degassed under 75 Torr of pressure. Next, the headspace in the syringe was purged with carbon dioxide at a flow rate of 10 milliliters/minute for 0.5 minutes using a glass pipette connected to a carbon dioxide cylinder via plastic tubing. A stopper was mechanically inserted into the open end of the syringe until the headspace was about 1 millimeter. The syringe was then stored at 4° C. at atmospheric pressure for four days. Surprisingly, following storage at 4° C. for four days the headspace in the syringe was reduced 100%. Optionally, prior to stoppering the syringe, the degassing and purging steps are repeated.

1 mL syringes were filled at room temperature, under normal atmosphere, with 0.5 mL of a room temperature, non-degassed, aqueous buffer solution. The syringes were placed in a vacuum chamber and the solution in the syringes was then degassed under 75 Torr of pressure for 30 minutes. The environment surrounding the syringes was then purged with carbon dioxide at ambient pressure by flooding the vacuum chamber with carbon dioxide. The syringes and the solution were again degassed under 75 Torr of pressure for 30 minutes. Next, the environment surrounding the syringes was then purged with carbon dioxide at ambient pressure by flooding the vacuum chamber with carbon dioxide. While in a carbon dioxide environment at ambient pressure, a stopper was mechanically inserted into the open end of the syringe until a headspace was formed. The syringes were then stored at 2-8° C. at atmospheric pressure.

Figure 5:
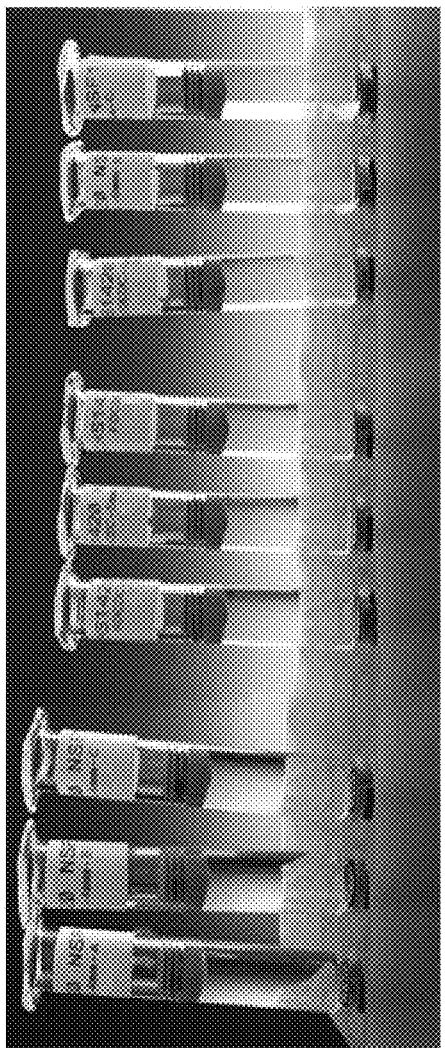
FIG. 5. Panels A and B are syringes filled with aqueous protein solution, which were degassed after the syringes were filled, with no detectable headspace.
Figure 5:
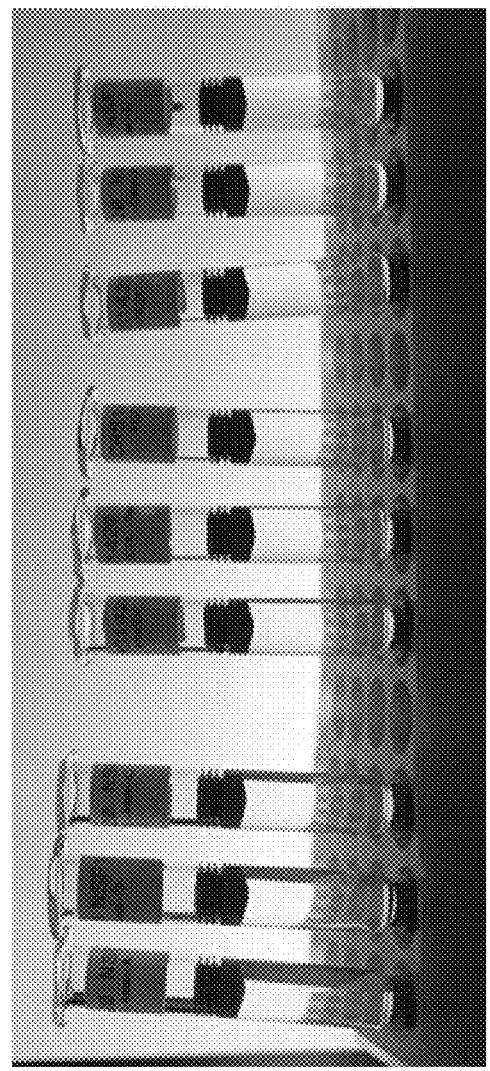

Twelve syringes were tested following the process in the preceding paragraph. Three syringes were filled with a surfactant free buffered solution and stoppered with a 4 mm headspace. Three syringes were filled with a surfactant free buffered solution and stoppered with a 5 mm headspace. Three syringes were filled with aqueous protein solutions containing surfactants and stoppered with a 5 mm headspace. Three syringes were filled with a surfactant free buffer solution and stoppered with a 6 mm headspace. Surprisingly, following storage at 4° C. for three days, none of the twelve syringes had a visibly detectable headspace. See FIG. 5, panels A and B.

All twelve syringes with no detectable headspace were then subjected to the headspace detection procedure discussed in the example below. No headspace was formed in any of the twelve syringes, confirming that the syringes have zero headspace.

Example 5. Detecting Headspace

The following process is used to determine if containers with no visible headspace have no headspace. First, containers are brought to ambient room temperature. Next, containers are subjected to a pressure vacuum. A suitable pressure vacuum is 75 Torr of pressure. While under the pressure vacuum, containers may be evaluated for the presence of a visibly detectable headspace. Containers are then returned to atmospheric pressure and evaluated for the presence of a visibly detectable headspace. The presence of a visibly detectable headspace in the container while under vacuum or after return to atmospheric pressure demonstrates the presence of a headspace (that was otherwise not detectable). Containers with an invisible headspace can be visualized by placing the container under a pressure vacuum. Further, for those containers with no headspace a reduction in atmospheric pressure as low as 75 Torr does not result in creation of a headspace.

Two syringes were subject to different filling procedures and evaluated by the headspace detection method described above. The first syringe (E1) was filled using the filling procedure of example 3 above and resulted in no visual headspace. The second syringe (A1) was filled using the filling procedure of example 4 above, with the syringe degassing and carbon dioxide purge repeated, and resulted in no visual headspace.

Figure 6:
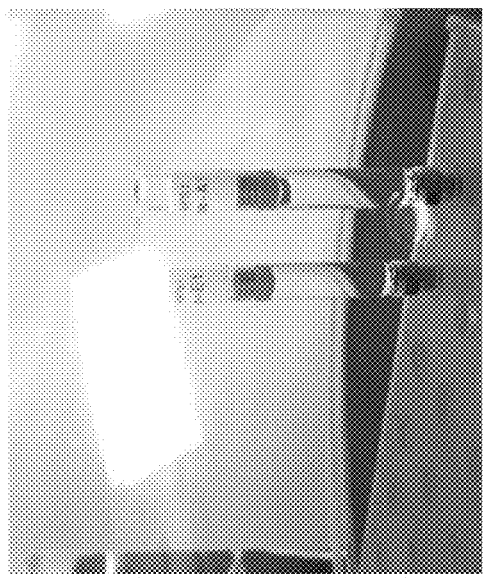
FIG. 6. Headspace in stoppered syringes before (panel A), during (panel B) and after (panel C) being subject to a pressure vacuum; No detectable headspace in stoppered syringes after subsequent cold temperature incubation (panel D).
Figure 6:
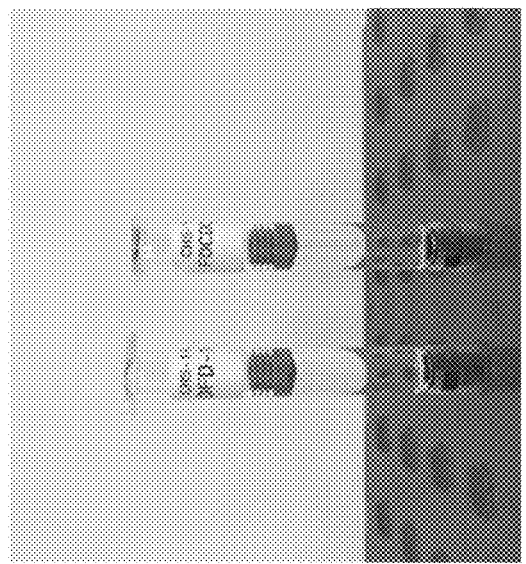
Figure 6:
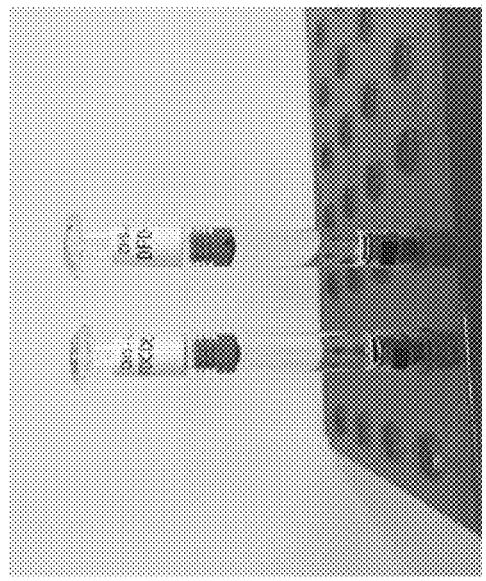
Figure 6:
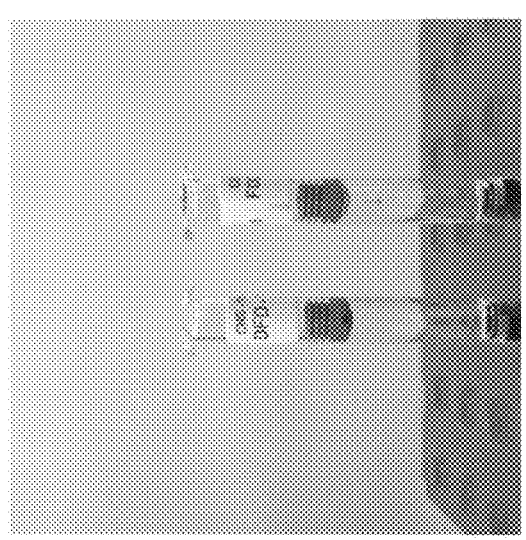

The two syringes were brought to ambient room temperature. No visual headspace was detected. See FIG. 6A (A1 left, E1 right). The two syringes were then subjected to a pressure vacuum of 75 Torr of pressure. While under the pressure vacuum a headspace appeared in the second syringe (A1). See FIG. 6B, right. The two syringes were then returned to atmospheric pressure where the visual headspace remained in the second syringe (A1). See FIG. 6C, right. This result demonstrates that headspace may remain that cannot be detected by the human eye. Syringes with no visibly detectable headspace at atmospheric pressure that do not develop a headspace in atmospheric pressure as low as 75 Torr, have zero headspace.

Following the detection process, both syringes were placed back at a temperature of 4° C. for 6 days. The detection method was then repeated for both syringes. Surprisingly, no headspace was detected in the second syringe (A1) after incubation at 4° C. for 6 additional days. See FIG. 6D, right. Thus, syringes, or containers in general, may be reduced to zero headspace by extending the low temperature incubation or cycling the low temperature incubation.

Example 6. Reduced Headspace Under Various Conditions

Six processes were evaluated for the ability to produce a container with no headspace. Aqueous buffered solutions and aqueous protein solutions were evaluated in syringes. Syringes coated with either a regular level of silicone oil (target about 0.4 mg) or a high amount of silicone oil (target about 0.8 mg) were evaluated. For all conditions, bulk solution was degassed for 1 hour under vacuum prior to filling in syringes. All syringes were filled under ambient pressure and atmosphere and stoppered by vacuum stoppering. Approximately 15 minutes after stoppering, syringes were evaluated for the presence of a headspace. Syringes were then stored at 1-10° C. for 5 days then evaluated for the presence of a headspace. Syringes were subjected to the detection method in Example 5 to confirm lack of a headspace.

Process 1

Place syringes in a vacuum stoppering unit. Pull maximum vacuum to remove air from the stoppering chamber and syringes—hold vacuum for 5 minutes. Bring the pressure in the chamber back to atmospheric pressure by $CO_2$. Pull max vacuum again. Stopper the syringes.

Process 2

Place syringes in a vacuum stoppering unit. Pull maximum vacuum to remove air from the stoppering chamber and syringes—hold vacuum for 15 minutes. Bring the pressure in the chamber back to atmospheric pressure by $CO_2$. Pull max vacuum again. Stopper the syringes.

Process 3

Place syringes in a vacuum stoppering unit. Pull maximum vacuum to remove air from the stoppering chamber and syringes—hold vacuum for 5 minutes. Bring the pressure in the chamber back to atmospheric pressure by $CO_2$. Pull maximum vacuum to remove air from the stoppering chamber and syringes—hold vacuum for 5 minutes. Bring the pressure in the chamber back to atmospheric pressure by $CO_2$. Pull max vacuum again. Stopper the syringes.

Process 4

Place syringes in a vacuum stoppering unit. Pull maximum vacuum to remove air from the stoppering chamber and syringes—hold vacuum for 5 minutes. Bring the pressure in the chamber back to atmospheric pressure by $CO_2$. Pull maximum vacuum to remove air from the stoppering chamber and syringes—hold vacuum for 5 minutes. Bring the pressure in the chamber back to atmospheric pressure by $CO_2$. Stopper the syringes.

Process 5

Place syringes in a vacuum stoppering unit. Pull maximum vacuum to remove air from the stoppering chamber and syringes—hold vacuum for 5 minutes. Bring the pressure in the chamber back to atmospheric pressure by $CO_2$. Pull maximum vacuum to remove air from the stoppering chamber and syringes—hold vacuum for 5 minutes. Bring the pressure in the chamber back to half atmospheric pressure by $CO_2$. Stopper the syringes.

Process 6

Place syringes in a vacuum stoppering unit. Pull maximum vacuum to remove air from the stoppering chamber and syringes. Stopper the syringes.

Results

The tables below list the headspace detected in syringes, filled according to the processes above, at time 0 (T0, 15 minutes after stoppering) and after five days at 1-10° C.

TABLE 6A

| | Process 1 | | | | Process 2 | | | |
| --- | --- | --- | --- | --- | --- | --- | --- | --- |
| | Low Silicone Headspace (mm) | | High Silicone Headspace (mm) | | Low Silicone Headspace (mm) | | High Silicone Headspace (mm) | |
| Syringe | T0 | 5 days | T0 | 5 days | T0 | 5 days | T0 | 5 days |
| 1 | <1 | <1 | <1 | <1 | <1 | <1 | <1 | <1 |
| 2 | <1 | <1 | <1 | <1 | <1 | <1 | <1 | <1 |
| 3 | <1 | <1 | <1 | <1 | <1 | <1 | <1 | <1 |
| 4 | <1 | <1 | <1 | <1 | <1 | <1 | <1 | <1 |
| 5 | <1 | <1 | <1 | <1 | <1 | <1 | <1 | <1 |
| 6 | <1 | <1 | <1 | <1 | <1 | <1 | <1 | <1 |
| 7 | <1 | <1 | <1 | <1 | <1 | <1 | <1 | <1 |
| 8 | <1 | <1 | <1 | <1 | <1 | <1 | <1 | <1 |
| 9 | <1 | <1 | <1 | <1 | <1 | <1 | <1 | <1 |
| 10 | <1 | <1 | <1 | <1 | <1 | <1 | <1 | <1 |
| 11 | <1 | <1 | <1 | <1 | <1 | <1 | <1 | <1 |
| 12 | <1 | <1 | <1 | <1 | <1 | <1 | <1 | <1 |
| 13 | <1 | <1 | <1 | <1 | <1 | <1 | <1 | <1 |
| 14 | <1 | <1 | <1 | <1 | <1 | <1 | <1 | <1 |
| 15 | <1 | <1 | <1 | <1 | <1 | <1 | <1 | <1 |

TABLE 6B

| | Process 3 | | | | Process 4 | | | |
| --- | --- | --- | --- | --- | --- | --- | --- | --- |
| | Low Silicone Headspace (mm) | | High Silicone Headspace (mm) | | Low Silicone Headspace (mm) | | High Silicone Headspace (mm) | |
| Syringe | T0 | 5 days | T0 | 5 days | T0 | 5 days | T0 | 5 days |
| 1 | <1 | <1 | <1 | <1 | 13.0 | 5.0 | 14.5 | 11.0 |
| 2 | <1 | <1 | <1 | <1 | 13.0 | 6.6 | 14.5 | 11.1 |
| 3 | <1 | <1 | <1 | <1 | 13.0 | 7.3 | 15.3 | 12.9 |
| 4 | <1 | <1 | <1 | <1 | 12.7 | 7.2 | 15.3 | 12.7 |
| 5 | <1 | <1 | <1 | <1 | 11.9 | 6.8 | 14.4 | 11.0 |
| 6 | <1 | <1 | <1 | <1 | | 6.8 | | 11.0 |
| 7 | <1 | <1 | <1 | <1 | | 6.7 | | 11.0 |
| 8 | <1 | <1 | <1 | <1 | | 6.7 | | 11.0 |
| 9 | <1 | <1 | <1 | <1 | | 5.4 | | 11.0 |
| 10 | <1 | <1 | <1 | <1 | | 5.3 | | 9.6 |
| 11 | <1 | <1 | <1 | <1 | | 6.5 | | 10.1 |
| 12 | <1 | <1 | <1 | <1 | | 7.9 | | 10.1 |
| 13 | <1 | <1 | <1 | <1 | | 10.0 | | 10.1 |
| 14 | <1 | <1 | <1 | <1 | | 7.5 | | 10.4 |
| 15 | <1 | <1 | <1 | <1 | | 7.7 | | 9.1 |

TABLE 6C

| | Process 5 | | | | Process 6 | | | |
| --- | --- | --- | --- | --- | --- | --- | --- | --- |
| | Low Silicone Headspace (mm) | | High Silicone Headspace (mm) | | Low Silicone Headspace (mm) | | High Silicone Headspace (mm) | |
| Syringe | T0 | 5 days | T0 | 5 days | T0 | 5 days | T0 | 5 days |
| 1 | 12.3 | 7.3 | 13.3 | 9.9 | <1 | <1 | <1 | <1 |
| 2 | 12.3 | 7.6 | 14.1 | 9.9 | <1 | <1 | <1 | <1 |
| 3 | 13.3 | 6.8 | 13.9 | 10.6 | <1 | <1 | <1 | <1 |
| 4 | 13.3 | 6.8 | 13.9 | 10.8 | <1 | <1 | <1 | <1 |
| 5 | 13.3 | 6.8 | 13.9 | 11.0 | <1 | <1 | <1 | <1 |
| 6 | | 5.2 | | 11.0 | <1 | <1 | <1 | <1 |
| 7 | | 5.6 | | 9.9 | <1 | <1 | <1 | <1 |
| 8 | | 5.6 | | 11.4 | <1 | <1 | <1 | <1 |
| 9 | | 5.6 | | 10.1 | <1 | <1 | <1 | <1 |
| 10 | | 5.0 | | 10.7 | <1 | <1 | <1 | <1 |
| 11 | | 6.5 | | 9.0 | <1 | <1 | <1 | <1 |
| 12 | | 4.8 | | 8.7 | <1 | <1 | <1 | <1 |
| 13 | | 4.9 | | 8.7 | <1 | <1 | <1 | <1 |
| 14 | | 5.6 | | 8.7 | <1 | <1 | <1 | <1 |
| 15 | | 6.4 | | 7.4 | <1 | <1 | <1 | <1 |

None of the processes utilizing maximum vacuum (Processes 1, 2, 3, and 6) produced zero air gap after 5 days. However, there was stopper movement for two non-maximum vacuum processes (Processes 4 and 5).

These results confirm that in order to initiate stopper movement, a critical amount of a soluble gas (e.g. $CO_2$) headspace is needed to create enough vacuum difference and drive down the stopper and eliminate the headspace. In the maximum vacuum conditions, the stopper achieves partial contact with the liquid shortly after stoppering and before cold incubation. In these cases, the minor pressure change due to $CO_2$ dissolution is not enough to initiate the further stopper movement to close the remaining gap despite it being a small gap.

Surprisingly, syringes with high amounts of silicone oil did not perform as well as syringes with low amounts of silicone oil in reducing headspace. This is surprising since the higher amount of lubricant was expected to better facilitate stopper movement, even if there was a small initial headspace. These results indicate that a more uniform silicone oil distribution, even of a low amount, is more important than high silicone oil level.

Example 7. Optimizing Vacuum

Various vacuum pressures was evaluated to determine the impact on eliminating headspace from syringes. Groups of syringes filled with buffered aqueous solution were subjected to the following procedures.

Place syringes in a vacuum stoppering unit. Pull maximum vacuum for 4 seconds to remove air from the chamber and syringes. Repressurize chamber back to atmospheric pressure with $CO_2$. Pull vacuum again at 29.7, 28.7, 27.5, 27.0, 26.5, or 26.0 inHg for 4 seconds. Stopper the syringes. Immediately after stoppering, the air gap was measured the syringes. Syringes were incubated at 5° C. The headspace in syringes was evaluated at various time points during incubation. The table below reports the number of syringes in each group that exhibited zero headspace.

TABLE 7

| Vacuum (in Hg) | Starting Air Gap in Syringe (mm) | Number of Syringes with Zero Air Gap After Incubation | | | | | |
|---|---|---|---|---|---|---|---|
| | | 18 hours | 2 days | 3 days | 4 days | 5 days | 6 days | 7 Days |
| 29.7 | <1 | 4 of 5 | 4 of 5 | NA | 5 of 5 | 5 of 5 | 5 of 5 | 5 of 5 |
| 28.7 | <1 | 0 of 5 | 3 of 5 | NA | 3 of 5 | 4 of 5 | 5 of 5 | 5 of 5 |
| 27.5 | 3.4 | 0 of 5 | 0 of 5 | NA | 5 of 5 | 5 of 5 | 5 of 5 | 5 of 5 |
| 27 | 4 | 0 of 5 | 0 of 5 | 0 of 5 | 0 of 5 | NA | NA | NA |
| 26.5 | 4.4 | 0 of 5 | 0 of 5 | NA | 0 of 5 | 0 of 5 | 0 of 5 | 0 of 5 |
| 26 | 4.6 | 0 of 15 | 0 of 15 | NA | 0 of 15 | 0 of 15 | 0 of 15 | 0 of 15 |

It is surprising that that processes with vacuum of at least 27.5 inHg (pulled vacuum strength) effectively produced syringes with zero headspace with just a single cycle of degassing and repressurizing with $CO_2$. It is expected that longer vacuum times at less vacuum will also produce syringes with zero headspace. Alternatively, applying multiple cycles of degassing and repressurizing with $CO_2$ is also expected to produce syringes with zero headspace.

Example 8. Method Conditions

Four processes were evaluated for the ability to produce a container with no headspace. Aqueous solutions were evaluated in syringes.

Process 1

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum again. Stopper the syringes.

Process 2

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 27.0 inHg vacuum again. Stopper the syringes.

Process 3

Place syringes in a vacuum stoppering unit. Pull 28.5 inHg vacuum to remove air from the chamber and syringes. Repressurize chamber back to atmospheric pressure with $CO_2$. Pull 28.5 inHg vacuum to remove $CO_2$ from the chamber and syringes. Repressurize chamber back to atmospheric pressure with $CO_2$; purge with $CO_2$ for 5 minutes. Pull 27.0 inHg vacuum again. Stopper the syringes.

Process 4

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 27.0 inHg vacuum again. Stopper the syringes.

After stoppering, syringes were then stored at 1-10° C. and evaluated for headspace at 18 hours, 2 days, 3 days, and 4 days. Fifteen syringes were evaluated for each process. Results of these processes are found in Table 8 below.

TABLE 8

| Process | Starting Air Gap in Syringe (mm) | Number of Syringes with Zero Air Gap After Incubation | | | |
|---|---|---|---|---|---|
| | | 18 hours | 2 days | 3 days | 4 days |
| 1 | <1 | 7 | 13 | 15 | 15 |
| 2 | 3 | 0 | 14 | 15 | 15 |
| 3 | 3.2 | 0 | 14 | 15 | 15 |
| 4 | 3.4 | 0 | 14 | 14 | 15 |

Each process produced syringes with zero headspace within four days of incubation. The majority of syringes had zero headspace within 2 days of incubation.

Example 9. Impact of $CO_2$ Exposure Time

The impact of $CO_2$ exposure during the zero headspace processes was evaluated for protein formulations. The protein formulations were exposed to $CO_2$ for the specified time then incubated for 10 days at 40° C. Formulations were evaluated for the presence of visible particles. Results can be seen in Table 9 below.

TABLE 9

| Formulations | $CO_2$ Exposure Time (minutes) | | | | |
|---|---|---|---|---|---|
| | 0 | 10 | 20 | 30 | 60 |
| 30 mM His, 20 mM Arg, 240 mM Gly, pH 5.2 | No Visible Particles | No Visible Particles | Visible Particles | Visible Particle | Visible Particle |
| 30 mM His, 15 mM NaCl, 240 mM Gly, pH 5.2 | No Visible Particles | Visible Particles | Visible Particles | Visible Particle | Visible Particle |

After incubation for 10 days, formulations that were not exposed to $CO_2$ did not have any visible particles. Surprisingly, the formulation with arginine that was exposed to $CO_2$ for 10 minutes did not produce visible particles during incubation. This result was further surprising since the formulation with NaCl, but not arginine, did show visible particles upon 10 minutes of exposure to $CO_2$.

To mitigate the potentially destabilizing effects of $CO_2$ on protein formulations various approaches can be taken. One is to limit the $CO_2$ exposure time to no more than 10 minutes. For the zero headspace methods $CO_2$ exposure time can be reduced even further to 5 minutes or less, or 3 minutes or less to produce stable protein formulations in containers with zero headspace.

Additionally, the combination of salt and $CO_2$ exposure appear to be destabilizing to protein formulations. Therefore, formulations excluding salts can be used in the zero headspace methods to produce stable formulations in containers with zero headspace.

Example 10. Evaluation of Zero Headspace Processes on Solutions

The impact of processes that produce zero headspace containers was evaluated for an aqueous solution. Aqueous solutions placed in syringes and subjected to the processes below to create zero headspace syringes.

Process 1

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum again. Repressurize the chamber back to atmospheric pressure with $CO_2$. Pull a 28.5 inHg vacuum again. Stopper the syringes.

Process 2

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 27.0 inHg vacuum again. Stopper the syringes.

Process 3

Place syringes in a vacuum stoppering unit. Pull a 28.5 inHg vacuum to remove air from the chamber and syringes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$; purge with $CO_2$ for 5 minutes. Pull a 27.0 inHg vacuum again. Stopper the syringes.

Process 4

Place syringes in a vacuum stoppering unit. Pull a 28.5 inHg vacuum to remove air from the chamber and syringes, hold the vacuum for 5 minutes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 28.5 inHg vacuum to remove $CO_2$ from the chamber and syringes. Repressurize the chamber back to atmospheric pressure with $CO_2$. Pull a 27.0 inHg vacuum again. Stopper the syringes.

Fifteen syringes were evaluated for each process. Syringes were filled with 0.8 mL of an aqueous solution with a pH of 5.2. Syringes were subjected to the process to create a zero headspace syringe then stored at 5° C. and for 6 days. Results can be seen in Table 10 below.

TABLE 10

| Process | Syringe | Filled Weight (g) | Recovered weight (g) | Osmolality (mmol/kg) | pH |
|---|---|---|---|---|---|
| 1 | 21 | 0.805 | 0.802 | 299 | 5.08 |
| 2 | 36 | 0.802 | 0.798 | 297 | 5.10 |
| 3 | 51 | 0.806 | 0.799 | 299 | 5.12 |
| 4 | 66 | 0.806 | 0.803 | 298 | 5.13 |

One syringe from each process was selected for evaluation. The results in the table 10 above demonstrate that zero headspace processes do not result in any significant loss of filled solution. Also despite exposure to vacuum and $CO_2$, the pH changed less than 3%. Additionally, osmolality remained within 250-350 mmol/kg, the range of isotonicity. These results demonstrate that the zero headspace methods of the invention do not have a detrimental impact on solutions. Therefore, pharmaceutical formulations in syringes with zero headspace are suitable for administration to subjects.

Example 11. Stability of Formulations in Zero Headspace Containers

The stability of protein formulations in containers with zero headspace was evaluated over time. Evaluations include, but are not limited to: pH, protein concentration, size exclusion chromatography, cation exchange chromatography, CE-SDS (reducing and non-reducing), potency, clarity (NTU), visual inspection (clarity, turbidity, particles), and sub-visible particles. Storage temperature and times may include: −40° C. for 1, 3, 6, and 12 months; 2-8° C. for 1, 3, 6, and 12 months; and 25° C. for 2 weeks, 1 month, 3 months, and 6 months; and 40° C. for 1, 2, and 4 weeks.

A buffered adalimumab formulation with a pH of 5.2 was evaluated. The formulation did not contain a polyol, sugar, or a surfactant. The formulation was placed in syringes with zero headspace using method of the present invention. Syringes were stored at 5° C., 25° C., and 40° C. and measurements were taken over time. Table 11 below summarizes the results.

TABLE 11

| Temp (° C.) | Time (days) | pH | Conc (mg/mL) | SEC (%) | | | Visual | Particulate per container | |
|---|---|---|---|---|---|---|---|---|---|
| | | | | Main | Aggregate | Post Peak | | ≥10 mm | ≥25 mm |
| 5 | 0 | 5.3 | 49.7 | 99.8 | 0.1 | 0.1 | Clear | 250 | 88 |
| | 30 | 5.4 | 48.6 | 99.5 | 0.1 | 0.4 | Clear | 426 | 169 |
| | 90 | NA | NA | 99.3 | 0.1 | 0.6 | Clear | 175 | 42 |
| 25 | 0 | 5.3 | 49.7 | 99.8 | 0.1 | 0.1 | Clear | 250 | 88 |
| | 14 | 5.3 | 49.3 | 99.7 | 0.1 | 0.2 | Clear | 105 | 31 |
| | 30 | 5.4 | 49.2 | 99.4 | 0.1 | 0.4 | Clear | 725 | 186 |
| | 90 | NA | NA | 99.0 | 0.2 | 0.9 | Clear | 183 | 5 |
| 40 | 0 | 5.3 | 49.7 | 99.8 | 0.1 | 0.1 | Clear | 250 | 88 |
| | 7 | 5.3 | 49.0 | 99.7 | 0.1 | 0.2 | Clear | 257 | 40 |
| | 14 | 5.2 | 49.3 | 99.6 | 0.1 | 0.3 | Clear | 159 | 38 |
| | 30 | 5.5 | 47.4 | 98.9 | 0.2 | 0.9 | Clear | 1143 | 192 |

The results above demonstrate that a protein formulation in a zero headspace container of the present invention is stable. It is surprising that a protein formulation that does not contain a polyol, sugar, or surfactant can be stabilized since polyols and surfactants are typically added to stabilize protein formulations. In fact, all Humira® (adalimumab) formulations contain a polyol and surfactant and the formulation for Amjevita™ (adalimumab biosimilar) contains sugar and surfactant. These results show for the first time that protein formulations can be stabilized in containers with zero headspace without the need for additional excipients such as polyols, sugars, and surfactants.

Example 12. Devices for Producing Zero Headspace Containers

Process

A device—a SA25 workcell—was configured to perform the filling, vacuum, purging, and stoppering steps of the present invention to prepare a container with no headspace. The device is a contained and automated fill and finish workcell. The device fills the container in a filling chamber then transfers the filled containers to a stoppering chamber. The stoppering chamber is sealed and vacuum is applied to degas the aqueous solution. The stoppering chamber is purged with soluble gas and then the container is closed.

In all processes described below syringes were filled with an aqueous solution, subjected to a vacuum, purged with the soluble gas $CO_2$, and the syringes were closed with stoppers. To determine operational parameters, in some processes the vacuum and purging steps were repeated a number of times and the length of the purging step was varied.

Process Performance

Fill volume target was 0.8 mL per syringe. Average fill volume was 0.8014 mL, stdDev 0.0023 mL. The device achieved filling process accuracy within +/−2% alert limits and +/−4% action limits.

A vacuum decay of 0.033 mbar/min under 0.11 mbar was observed for the stoppering chamber indicating a good seal and the ability to maintain vacuum.

Consistent headspace was achieved when closing the syringes with stoppers.

In total, the device was successfully configured to perform the filling, vacuum, purging and closing steps of the present invention.

Water Filled Syringe Results

Syringes were filled with water to test the ability of the device to produce containers with zero headspace. Vacuum setpoints of 45, 50, and 60 mbar were evaluated. For the 45 mbar and 50 mbar setpoints, no headspace was visibly detected in less than one day and for the 60 mbar setpoint, in less than 2 days. Additionally, very small bubbles observed on bottom syringe wall for some syringes previously disappeared in less than two days.

Vacuum testing confirmed zero headspace in syringes subjected to all vacuum setpoints.

Buffer Filled Syringe Results

Syringes were filled with buffered solutions to test the ability of the device to produce containers with zero headspace. The table below demonstrates that the device configured with various vacuum setpoints, number of vacuum and purge cycles, and hold times produces containers with zero headspace.

TABLE 12

| Tub # | Vacuum Setpoint/ # of Cycle/ Hold Time | Headspace Size | Small Bubbles | Vacuum Testing |
| --- | --- | --- | --- | --- |
| 8 | 40 mbar/2/5 min | Zero | Zero | Pass |
| 9 | 40 mbar/2/4 min | Zero | Zero | Pass |
| 10 | 40 mbar/2/3 min | Zero | Zero | Pass |
| 25 | 45 mbar/2/5 min | Zero | Zero | Pass |
| 26 | 45 mbar/2/4 min | Zero | Zero | Pass |
| 27 | 45 mbar/2/3 min | Zero | Zero | Pass |
| 14 | 45 mbar/1/5 min | Zero | Zero | Pass |
| 15 | 45 mbar/1/4 min | Zero | Zero | Pass |
| 16 | 45 mbar/1/3 min | Zero | Zero | Pass |

These results confirm the methods for producing container with zero headspace are robust and that devices can be configured to produce containers with zero headspace.

pH Stability in Containers with Zero Headspace

The pH of a solution in containers produced by methods for creating containers zero headspace were compared to the pH of a solution in a standard container with a headspace. The table below demonstrates that pH of a solution was not significantly affected by the zero headspace methods.

TABLE 13

| Tub # | Vacuum Setpoint/ # of Cycle/ Hold Time | pH (ZHS Syringe) | pH (Control) | pH Change | % change from control |
| --- | --- | --- | --- | --- | --- |
| 8 | 40 mbar/2/5 min | 5.17 | 5.22 | 0.05 | −0.96% |
| 9 | 40 mbar/2/4 min | 5.2 | 5.22 | 0.02 | −0.38% |
| 10 | 40 mbar/2/3 min | 5.19 | 5.22 | 0.03 | −0.57% |
| 25 | 45 mbar/2/5 min | 5.18 | 5.22 | 0.04 | −0.77% |
| 26 | 45 mbar/2/4 min | 5.18 | 5.22 | 0.04 | −0.77% |
| 27 | 45 mbar/2/3 min | 5.19 | 5.22 | 0.03 | −0.57% |
| 14 | 45 mbar/1/5 min | 5.16 | 5.22 | 0.06 | −1.15% |
| 15 | 45 mbar/1/4 min | 5.19 | 5.22 | 0.03 | −0.57% |
| 16 | 45 mbar/1/3 min | 5.2 | 5.22 | 0.02 | −0.38% |

The pH changed by less than 1% in most containers, regardless of the parameters used to create a zero headspace container. These results confirm that solutions with zero headspace, even when a $CO_2$ headspace has been dissolved into the solution have a stable pH.

Drug Product Filled Syringe Results

Seven drug product fill runs were completed over four days. The drug substance was an antibody—adalimumab biosimilar—in various formulations. One purpose was to test the robustness of the device to reliably produce thousands syringes with zero headspace over a short period of time. Another was to determine if various formulations of aqueous drug substance solutions are stable in containers with zero headspace.

In addition to the antibody, formulation contained the excipients in the table below. All of the formulations are free of surfactant. All of the formulations are free of polyol. All of the formulations are free of sugars. Formulations 1 and 2 are free of salt. Formulations 3, 4, 5, and 6 are free of buffer.

TABLE 14

| Formulation Lot # | Formulation Details |
| --- | --- |
| CHS-DS1-1 | 30 mM His, 25 mM Arg, 230 mM Gly, pH 5.2 |
| CHS-DS1-2 | 30 mM His, 25 mM Arg, 230 mM Gly, pH 5.2 |
| CHS-DS1-3 | 35 mM NaCl, 140 mM Gly, 65 mM HPβCD pH 5.2 |
| CHS-DS1-4 | 35 mM NaCl, 140 mM Gly, 65 mM HPβCD pH 5.2 |
| CHS-DS1-5 | 45 mM Arg, 140 mM Gly, 20 mM $CaCl_2$, pH 5.2 |
| CHS-DS1-6 | 45 mM Arg, 140 mM Gly, 15 mM $CaCl_2$, 30 mM Thr pH 5.2 |

TABLE 14-continued

| Formulation Lot # | Formulation Details |
|---|---|
| CHS-DS1-7 | 20 mM His, 25 mM NaCl, 140 mM Gly, 65 mM HPβCD pH 5.2 |

Containers filled with these formulations with the zero headspace method were evaluated for the presence of headspace and other defects.

TABLE 15

| Formulation Lot # | Visible Particle | Headspace | Bubble | Other Defects (syringes with defects/ syringes produced in lot)* |
|---|---|---|---|---|
| CHS-DS1-1 | Zero | Zero | Zero | 7/1000 = 0.7% |
| CHS-DS1-2 | Zero | Zero | Zero | 4/400 = 1% |
| CHS-DS1-3 | Zero | Zero | Zero | 4/1000 = 0.4% |
| CHS-DS1-4 | Zero | Zero | Zero | 13/900 = 1.4% |
| CHS-DS1-5 | Zero | Zero | Zero | 5/900 = 0.6% |
| CHS-DS1-6 | Zero | Zero | Zero | 3/900 = 0.3% |
| CHS-DS1-7 | Zero | Zero | Zero | 2/200 = 1% |

*Including missing stopper, double stoppers, fibers, and glass defects

The seven fill runs were completed over four days with 5300 syringes filled with the pharmaceutical formulation. Syringes were filled in tubs of 100 syringes. Syringes were inspected for a headspace within five days of filling. Upon inspection, syringes in 52 of the 53 tubs had zero headspace. Incubation of syringes at 2-8° C. continued. At the next inspection, seven day later, syringes in the last tub had zero headspace.

The rate of defects observed in syringes with the pharmaceutical formulation that had zero headspace were low. These defect rates are acceptable for commercial product manufacturing.

These results demonstrate that a device can be configured to perform the method of creating a container with an aqueous drug substance solution that has zero headspace. The device used here reliably produced syringes with no headspace, no bubbles, and no visible particles. Additionally, the defect rate was low and comparable to defect rates seen in standard filling methods. The defect rate for containers produced by the methods of creating zero headspace is equal to or better than the defect rate for traditional methods of producing containers with a headspace.

Additionally, an aqueous drug substance solution in a container with zero headspace is stable. In particular, aqueous drug substance solution that do not have a surfactant or a polyol are stable in containers with zero headspace. Likewise, aqueous drug substance solutions that do not contain a buffer are stable in containers with zero headspace. Formulations 1-7 above are specific examples of aqueous drug substance solutions that are stable in containers with zero headspace.

Example 13. Creating Zero Headspace in Containers with Various Formulation Fill Volumes The ability to create zero headspace syringes filled with varying amounts of aqueous drug product buffer was evaluated.

In this example, a formulation comprising a small molecule susceptible to oxidative degradation (methionine) was filled at 0.8 mL, 0.6 mL, and 0.4 mL into syringes using the methods of the present invention.

Briefly, syringes were filled with the solution, vacuum was applied to the syringes with the solution for period of time, carbon dioxide was flooded into the chamber with the syringes, vacuum was again applied to the syringes with the solution for period of time, syringes were closed with a stopper so that there was a headspace at time of closure. Syringes were then stored and observed for reduction or elimination of the headspace.

To test the robustness of the method, the vacuum setpoint (mbar pressure in chamber) and the vacuum duration (dwell time) was varied. A tub of 100 syringes was filled for each variation of the method tested. Table 16 reports the results this evaluation.

TABLE 16

| Tub # | Formulation Fill Volume (mL) | Vacuum Setpoint (mbar) | Dwell Time (s) | Elapsed time from fill to 1st inspection (days) | Detectable Headspace at 1st inspection (mm) |
|---|---|---|---|---|---|
| 1 | 0.8 | 45 | 120 | 3 | 0 |
| 5 | 0.8 | 40 | 180 | 2 | 0 |
| 9 | 0.8 | 40 | 120 | 2 | 0 |
| 13 | 0.8 | 40 | 60 | 2 | 0 |
| 17 | 0.8 | 45 | 60 | 2 | 0 |
| 2 | 0.6 | 45 | 120 | 3 | 0 |
| 6 | 0.6 | 40 | 180 | 2 | 0 |
| 10 | 0.6 | 40 | 120 | 2 | 0 |
| 14 | 0.6 | 40 | 60 | 2 | 0 |
| 18 | 0.6 | 45 | 60 | 2 | 0 |
| 3 | 0.4 | 45 | 120 | 2 | 0 |
| 7 | 0.4 | 40 | 180 | 2 | 0 |
| 11 | 0.4 | 40 | 120 | 2 | 0 |
| 15 | 0.4 | 40 | 60 | 2 | 0 |
| 19 | 0.4 | 45 | 60 | 2 | 0 |

One thousand five hundred syringes were filled with an aqueous formulation and all achieved zero headspace.

Applying a vacuum of 40 or 45 mbar was sufficient to a achieve a zero headspace indicating that the method is not particularly sensitive to a specific vacuum pressure. In other words, a low pressure headspace of a soluble gas can be absorbed into 0.8 mL, 0.6 mL, and 0.4 mL of aqueous formulation to create a syringe with zero headspace.

Likewise, the method was not particularly sensitive to duration that vacuum was applied. A vacuum duration of 180, 120, or 60 seconds was sufficient to a achieve a zero headspace. Thus, a vacuum can be applied for short duration and still sufficiently remove atmosphere from the syringe and aqueous formulation so that a low pressure soluble gas headspace can be created to achieve a zero headspace.

Syringes with zero headspace had insignificant pH changes. Thus, process for creating a container with zero headspace, including the absorption a low pressure soluble gas into the aqueous solution, does not significantly affect the characteristics of the aqueous solution as formulated. In particular, carbon dioxide did not affect the pH the formulations tested.

Example 14. Creating Zero Headspace in Containers with a High Concentration Protein Aqueous Solution In this example, three different high concentration protein solution were filled at 0.4 mL into syringes using the methods of the present invention. In addition to evaluating the impact of high concentration protein in the method, solutions contained various combinations of excipients.

Formulation #1 (1420-HC #1) is free of buffer, polyol, and surfactant: 100 mg/mL adalimumab, 40 mM NaCl, 90 mM Gly, 65 mM HPβCD, pH 5.2.

Formulation #2 (1420-HC #2) is free of salt, polyol, and surfactant: 100 mg/mL adalimumab, 20 mM His, 40 mM Arg, 190 mM Gly, pH 5.2.

Formulation #3 (1420-HC #3) is free of buffer, polyol, HPβCD, and surfactant: 100 mg/mL adalimumab, 45 mM Arg, 140 mM Gly, 20 mM $CaCl_2$, pH 5.2.

Briefly, syringes were filled with the solution, vacuum was applied to the syringes with the solution for period of time, carbon dioxide was flooded into the chamber with the syringes, vacuum was again applied to the syringes with the solution for period of time, syringes were closed with a stopper so that there was a headspace at time of closure. Syringes were then stored and observed for reduction or elimination of the headspace.

To test the robustness of the method the vacuum setpoint (mbar pressure in chamber) was varied. Table 17 reports the results of this evaluation.

TABLE 17

| Formulation # | Tub # | Fill Volume (mL) | Vacuum Setpoint (mbar) | Time until ZHS (days) |
|---|---|---|---|---|
| 1420-HC #3 | 32.1 | 0.43 | 45 | 89% @ 4 |
| 1420-HC #3 | 32.2 | 0.43 | 45 | 4 |
| 1420-HC #3 | 32.3 | 0.43 | 40 | 3 |
| 1420-HC #3 | 32.4 | 0.43 | 40 | 3 |
| 1420-HC #2 | 33.1 | 0.43 | 45 | 3 |
| 1420-HC #2 | 33.2 | 0.43 | 45 | 3 |
| 1420-HC #2 | 33.3 | 0.43 | 40 | 3 |
| 1420-HC #1 | 34.1 | 0.43 | 45 | 3 |
| 1420-HC #1 | 34.2 | 0.43 | 45 | 4 |
| 1420-HC #1 | 34.3 | 0.43 | 40 | 4 |
| 1420-HC #1 | 34.4 | 0.43 | 40 | 3 |

The results demonstrate that applying a vacuum of 40 or 45 mbar was sufficient to a achieve a zero headspace. In tub 32.1, 89% of the syringes had zero headspace at four days after filling. Not all syringes achieved zero headspace in this tub because the filling machine not starting the stoppering cycle on time. Therefore, the zero headspace process can achieve zero headspace at 45 mbar of pressure as demonstrated with tub 32.2 (which used the same parameters at tub 32.1).

These results demonstrate that zero headspace can be achieved with aqueous solutions of high concentration protein. Thus, the method is useful for preparing a container with zero headspace, regardless of the concentration of molecule of interest in solution (i.e. the active pharmaceutical ingredient in a drug product).

These results demonstrate that zero headspace can be achieved with aqueous solutions, regardless of excipient composition. Thus, the method is useful for preparing a container with zero headspace for any aqueous solution.

The results further confirm that the method is not particularly sensitive to a specific vacuum pressure. In other words, a low pressure headspace of a soluble gas can be absorbed into 0.4 mL of high concentration protein solution to create a syringe with zero headspace.

Example 15. Creating Zero Headspace in Containers with Various Aqueous Solutions In this example, solutions of various molecules are evaluated to determine if the method of the present invention can be used to create containers with zero headspace and stabilize solutions of various molecules.

Pegfilgrastim

An aqueous pegfilgrastim solution was filled at 0.6 mL into syringes using the methods of the present invention. The formulation comprised 10 mg/ml pegfilgrastim, buffer, stabilizer, and surfactant, at pH 4.0.

The vacuum setpoint (mbar pressure in chamber) was varied in the process. As a control, an aqueous pegfilgrastim solution was filled into syringes and was vacuum stoppered at 70 mbar without being cycled/purged with a soluble gas. Table 18 reports the results of the evaluation.

TABLE 18

| Fill Method | Tub # | Fill Volume (mL) | Vacuum Setpoint (mbar) | Dwell Time (s) | Time until ZHS (days) |
|---|---|---|---|---|---|
| Control Method | 29.2 | 0.63 | 70 | N/A | N/A |
| ZHS Method | 29.1 | 0.63 | 45 | 120 | 4 |
| ZHS Method | 29.3 | 0.63 | 40 | 120 | 4 |
| ZHS Method | 29.4 | 0.63 | 40 | 120 | 4 |
| ZHS Method | 29.5 | 0.63 | 40 | 120 | 4 |
| ZHS Method | 29.6 | 0.63 | 40 | 120 | 3 |
| ZHS Method | 29.7 | 0.63 | 40 | 120 | 3 |

The syringes filled with control method did not result in zero headspace, despite being stored under the same conditions as the syringes filled with the zero headspace method. This confirms that the creation of a soluble gas headspace is required to create a container with zero headspace.

These results also demonstrate that zero headspace can be achieved with aqueous solutions of a PEGylated protein. Additionally, the results demonstrate that process can be used with a solution containing a low concentration of the molecule of interest.

It was surprising that the zero headspace could be achieved and maintained in a solution with a low pH of 4.0. Based on the low pressure soluble gas headspace created by the method, it is expected that solutions with a pH as low as about 2 can be used in the zero headspace method.

Thus, the method is useful for preparing a container with zero headspace, regardless of the of molecule of interest in solution (i.e. the active pharmaceutical ingredient in a drug product). Additionally, the method can be used to prepare containers with zero headspace for solutions over a wide range of pH—about pH 3 to about pH 9.

Other Molecules

An aqueous solution of a molecule of interest is filled into containers using the methods of the present invention. Molecules of interest include Met (a small organic molecule), N-Ac-Trp (a small organic molecule), Doxycicline (an antibiotic), Teripatatide (a recombinant form of parathyroid hormone), and HSA (human serum albumin, a globular protein).

A container filled with the solution containing a molecule of interest using the method of the present invention results in zero headspace.

Conclusion

This example, combined with results from examples 13 and 14 demonstrate that the method for creating a container with zero headspace is not limited a solution of a specific molecule, a specific concentration of the molecule, a specific formulation of excipients, or a specific fill volume of the solution within the container. Therefore, the method for creating a container with zero headspace can be used with an aqueous solution of any molecules, at any concentration of the molecule, with any formulation of excipients, and at any fill volume in the container.

In additional testing, it was discovered that the amount of headspace created in the syringe at the time of stoppering can be controlled by pressure at which vacuum stoppering is conducted. For instance, vacuum pressures of 140 mbar, 70 mbar, and 60 mbar resulted in headspace heights of 6 mm, 4 mm, and 3 mm, respectively in the syringes.

Example 16. Comparison of Particles in Formulations in Containers with Zero Headspace Vs Formulations in Containers with Headspace This example evaluated the stabilizing effect of preparing an aqueous drug substance solution in a container with zero headspace. Various formulations that were free of excipients typically used to stabilize drug substances (e.g. buffer, salt, polyol, surfactant) were evaluated.

Formation of visible and subvisible particles was evaluated in (i) aqueous drug substance solution in a container with zero headspace and (ii) aqueous drug substance solution comprising stabilizing excipients in containers with headspace and with zero headspace. The same drug substance was used when aqueous drug substance solution were compared to one another.

Formulations

Control: a 50 mg/mL adalimumab formulation comprising buffer and surfactant.

CHF: a buffered polyol and surfactant free formulation (50 mg/mL Adalimumab, 20 mM His, 140 mM Gly, 25 mM NaCl, 65 mM HPβCD, pH 5.2). Formulations that contain HPβCD are expected to be stable even when the formulation is free of a surfactant.

CHG: a buffer free, polyol free, and surfactant free formulation (50 mg/mL adalimumab, 140 mM Gly, 35 mM NaCl, 65 mM HPβCD, pH 5.2).

CHH: a buffered formulation free of polyol, salt, and surfactant (50 mg/mL adalimumab, 30 mM His, 230 mM Gly, 25 mM Arg, pH 5.2).

CHI: a buffer free, polyol free, and surfactant free formulation; variant a (50 mg/mL Adalimumab, 140 mM Gly, 45 mM Arg, 20 mM CaCl2, pH 5.2), variant b (50 mg/mL Adalimumab, 140 mM Gly, 45 mM Arg, 15 mM CaCl2, 30 mM Thr, pH 5.2).

Commercially available Humira (0.8 mL containing adalimumab 40 mg, citric acid monohydrate 1.04 mg, dibasic sodium phosphate dihydrate 1.22 mg, mannitol 9.6 mg, monobasic sodium phosphate dihydrate 0.69 mg, polysorbate 80 0.8 mg, sodium chloride 4.93 mg, sodium citrate 0.24 mg, at pH 5.2). Humira is supplied in a syringe with a headspace.

The control, CHF, and CHG formulations were filled in syringes with a headspace. Formulations CHH, CHIa and CHIb were filled using method of the present invention in a syringe with zero headspace.

The control formulation was filled in Hypak PFS for biotech and closed with siliconized 4023 stopper. CHF, CHG, CHH, and CHI formulations were filled in standard Hypak PFS and closed with non-siliconized 4023 stopper. The total target silicone level is similar between the two kinds of syringes. Additionally, the silicone level on the stopper is very low, and these differences should not impact on the final silicone oil level in the product.

Despite the differences in the silicone oil content, the results below are considered to demonstrate that formulations without a surfactant, in particular formulations in zero headspace containers, are stable.

Visible Particles

Table 19 summarizes the visual appearance of the formulations after the formulation was subjected to various stress and storage conditions.

TABLE 19

|  | CHF | CHG | CHH | CHI |
|---|---|---|---|---|
| After preparation and filling | No Visible particle | No Visible particle | No Visible particle | No Visible particle |
| After storage at 5° C. and 25° C. | No Visible particle | No Visible particle | No Visible particle | No Visible particle |
| After stress at 40° C. | No Visible particle | No Visible particle | No Visible particle | No Visible particle |
| After frozen storage at −40° C. and −70° C. | No Visible particle | No Visible particle | No Visible particle | No Visible particle |
| After shipping | No Visible particle | No Visible particle | No Visible particle | No Visible particle |
| After dropping | No Visible particle | No Visible particle | No Visible particle | No Visible particle |

These results demonstrate that formulations that either contain HPβCD or are in containers with zero headspace are stable, despite being subjected to a wide range of storage temperatures and stress conditions.

Sub-Visible Particle Drop Test

Formulations CHH, CHG, CHIa, and CHIb were evaluated for formation of sub-visible particles after being dropped from bench-top height in a shipping box. The purpose was to evaluate the stabilizing effect of preparing a container with a formulation with the zero headspace method. 0.8 mL of each formulation was filled into syringes with zero headspace using the zero headspace method. Sub-visible particles were evaluated using the MFI 5200 (Protein Simple, San Jose, Calif.).

The amount of sub-visible particles in a formulation was tested before and after the drop. Additionally, to determine if headspace plays a significant role in protecting the formulation, or if the excipients protect the formulation, after the drop tests, a 5 mm high headspace was introduced into the syringes and they were dropped again. Sub-visible particles 10 micrometer (μm) in size and ≥25 μm in size were evaluated. Cut-offs were based on U.S. Pharmacopeial Convention (USP) reference standard 787 titled "Subvisible Particulate Matter In Therapeutic Protein Injections" Cut-offs of: if the container volume is <100 mL, the solution has less than 6000 particles/container >10 micrometer (μm) in size and 600 particles/container >25 μm in size particles/container.

Figure 7:
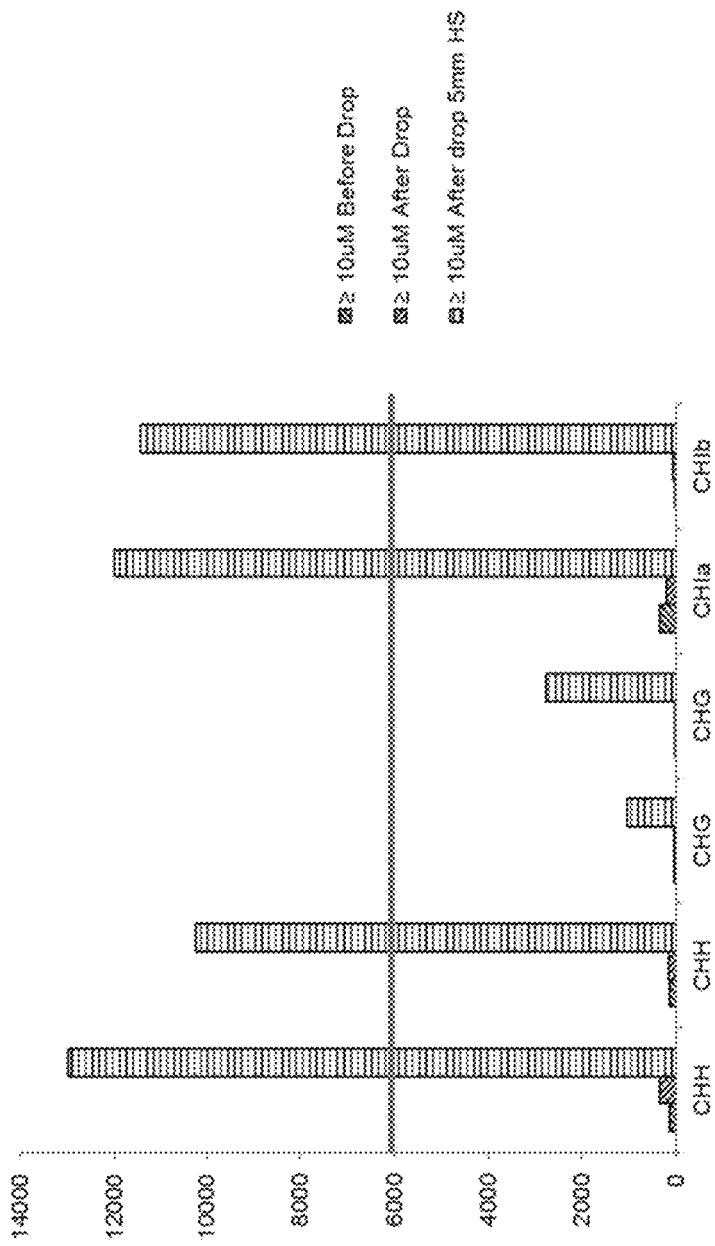
FIG. 7. Sub-visible particles 10 μm in size in solutions in containers with zero headspace before a drop test, after a drop test, and after introduction of a headspace and dropped.
Figure 8:
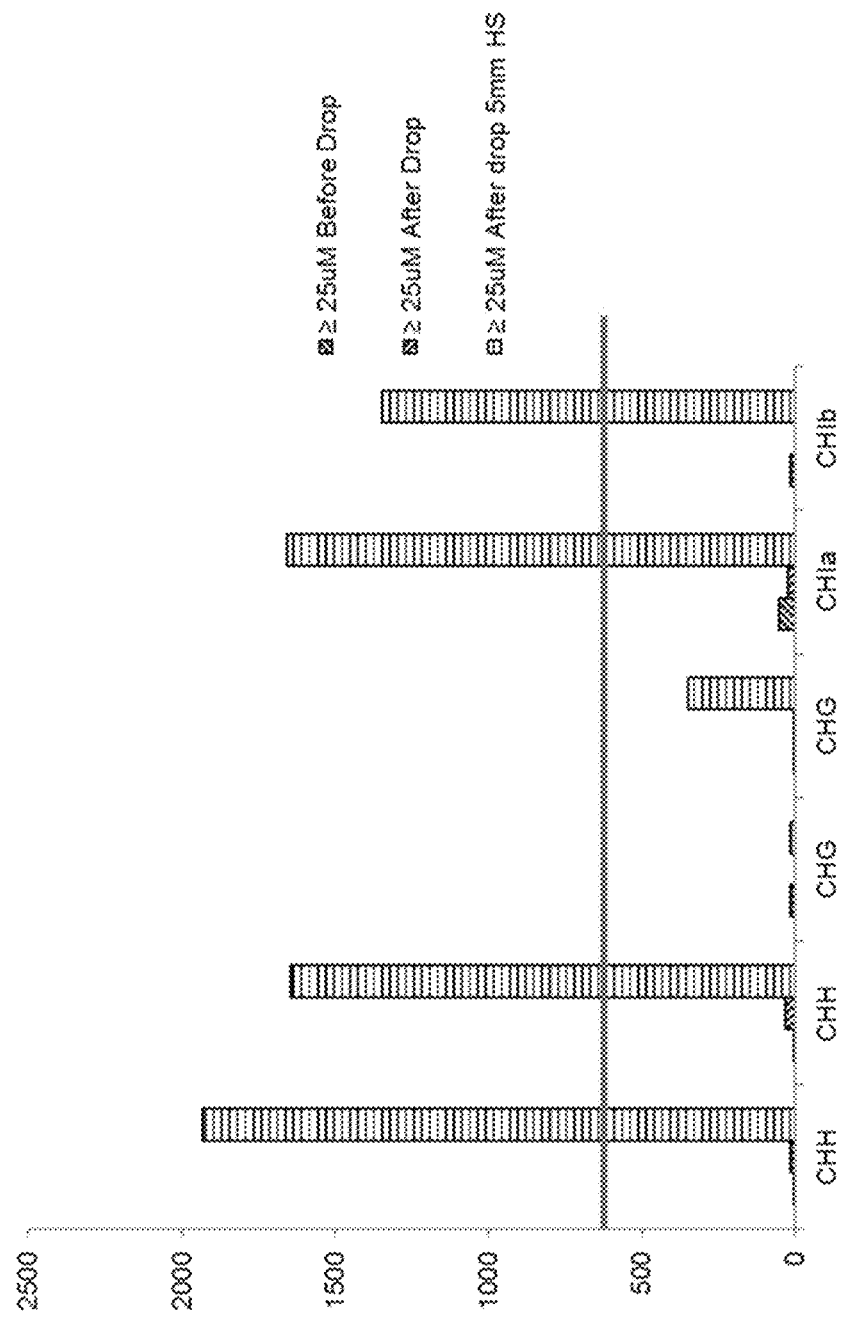
FIG. 8. Sub-visible particles 25 μm in size in solutions in containers with zero headspace before a drop test, after a drop test, and after introduction of a headspace and dropped.

Tables 20 below list particles counts for each formulation before the drop, after the drop, and after introduction of 5 mm of headspace and drop. FIG. 7 provides a graphical representation of the results for sub-visible particles ≥10 μm in size. FIG. 8 provides a graphical representation of the results for sub-visible particles ≥25 μm in size.

TABLE 20

| | Total Particles (counts/Container) | | | | | |
|---|---|---|---|---|---|---|
| | Before Drop | | After Drop | | After inclusion of 5 mm headspace and drop | |
| Formulation | ≥10 uM | ≥25 uM | ≥10 uM | ≥25 uM | ≥10 uM | ≥25 uM |
| CHH | 124 | 6 | 348 | 14 | 12973 | 1932 |
| CHH | 138 | 6 | 160 | 32 | 10248 | 1643 |

TABLE 20-continued

| | Total Particles (counts/Container) | | | | | |
|---|---|---|---|---|---|---|
| | Before Drop | | After Drop | | After inclusion of 5 mm headspace and drop | |
| Formulation | ≥10 uM | ≥25 uM | ≥10 uM | ≥25 uM | ≥10 uM | ≥25 uM |
| CHG | 43 | 13 | 37 | 0 | 1041 | 16 |
| CHG | 7 | 4 | 9 | 5 | 2772 | 347 |
| CHIa | 344 | 52 | 206 | 23 | 11994 | 1655 |
| CHIb | 29 | 14 | 55 | 0 | 11425 | 1346 |

Table 20, FIG. 7, and FIG. 8 show that before and after the drop, all formulations have sub-visible particle counts well below the ≥10 μm in size cut-off of 6000 per container and the ≥25 μm in size cut-off of 600 per container. When a headspace is introduced, the sub-visible particle counts for formulations CHH, CHIa, and CHIb far exceed the cut-off but formulation CHG remains below the cut-off. Formulation CHG contains HPβCD which clearly stabilized the formulation and protects against particle formation when a headspace is present—even in absence of surfactant.

Formulations CHH, CHIa, and CHIb do not contain surfactant, polyol, or HPβCD. CHI formulations is free of buffer. Despite the absence of these stabilizing excipients, when these formulations are present in a container without a headspace they are protected against formation of sub-visible particles and meet the USP guidelines for therapeutic protein injections. When a headspace is introduced to containers with these formulations and are dropped again, the sub-visible particle counts far exceed the USP cut-offs. Therefore, the stability of these formulations in containers with zero headspace is due to the lack of headspace. Removing headspace from a container eliminates the air-water interface and prevents the headspace from mixing the solution which protects the formulation, and the therapeutic molecule, from mechanical stresses and oxidative stress.

Sub-Visible Particles in Formulations with Various Excipients

The amount of sub-visible particles present in aqueous solutions in a container with zero headspace was compared to the sub-visible particles in solutions in containers with a headspace. Sub-visible particles were evaluated using an HIAC instrument from Beckman Coulter (Indianapolis Ind.).

The number of sub-visible particles ≥10 μm in size in syringes were evaluated. All syringes were filled with 0.8 mL of solution. The following syringes were evaluated: syringes with a headspace from 12 lots of control formulation; syringes with a headspace from 2 lots of surfactant-free HPβCD formulations; and syringes with zero headspace from 5 lots of surfactant-free formulations (CHF, CHG, CHH). Results are presented in FIG. 9.

Figure 9:
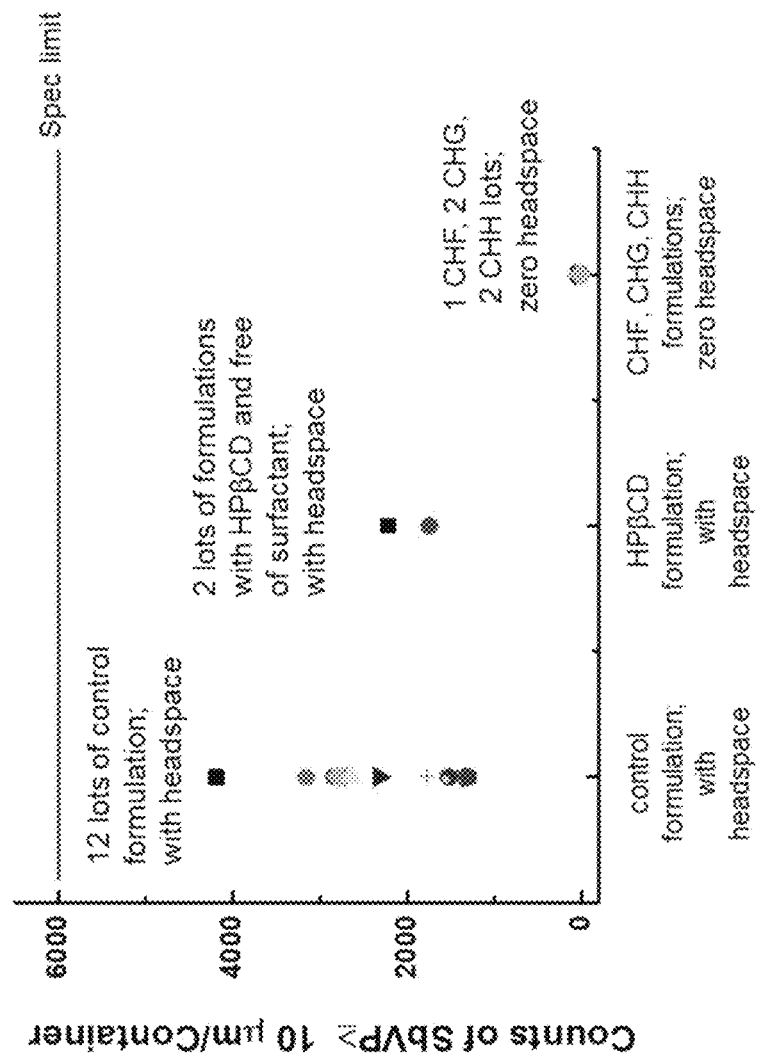
FIG. 9. Sub-visible particles 10 μm in control solution in containers with a headspace, HPβCD solutions in containers with a headspace, and solutions in containers with zero headspace.

FIG. 9 demonstrates that all lots of control formulation, which contains surfactant, have sub-visible particles ≥10 μm below the cut-off despite having a headspace. However, there is variation in the particle count from lot to lot. Surfactant-free HPβCD formulations in syringes with headspace have a lower mean particle count and less lot to lot variation.

Surprisingly, all surfactant-free formulations in syringes with zero headspace have particle counts well below 1000, irrespective of formulation composition. This is lower than particle counts in formulations with surfactant in syringes that have a headspace. Additionally, there is very little lot to lot variation. These results demonstrate that enclosing an aqueous solution in a container with zero headspace provides greater stability for the solution than including a surfactant or other stabilizing excipients (e.g. HPβCD).

While the difference in the syringes and stoppers that contain the control formulation and the syringes and stoppers that contain the zero headspace formulations may contribute to the difference in the sub-visible particles counts, any difference in the syringe and stopper cannot explain the major differences observed in sub-visible particle counts between formulations in syringes with zero headspace and formulations in syringes with a headspace.

Sub-Visible Particle Formation at 40° C. and 25° C.

The amount of sub-visible particles generated over time in aqueous solutions in a container with zero headspace was evaluated. Sub-visible particles were evaluated using the MFI 5200 (Protein Simple, San Jose, Calif.).

The number of sub-visible particles 10 μm in size in syringes were evaluated. All syringes were filled with 0.8 mL of solution. Syringes with zero headspace from 6 lots of surfactant-free formulations (CHG, CHH, CHIa, CHIb) were stored at 40° C. for 30 days and surfactant-free formulations CHIa and CHIb were stored at 25° C. for 60 days. Particle counts from syringes with a headspace from 12 lots of control formulation at time zero are provided for comparison. Results for the 40° C. time course are presented in FIG. 10 and 25° C. degree time course are presented in FIG. 11.

Figure 10:
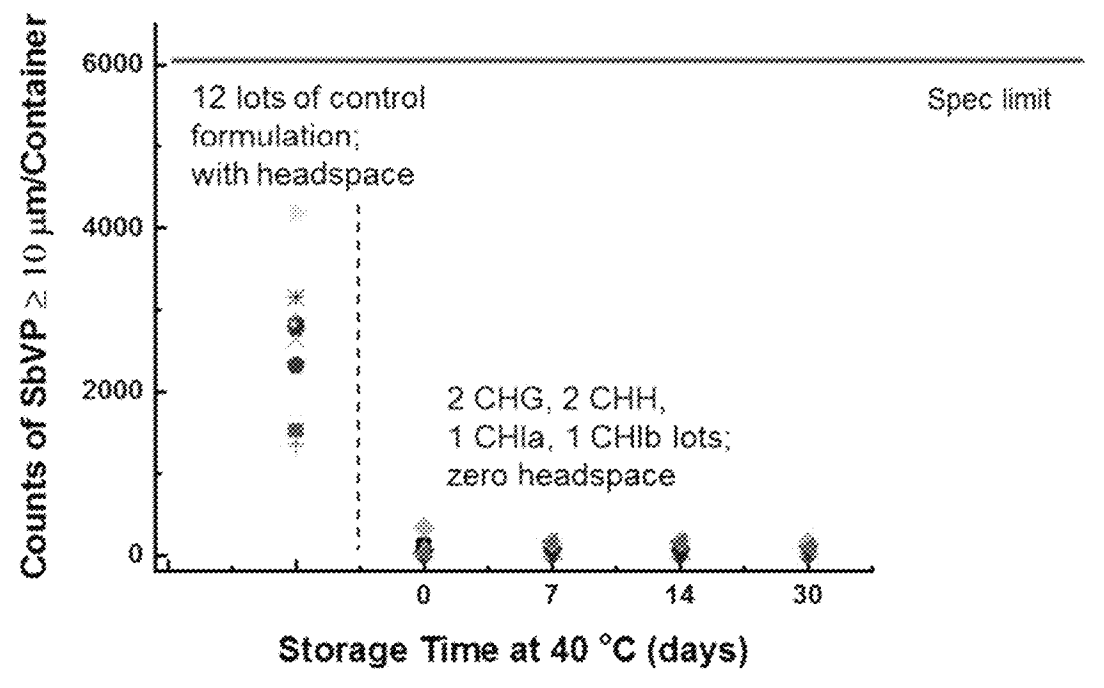

FIG. 10 demonstrates that formulations in syringes with zero headspace, irrespective of the excipients in the formulation, are thermally stable at 40° C. Specifically, the formulations have a less than 1000 sub-visible particles 10 μm in size at time 0, day 7, day 14, and day 30 when stored at 40° C.

Figure 11:
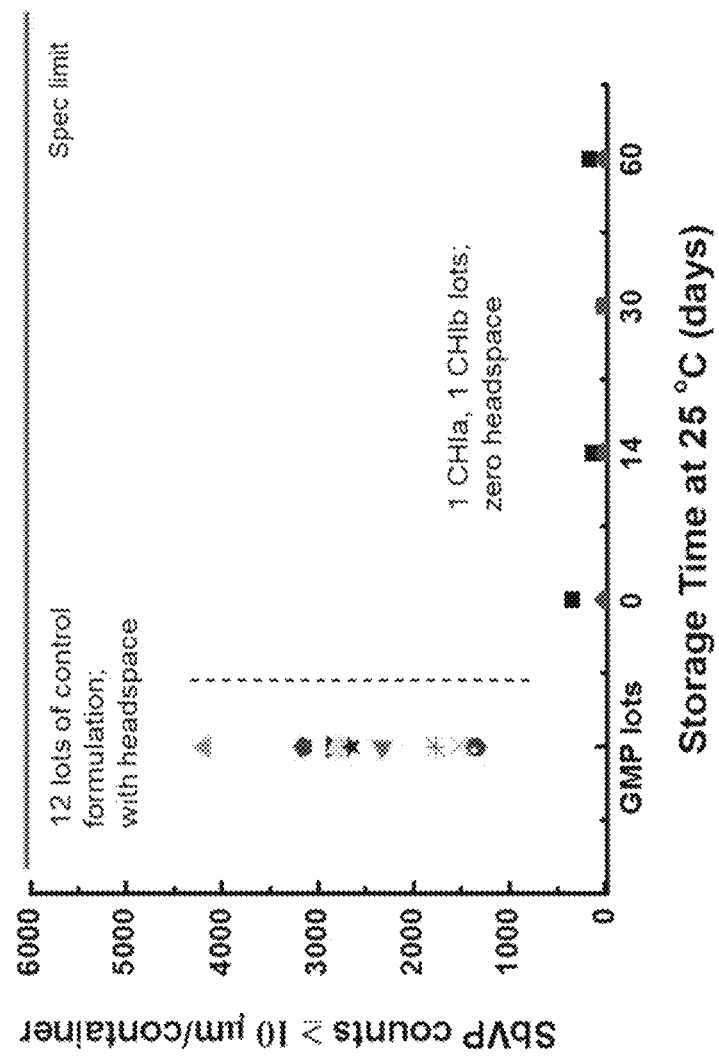
FIG. 11. Sub-visible particles 10 μm in solutions in containers with zero headspace stored at 25° C. for 60 days.

FIG. 11 demonstrates that formulations in syringes with zero headspace, irrespective of the excipients in the formulation, are thermally stable at 25° C. Specifically, the formulations have a less than 1000 sub-visible particles 10 μm in size at time 0, day 7, day 14, day 30, and day 60 when stored at 40° C.

Moreover, the particle counts observed in surfactant-free formulations in syringes with zero headspace is lower than in formulations with surfactant in syringes that have a headspace at time 0. Additionally, there is very little lot to lot variation in the zero headspace syringes.

These results demonstrate that enclosing an aqueous solution in a container with zero headspace provides thermal stability for the solution.

Sub-Visible Particles in Pegfilgrastim Formulation

Sub-visible particles were evaluated in a pegfilgrastim formulation in syringes with a headspace and in syringes with zero headspace. The pegfilgrastim solution was filled at 0.6 mL into standard Hypak PFS and closed with non-siliconized 4023 stopper. The formulation comprised 10 mg/ml pegfilgrastim, buffer, stabilizer, and surfactant, at pH 4.0. Sub-visible particles ≥2 micrometer (μm) in size and ≥5 μm in size were evaluated. Results are presented in FIG. 12.

Figure 12:
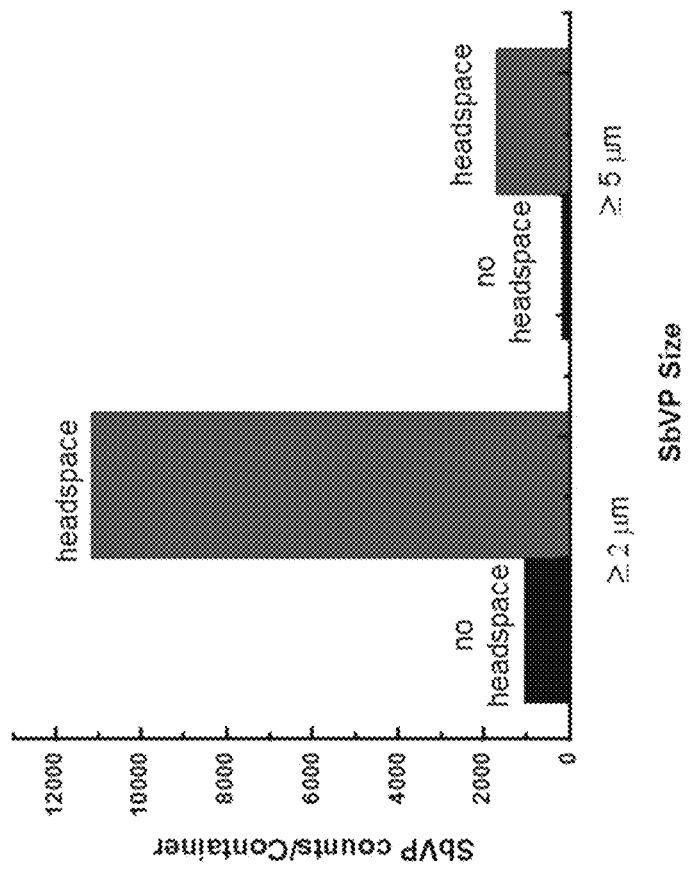
FIG. 12. Sub-visible particles in pegfilgrastim solutions in containers with zero headspace.

FIG. 12 demonstrates that the pegfilgrastim formulation in a syringe with zero headspace has significantly fewer sub-visible particles than the same formulation in a container with a headspace. Sub-visible particles ≥2 μm were reduced from over 11,000 to about 1,000-over ten-fold fewer. Sub-visible particles ≥5 μm were reduced from about 2,000 to less than 500.

These results further demonstrate that the stabilizing effect of enclosing an aqueous solution in a container with zero headspace is not limited to a particular solution or molecule of interest. Removing headspace from a container eliminates the air-water interface and prevents the headspace from mixing the solution which protects the formulation, and the therapeutic molecule, from mechanical stresses and oxidative stress.

Example 17. Stability of Formulations in Containers with Zero Headspace

Buffer-Free Formulations are pH Stable

The pH stability of buffer-free formulations in a container with zero headspace was evaluated. The pH of a formulation may vary about ±5% of the target pH and still be considered stable.

Buffer-free, and surfactant-free formulations CHG, CHIa, and CHIb were stored at 40° C. for 30 days and formulations CHIa and CHIb were stored at 25° C. for 60 days. All formulations have a target pH of 5.2 with lower and upper limits of about 4.9 and about 5.5, respectively.

Figure 13:
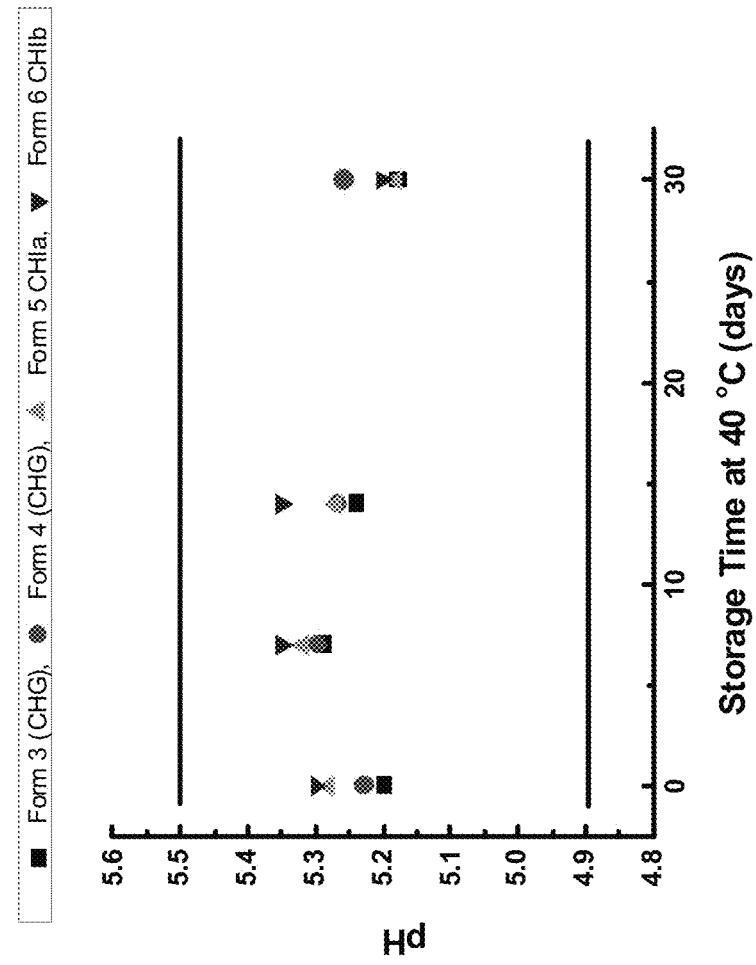
FIG. 13. pH stability of buffer-free solutions in containers with zero headspace stored at 40° C. for 30 days.

FIG. 13 demonstrates that formulations in syringes with zero headspace, are pH stable at 40° C. for up to 30 days. Specifically, the buffer-free formulations do not vary more than 5% from the target pH at time 0, day 7, day 14, and day 30 when stored at 40° C. Thus, the formulations are pH stable.

Figure 14:
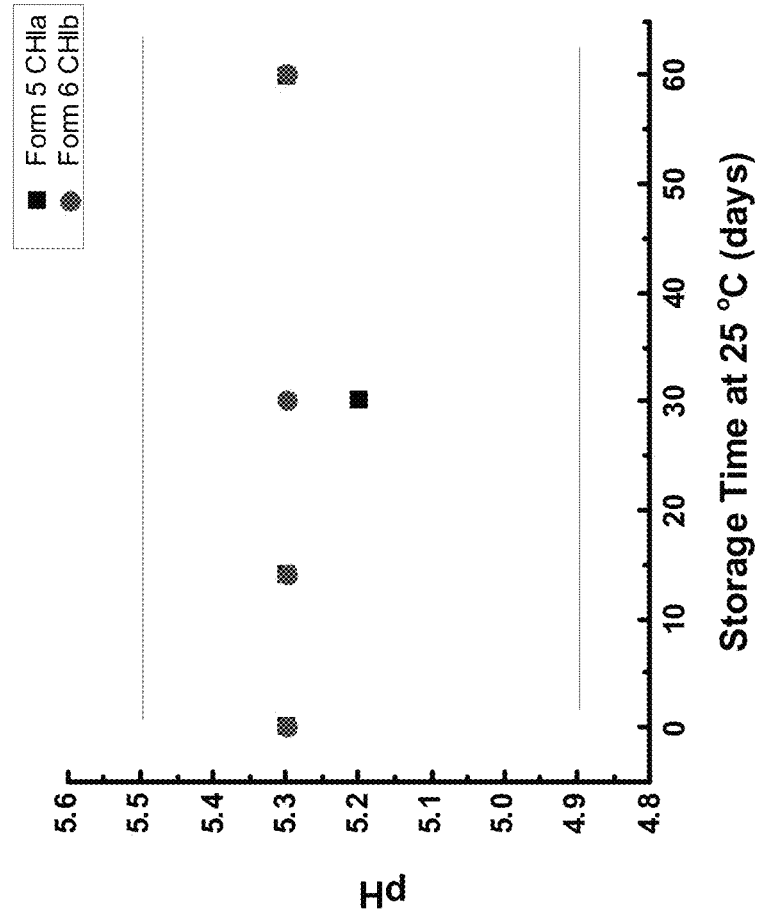
FIG. 14. pH stability of buffer-free solutions in containers with zero headspace stored at 25° C. for 60 days.

FIG. 14 demonstrates that formulations in syringes with zero headspace, are pH stable at 25° C. for up to 60 days. Specifically, the buffer-free formulations do not vary more than 5% from the target pH at 0, day 7, day 14, day 30, and day 60 when stored at 25° C. Thus, the formulations are pH stable.

These results demonstrate that an aqueous solution is pH stable when enclosed in a container with zero headspace. Specifically, these results demonstrate that dissolving a carbon dioxide headspace into a formulation to create a container with zero headspace does not adversely affect the pH of the formulation.

Aggregation—High Molecular Weight Species

Stability of formulations was evaluated by measuring the aggregation of high molecular weight species (HMWS) over time. HMWS species were measured by Size Exclusion Chromatography. Formulations CHH, CHIa, and CHIb were prepared in syringes with zero headspace. Formulation CHG was prepared in a syringe with a headspace. Control formulations CHS (control described above) and Humira are in syringes with a headspace. All formulations were stored at 40° C. for 30 days and formulations CHIa and CHIb were stored at 25° C. for 30 days.

Figure 15:
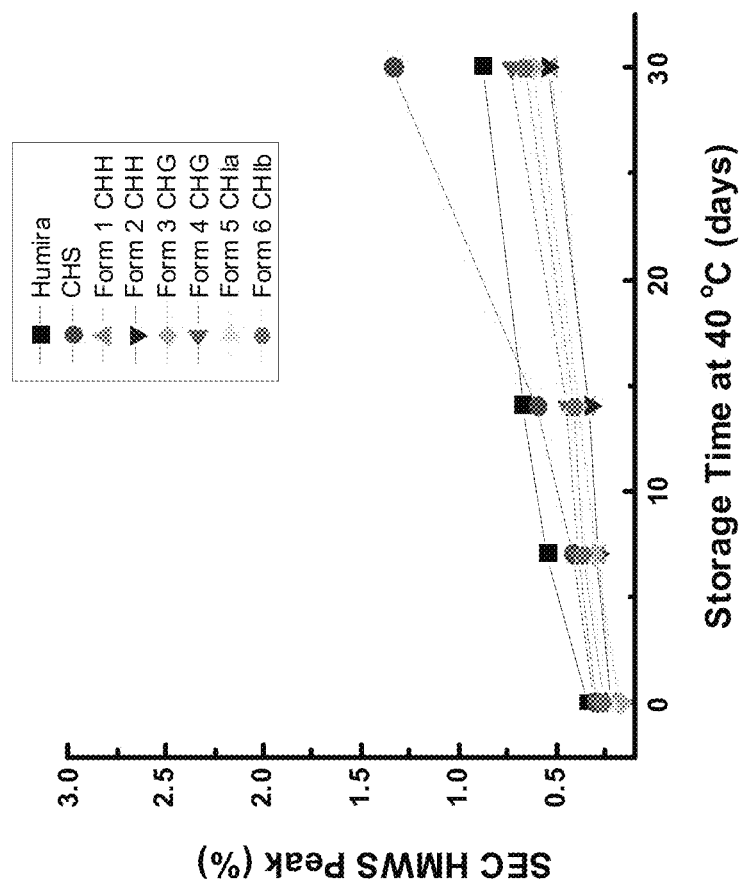
FIG. 15. Stability of solutions in containers with zero headspace stored at 40° C. for 30 days as evaluated by aggregation of high molecular weight species.

FIG. 15 demonstrates that at day 7, day 14, and day 30 the surfactant-free formulations in syringes with zero headspace (CHH, CHIa, CHIb) had a lower percentage of HWMS than the control formulation and Humira. FIG. 15 also shows that the buffer-free formulation comprising HPβCD (CHG) had a lower percentage of HWMS than the control formulation and Humira. Thus, formulations that do not contain a surfactant can be stabilized against aggregation by removing the headspace from a container or by replacing surfactant for HPβCD.

Figure 16:
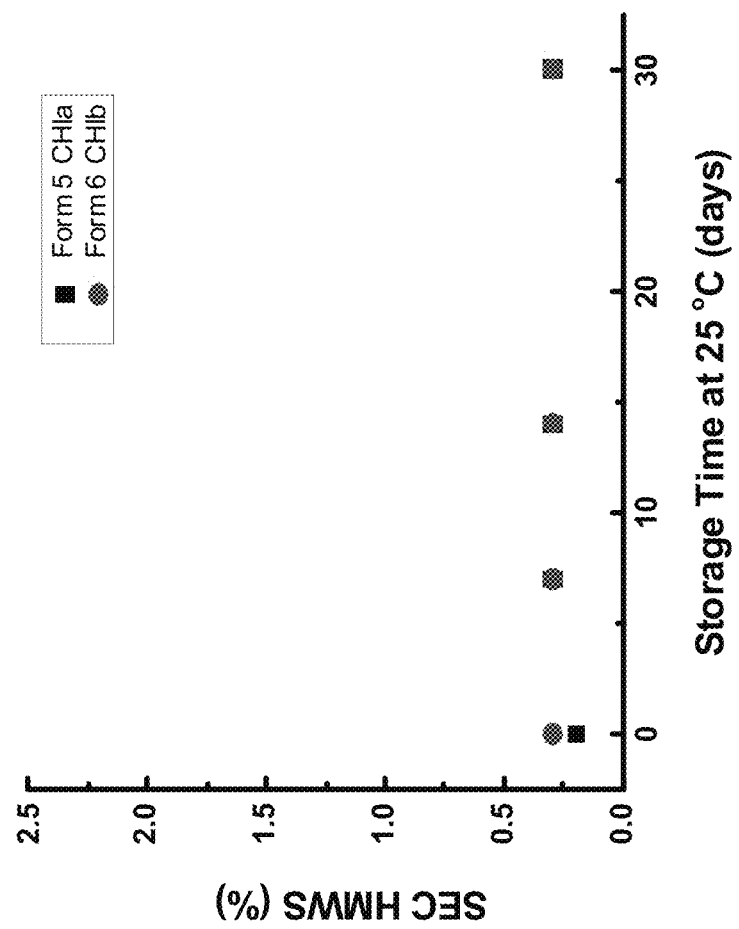
FIG. 16. Stability of solutions in containers with zero headspace stored at 25° C. for 60 days as evaluated by aggregation of high molecular weight species.

FIG. 16 demonstrates that at day 7, day 14, and day 30 surfactant-free formulations CHIa and CHIb in syringes with zero headspace had a low percentage of HWMS when stored at 25° C. Specifically, the percentage of HWMS never rises above 0.5%. These results are consistent with those observed for HMWS aggregation over time at 40° C.

Thus, a formulation in a container with zero headspace is protected against aggregation of HMWS and is stable. Moreover, adalimumab formulations in a container with zero headspace has less HMWS than Humira. In other words, adalimumab formulations in a container with zero headspace is at least as stable as Humira.

Main Peak Degradation

Stability of formulations was evaluated determining the degradation of the therapeutic molecule over time. This was done by measuring loss of the main peak of the therapeutic molecule by Cation Exchange Chromatography (CEC). Formulations CHH, CHIa, and CHIb were prepared in syringes with zero headspace. Formulation CHG was prepared in a syringe with a headspace. Control formulations CHS (control described above) and Humira are in syringes with a headspace. All formulations were stored at 40° C. for 30 days. Formulations CHIa, CHIb, Control (CHS) and Humira were stored at 25° C. for 30 days.

Figure 17:
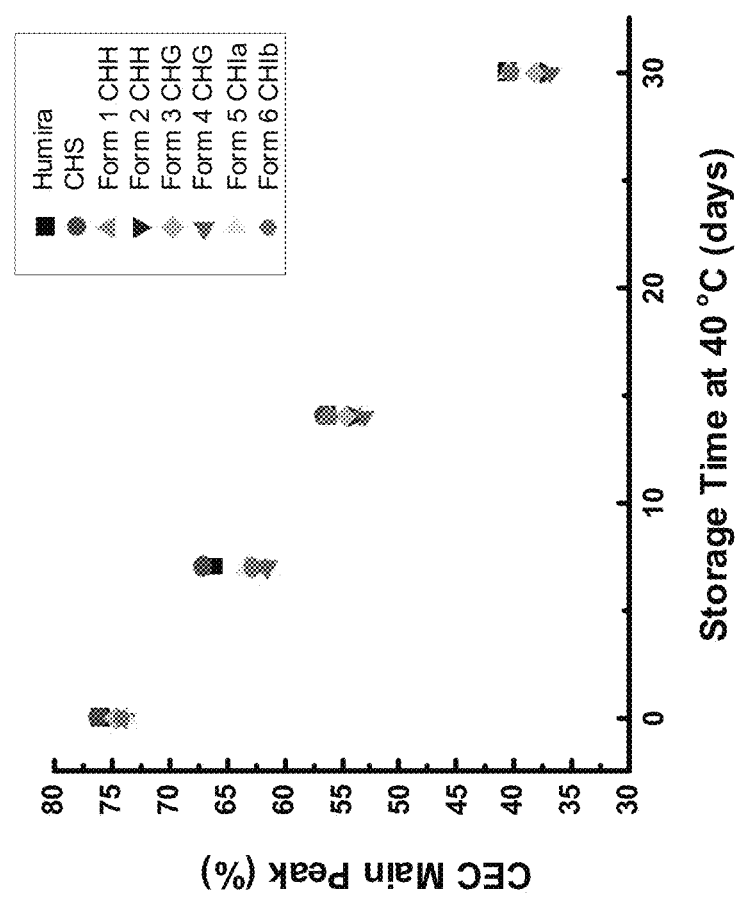
FIG. 17. Stability of solutions in containers with zero headspace stored at 40° C. for 30 days as evaluated by degradation of the main peak of the drug substance.

FIG. 17 demonstrates that at day 7, day 14, and day 30 the surfactant-free formulations in syringes with zero headspace (CHH, CHIa, CHIb) had similar loss of main peak as the control formulation and Humira. FIG. 17 also shows that the buffer-free formulation comprising HPβCD (CHG) had similar loss of main peak as the control formulation and Humira. Thus, formulations that do not contain a surfactant can be stabilized against loss of the active therapeutic molecule by removing the headspace from a container or by replacing surfactant for HPβCD.

Figure 18:
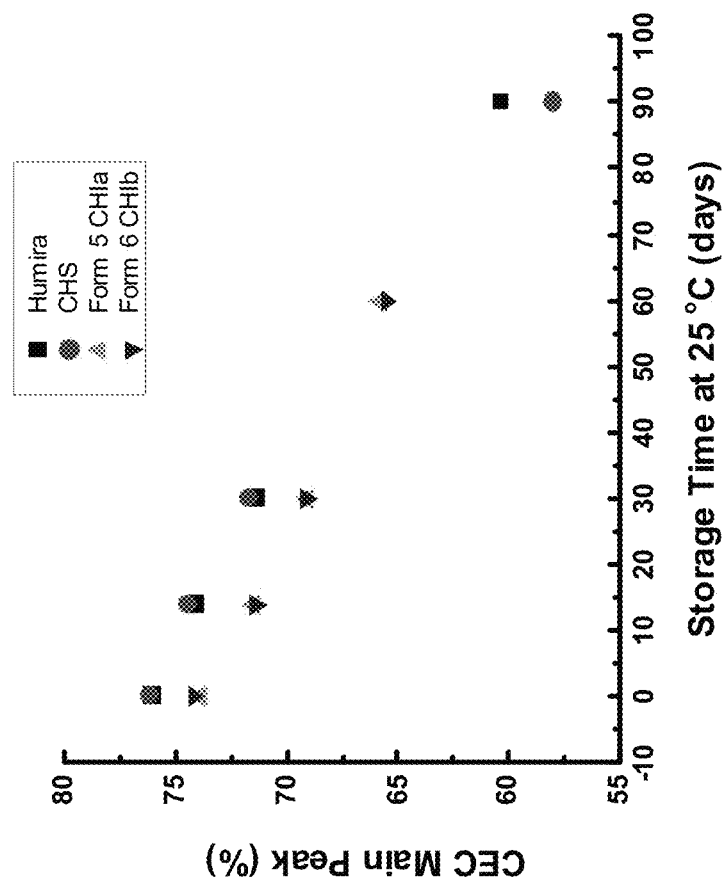
FIG. 18. Stability of solutions in containers with zero headspace stored at 25° C. for 60 days as evaluated by degradation of the main peak of the drug substance.

FIG. 18 demonstrates that at day 7, day 14, and day 30 surfactant-free formulations CHIa and CHIb in syringes with zero headspace had rate of main peak loss similar to, or slightly better (i.e. less loss), than the rate of loss in the control formulation and Humira when stored at 25° C. These results are consistent with those observed for main peak loss over time at 40° C.

Thus, a formulation in a container with zero headspace is protected against loss of the active therapeutic molecule and is stable. Moreover, adalimumab formulations in a container with zero headspace had loss of the active therapeutic molecule comparable to the loss in Humira. In other words, adalimumab formulations in a container with zero headspace is at least as stable as Humira.

Oxidation of Therapeutic Molecule

The stability the therapeutic molecule in a container with zero headspace is evaluated for oxidation upon expose to light. Three adalimumab formulations (e.g. CHH, CHIa, CHIb) in syringes with zero headspace and one control formulation in a syringe are evaluated.

Formulations are exposed to 1000 lux or 4000 lux and samples are evaluated at the following time points at t0 (no light baseline); 1000 lux: 2 days, 4 days, and 7 days; and 4000 lux: 4 days and 7 days.

Samples are expelled from the syringe and analytics in table 21 are performed.

TABLE 21

| Analytical Method | Purpose | Time Points |
|---|---|---|
| Visual Inspection | Appearance and Clarity | All |
| pH | Buffer capacity | All |
| UV-Vis | Concentration | t0 and 7 d |
| SE-HPLC or UPLC | Size distribution | All |
| CEC-HPLC | Charge Variants | All |
| CE-SDS (NR and R) | Size distribution | All |
| HIAC/MFI | SVP Levels | All |

Formulations in container with zero headspace have reduced exposure to molecular oxygen as compared to a formulation in a container with a headspace. Therefore, oxidative degradation of the therapeutic molecule in container with zero headspace is comparable to, or less than, oxidative degradation of the therapeutic molecule in container with a headspace.

What is claimed is:

1. A method for preparing a container with zero headspace comprising an aqueous adalimumab solution, the method comprising:
   a) providing a container with an open end;
   b) providing an aqueous adalimumab solution comprising about 30 mg/mL to about 50 mg/mL adalimumab and not comprising a polyol, a sugar, or a surfactant;
   c) filling the container via the open end with the aqueous adalimumab solution;
   d) purging the container with at least one soluble gas;
   e) inserting a stopper into the open end of the container creating a headspace of soluble gas; and
   f) storing the container,
   wherein the stopper can move within the container while maintaining an airtight seal; and the storing step results in the container having zero headspace,
   wherein, following the storing step, the aqueous adalimumab solution comprises less than about 6,000 subvisible particles having a size of ≥10 μm per 0.8 mL of the aqueous adalimumab solution and less than about 600 subvisible particles having a size of ≥25 μm per 0.8 mL of the aqueous adalimumab solution.

2. The method of claim 1, wherein prior to the purging step or prior to inserting the stopper, the container is subjected to a pressure vacuum.

3. The method of claim 1, wherein the soluble gas is carbon dioxide.

4. The method of claim 1, wherein the container is stored for at least 4 hours.

5. The method of claim 1, wherein the storing step is conducted at a temperature below the temperature at which the stoppering step occurred.

6. The method of claim 1, comprising the steps:
   a) providing a container with an open end;
   b) providing an aqueous adalimumab solution;
   c) filling the container via the open end with the aqueous adalimumab solution;
   d) degassing the container and aqueous adalimumab solution via a pressure vacuum;
   e) purging the container with at least one soluble gas;
   f) optionally repeating the degassing and purging steps;
   g) degassing via a pressure vacuum and while under vacuum, inserting a stopper into the open end of the container creating a headspace of soluble gas; and
   h) storing the container.

7. The method of claim 1, wherein the container is a syringe or a cartridge.

8. The method of claim 1, wherein the aqueous drug substance solution is further free or substantially free of buffer, salt, stabilizer, or any combination thereof.

* * * * *